(12) United States Patent
Shi

(10) Patent No.: US 6,686,483 B2
(45) Date of Patent: *Feb. 3, 2004

(54) CATALYTIC ASYMMETRIC EPOXIDATION

(75) Inventor: Yian Shi, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/041,953

(22) Filed: Jan. 7, 2002

(65) Prior Publication Data

US 2002/0133031 A1 Sep. 19, 2002

Related U.S. Application Data

(63) Continuation-in-part of application No. 09/663,390, filed on Aug. 10, 2000, now Pat. No. 6,369,245, and a continuation-in-part of application No. 09/534,419, filed on Mar. 23, 2000, now Pat. No. 6,384,265, and a continuation-in-part of application No. 09/673,335, filed as application No. PCT/US99/08418 on Apr. 16, 1999, now Pat. No. 6,409,769, application No. 10/041,953, which is a continuation-in-part of application No. 09/284,054, filed as application No. PCT/US97/18310 on Oct. 8, 1997, now Pat. No. 6,348,608.
(60) Provisional application No. 60/125,687, filed on Mar. 23, 1999, provisional application No. 60/148,904, filed on Aug. 13, 1999, provisional application No. 60/082,029, filed on Apr. 16, 1998, and provisional application No. 60/028,009, filed on Oct. 8, 1996.

(51) Int. Cl.$^7$ .................. C07D 301/12; C07D 301/14; C07D 301/19; C07C 45/58; C07C 69/78
(52) U.S. Cl. ............... 549/525; 549/524; 549/529; 549/531; 549/541; 560/106; 568/361; 568/375; 568/376
(58) Field of Search .................. 549/525, 524, 549/529, 531, 541; 560/106; 568/361, 375, 376

(56) References Cited

U.S. PATENT DOCUMENTS

| | | |
|---|---|---|
| 4,902,820 A | 2/1990 | Zoeller |
| 5,403,549 A | 4/1995 | McNeil et al. |
| 5,414,078 A | 5/1995 | Liotta et al. |
| 5,859,265 A | 1/1999 | Müller et al. |
| 6,060,610 A | 5/2000 | Arca et al. |
| 6,160,137 A | 12/2000 | Tsuji |
| 6,160,138 A | 12/2000 | Escrig et al. |
| 6,194,591 B1 | 2/2001 | Grey et al. |
| 6,225,482 B1 | 5/2001 | Drauz et al. |
| 6,348,608 B1 | 2/2002 | Shi |
| 6,369,245 B1 | 4/2002 | Shi |

OTHER PUBLICATIONS

U.S. patent application Ser. No. 09/534,419, Shi, filed Mar. 23, 2000.
Tetrahedron, 1962, 18, 763–765.
J. Org. Chem. 1997, 62, 188–193.
Tu et al., J. Am. Chem. Soc., 1996, 118, 9806–9807.
Wang et al., J. Am. Chem. Soc., 1997, 119, 11224–11235.
Wang, et al., J. Org. Chem., 1997, 62, 2328–2329.
Wang et al., J. Org. Chem., 1997, 62, 8622–8623.
Kurihara et al., Tet. Lett., 1994, 35, 1577–1580.
Denmark et al., J. Org. Chem., 1995, 60, 1391–1407.
Cicala et al., J. Org. Chem., 1982, 47, 2670–2673.
Curci et al., J. Org. Chem., 1980, 45, 4758–4760.
Besse et al., Tetrahedron, 1994, 50, 8885–8927.
Curci et al., J. Chem. Soc., 1984, 155–156.
Curci et al. Tet. Lett., 1995, 36, 5831–5834.
Brown et al., Tetrahedron, 1995, 51, 3587–3606.
Denmark et al., J. Org. Chem., 1997, 62, 8288–8289.
Yang et al., J. Am. Chem. Soc., 1996, 118, 491–492.
Yang et al., J. Am. Chem. Soc., 1996, 118, 11311–11312.
Armstrong et al., Tetrahedron: Asymmetry, 1997, 8, 1677–1684.
Song et al., Tetrahedron: Asymmetry, 1997, 8, 2921–2926.
Aggarwal et al., Chem. Commun., 1996, 191–192.
Davis et al., Tet. Lett., 1986, 27, 5079–5082.
Ebrahim et al., Tetrahedron: Asymmetry, 1997, 8, 3163–3173.
Kroutil et al., J. Chem. Soc., Perkin Trans. I, 1996, 2837–2844.
Kroutil et al., Chem. Commun., 1996, 845–846.
Itsuno et al., J. Org. Chem., 1990, 55, 6047–6049.
Tipson et al., Carbohyd. Res., 1971, 16, 383–393.
DuPenhoat et al., Carbohyd. Rest., 1979, 71, 135–148.
Chughtal et al., Abstracts, 1996, 212th ACS National Meetings, Am. Chem. Soc.

(List continued on next page.)

Primary Examiner—Ba K. Trinh
(74) Attorney, Agent, or Firm—Faegre & Benson LLP

(57) ABSTRACT

The present invention provides a variety of methods that are based on stereoselective epoxidation of an olefin by an epoxidizing agent derived from a reaction between an oxidizing agent and a chiral ketone. For example, present invention provides methods for producing an epoxide from an olefin, for increasing a relative concentration of at least one stereoisomer of an olefin, and for stereoselectively producing an α-acyloxy carbonyl compound. Preferably, the chiral ketone is of the formula:

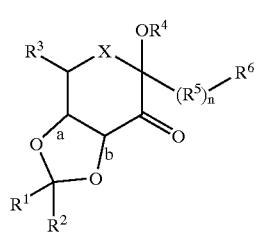

I or a derivative thereof which is capable of converting to the chiral ketone of Formula I under the reaction conditions, where a, b, n, X, $R^1$, $R^2$, $R^3$, $R^4$, $R^5$ and $R^6$ are those defined herein.

25 Claims, 18 Drawing Sheets

OTHER PUBLICATIONS

McDonald, *Mech.,Mol. Migr.*, 1971, *3*, 67.
Soloway et al., *J. Am. Chem. Soc.*, 1954, *76*, 2941.
Leeds et al., *J. Am. Chem. Soc.*, 1954, *76*, 2943.
Gardner, *J. Am. Chem. Soc.*, 1956, *78*, 3421.
Johnson et al., *J. Am. Chem. Soc.*, 1957, *79*, 1991.
Shine et al., *J. Am. Chem. Soc.*, 1958, *80*, 2434.
House et al., *J. Org. Chem.*, 1961, *26*, 3729.
Attenburrow et al., *J. Am. Chem. Soc.*, 1961, 4547.
Williamson et al., *J. Org. Chem.*, 1961, *26*, 4563.
Nambara et al., *J. Org. Chem.*, 1962, *27*, 2131.
Draper et al., *J. Org. Chem*, 1962, *27*27.
Riehl et al., *Bull. Soc. Chim. Fr.*, 1963, 224.
Rhone, *Tet. Lett.*, 1965, 1395.
Williamson et al., *J. Org. Chem.*, 1967, *32*, 3934.
McDonald et al., *J. Am. Chem. Soc.*, 1967, *89*, 6573.
Smith et al., *J. Org. Chem.*, 1992, *57*, 6379.
Zhu et al., *J. Am. Chem. Soc.*, 1999, *121*, 4080.
Feng et al., *J. Am. Chem. Soc.*, 1999, *121*, 11002.
Zhu, *J. Org. Chem.*, 2001, *66*, 1818.
Williamson et al., *J. Org. Chem.*, 1967, *32*(*12*), 3934–7.
Adam et al., *J. Am. Chem. Soc.*, 1998, *120*, 708–714.
Schulz et al., *J. Org. Chem.*, 1997, *62*, 188–193.
Payne, *Tetrahedron*, 1962, *18*, 763–765.
Murray, et al., *J. Am. Chem. Soc.*, 1992, *114*, 1346–1351.

| Entry | $R_{12}, R_{13}$ | $R_{14}, R_{15}$ | $R_{16}$ | Olefin | %Conv. | %ee |
|---|---|---|---|---|---|---|
| 1 | Me, Me | Me, Me | H | β-methylstyrene | 96 | 92 |
| 2 | Me, Me | Et, Et | H | " | 91 | 91 |
| 3 | Me, Me | Et, H | H | " | 79 | 91 |
| 4 | Me, Me | Ph, H | H | " | 59 | 91 |
| 5 | Me, Me | i-Pr, H | H | " | 64 | 88.5 |
| 6 | Me, Me | -(CH$_2$)$_4$- | H | " | 95 | 92 |
| 7 | Me, Me | -(CH$_2$)$_5$- | H | " | 95 | 89 |
| 8 | Me, Me | Bn, Bn | H | " | 17 | 66 |
| 9 | Et, Et | Et, Et | H | " | 32 | 87 |
| 10 | Et, Et | Me, Me | H | " | 89 | 90 |
| 11 | -(CH$_2$)$_4$- | -(CH$_2$)$_4$- | H | " | 89 | 94 |
| 12 | -(CH$_2$)$_4$- | Me, Me | H | " | 100 | 93 |
| 13 | -(CH$_2$)$_4$- | -(CH$_2$)$_5$- | H | " | 51 | 87 |
| 14 | -(CH$_2$)$_4$- | Me, Me | H | " | 95 | 91 |
| 15 | -(CH$_2$)$_4$- | -(CH$_2$)$_6$- | H | " | 37 | 91 |
| 16 | Me, Me | Me, Me | CH$_2$OH | " | 16 | 12.5 |

| Entry | Ketone (eq.) | Olefin | Conversion (%) | ee (%) |
|---|---|---|---|---|
| 1 | (structure, MOMO) (0.5) | β-methylstyrene | 80 | 85 |
| 2 | (structure, OMOM) (0.1) | " | 59 | 72.5 |
| 3 | (structure, OMOM) (0.1) | " | 50 | 71.4 |
| 4 | (structure, MeO2C) (0.1) | " | 90 | 66.5 |
| 5 | (structure, AcO) (0.05) | Styrene | 96 | 64.6 |
| 6 | (structure, BzO) (0.05) | " | 99 | 64.8 |
| 7 | (structure, TsO) (0.05) | " | 70 | 67.0 |
| 8 | (structure, TBSO) (0.1) | " | 100 | 65.9 |

Figure 5

| Entry | $R_{14}$, $R_{15}$ | Olefin | %Conv. | %ee |
|---|---|---|---|---|
| 1 | Me, Me | β-methylstyrene | 44 | 61 |
| 2 | Et, Et | " | 33 | 61 |
| 3 | Pr, Pr | " | 28 | 82 |
| 4 | Ph, Ph | " | 25 | 48 |
| 5 | Bn, Bn | " | 19 | 61 |
| 6 | -(CH$_2$)$_5$- | " | 52 | 52 |
| 7 | -(CH$_2$)$_4$- | " | 36 | 61 |

6a $R_{19}$ = CO$_2$Me
6b $R_{19}$ = Ac
6c $R_{19}$ = Bz
6d $R_{19}$ = Ts
6e $R_{19}$ = OTBS

| Catalyst | Ph⁀Ph | | | ⌬ | | | Ph⁀ | | |
|---|---|---|---|---|---|---|---|---|---|
| | Cat (mol%) | Yield (%) | ee (%) | Cat (mol%) | Conv. (%) | ee (%) | Cat (mol%) | Conv. (%) | ee (%) |
| 6a | 10 | 66 | 94.7 | 10 | 56 | 66.3 | 10 | 90 | 66.5 |
| 6b | 10 | 95 | 90.3 | 10 | 82 | 67.8 | 5 | 96 | 64.6 |
| 6c | 10 | 91 | 89.6 | 10 | 67 | 71.4 | 5 | 99 | 64.8 |
| 6d | 10 | 74 | 90 | 10 | 62 | 70.6 | 5 | 70 | 67.0 |
| 6e | 10 | 77 | 89.5 | 10 | 70 | 73.2 | 10 | 100 | 65.9 |

| Entry | Substrate | Cat.(mol%) | T(°C) | time(h) | Yield(%) | ee(%) | Config. |
|---|---|---|---|---|---|---|---|
| 1 | Ph⁀Ph | 10 | -10 | 6 | 95 | 90.3 | (+)-(R,R) |
| 2 | Ph⁀CO₂Et | 10 | 0 | 8 | 34 | 85.9 | (+)-(2S,3R) |
| 3 | Ph⁀C(O)Ph | 10 | 0 | 6 | 80 | 93.8 | (+)-(2S,3R) |
| 4 | Ph⁀Me | 5 | -15 | 4 | 92 | 75.3 | (+)-(R,R) |
| 5 | Ph⁀Cl | 10 | 0 | 5 | 94 | 76.7 | (+)-(2S,3R) |
| 6 | Ph₂C=CHPh | 10 | 0 | 5 | 86 | 87.3 | (-)-(R) |
| 7 | Ph-CH=CH₂ | 5 | -10 | 4 | 90 | 64.6 | (-)-(R) |
| 8 | p-vinyl Ph | 5 | -10 | 4 | 54 | 64.8 | (-) |
| 9 | mesityl vinyl | 5 | -10 | 4 | 83 | 66 | (-) |
| 10 | 2-vinyl naphthyl | 5 | -10 | 4 | 89 | 54 | (-)-(R) |
| 11 | Ph-C(Me)=CH₂ | 5 | -10 | 3 | 92 | 52.1 | (+)-(R) |
| 12 | cyclohexene ketal | 10 | -10 | 6 | 78 | 67.8 | (+)-(R,R) |

Figure 8

Asymmetric Epoxidation of *trans*-Stilbene via Ketone 1

| Entry | Time (h) | Isolated Yield (%) | ee (%) |
|---|---|---|---|
| 1 | 1 | 31 | >95 |
| 2 | 2 | 39 | >95 |
| 3 | 4 | 40 | 89 |
| 4 | 8 | 47 | 85 |

Figure 9

The Solvent Effects on the Asymmetric Epoxidation

| Entry | Solvent | T (°C) | Time(min) | Conversion(%) | %ee |
|---|---|---|---|---|---|
| 1 | $CH_3CN$ | 20 | 20 | 100 | 89 |
| 2 | $CH_3CN$ | 0 | 90 | 96 | 92 |
| 3 | $CH_3CH_2CN$ | 20 | 60 | 11 | 80 |
| 4 | DMM | 20 | 60 | 36.2 | 91 |
| 5 | DME | 20 | 20 | 100 | 89 |
| 6 | DME | 0 | 90 | 92 | 89 |
| 7 | DMF | 20 | 20 | 95 | 86 |
| 8 | Dioxane | 20 | 20 | 100 | 86 |
| 9 | Dioxane | 0 | 90 | 96 | 86 |
| 10 | THF | 20 | 60 | 18 | 74 |
| 11 | $Et_2O$ | 20 | 60 | 0 | |
| 12 | $CH_2Cl_2$ | 20 | 30 | <3 | nd |
| 13 | $CH_3CN$/DMM (2/1) | 20 | 20 | 100 | 90 |
| 14 | $CH_3CN$/DMM (2/1) | 0 | 90 | 100 | 92 |
| 15 | $CH_3CN$/DMM (1/1) | 20 | 20 | 98 | 91 |
| 16 | $CH_3CN$/DMM (1/1) | 0 | 90 | 100 | 93 |
| 17 | $CH_3CN$/DMM (½) | 20 | 20 | 94 | 92 |
| 18 | $CH_3CN$/DMM (½) | 0 | 90 | 88 | 94 |
| 19 | $CH_3CN$/DMM (1/4) | 0 | 90 | 77 | 94 |
| 20 | DMM/DME (1/1) | 20 | 25 | 66 | 92 |
| 21 | $CH_3CN$/DMM/DME(1/1/2) | 20 | 20 | 100 | 90 |
| 22 | $CH_3CN$/DMM/DME | 20 | 20 | 89 | 90 |
| 23 | $CH_3CN$/THF(1/1) | 20 | 25 | 63 | 82 |
| 24 | $CH_3CN$/$Et_2O$ (1/1) | 20 | 25 | 28 | 84 |
| 25 | $CH_3CN$ | 0 | 240 | 58.4 | 63.4 |
| 26 | DME | 0 | 240 | 100 | 69.6 |
| 27 | DME | -10 | 240 | 95 | 73.1 |
| 28 | DMM | 0 | 240 | 43 | 66.3 |
| 29 | Dioxane | 0 | 240 | 99.4 | 66.6 |
| 30 | DMM/$CH_3CN$ (2/1) | 0 | 240 | 91 | 67.1 |
| 31 | DMF | 0 | 180 | 99 | 64.3 |

Figure 10

The Temperature Effect on the Epoxidation of *trans*-β-Methylstyrene by Ketone 1

| Entry | T(°C) | Conv.(%) | ee(%) |
|-------|-------|----------|-------|
| 1 | -11 | 99.4 | 95.7 |
| 2 | -6 | 96.9 | 95.4 |
| 3 | -2 | 97.5 | 95.2 |
| 4 | 2 | 99.4 | 94.7 |
| 5 | 8 | 99.0 | 93.8 |
| 6 | 20 | 99.0 | 93.2 |
| 7 | 30 | 96.8 | 91.1 |

Figure 11

Asymmetric Epoxidation of Representative *trans*-disubstituted Olefins by Ketone 1 and ent-1.

| Entry | Substrate | Method[a] | T (°C) | % Yield | %ee | Configuration |
|---|---|---|---|---|---|---|
| 1 | Ph/\/\Ph | A | 0 | 73 | 95.2 | (+)-(R,R) |
| | | B | 0 | 75 | 97 | |
| | | C | 0 | 78 | 98.9 | |
| | | | 20 | 85 | 97.9 | |
| | | C(ent-1) | 0 | 81 | 98.3 | (-)-(S,S) |
| 2 | Ph/\/ | A | 0 | 81 | 88 | (+)-(R,R) |
| | | B | 0 | 93 | 91.7 | |
| | | C | -10 | 94 | 95.5 | |
| | | C(ent-1) | -10 | 94 | 95.7 | (-)-(S,S) |
| 3 | Ph/\/\OTBS | A | 0 | 74 | 93 | (+)-(R,R) |
| | | B | 0 | 87 | 94 | |
| | | C | 0 | 71 | 95.2 | |
| 4 | Ph/\/\OCPh₃ | C | 0 | 55 | 94.0 | (+)-(R,R) |
| 5 | Ph/\/\Cl | A | 0 | 61 | 93 | (+)-(2S,3R) |
| | | C | 0 | 49 | 96.2 | |
| 6 | Ph/\/-dioxolane | A | 0 | 41 | 93 | (+)-(2S,3R) |
| 7 | o-I-C₆H₄-CH=CHMe | C | -10 | 91 | 93.3 | (+)-(R,R) |
| 8 | o-I-C₆H₄-CH=CH-iPr | C | -10 | 78 | 95.7 | (-)-(R,R) |
| 9 | /\/\/\OTBS | A | 0 | 80 | 93 | (+)-(R,R) |
| | | C | -10 | 83 | 94.5 | |
| 10 | /\/\/\OTBS | A | 0 | 84 | 87 | (+)-(R,R) |
| | | C | -10 | 85 | 93 | |
| 11 | C₆H₁₃/\/C₆H₁₃ | A | 0 | 81 | 90 | (+)-(R,R) |
| | | B[b] | 0 | 88 | 93 | |
| | | C | -10 | 89 | 95 | |
| 12 | C₄H₉/\/C₄H₉ | B[b] | 0 | 70 | 91 | (+)-(R,R) |
| 13 | /\/\/-dioxolane | C | -10 | 92 | 92 | (+)-(R,R) |
| 14 | Ph/\/\/C(O)OMe | B | 0 | 76 | 91 | (+)-(R,R) |
| | | C | 0 | 68 | 92 | |

Figure 12

Asymmetric Epoxidation of Representative Trisubstituted Olefins by Ketone 1 & ent-1

| Entry | Substrate | Method[a] | T (°C) | Yield[b] (%) | ee (%) | Config. |
|---|---|---|---|---|---|---|
| 1 | Ph-C(CH3)=CH-Ph | A | 0 | 73 | 92 | (+)-(R,R) |
|   |   | C | 0 | 89 | 95.5 |   |
| 2 | Ph-C(Ph)=CH-Ph | A | 0 | 65 | 92.2 | (-)-(R) |
|   |   | C | 0 | 54 | 96.7 |   |
| 3 | 1-Ph-cyclohexene | A | 0 | 69 | 91 | (-)-(R,R) |
|   |   | C | -10 | 94 | 98 |   |
| 4 | 4-Ph-dihydronaphthalene | A | 0 | 74 | 94 | (-)-(1S,2R) |
|   |   | C | -10 | 98 | 95.2 |   |
| 5 | Ph2C=CH-C10H21 | B | 0 | 66 | 93.5 | (+)-(R) |
|   |   | C | 0 | 92 | 97.0 |   |
| 6 | Ph-C(Me)=CH-Me | C | -10 | 89 | 96.8 | (R,R) |
| 7 | Ph-CH=C(Me)2 | C | -10 | 93 | 76.4 | (+)-(R) |
| 8 | C10H21-CH=C(Me)2 | C | -10 | 97 | 86.5 | (+)-(R) |
| 9 | (Me)2C=C(Me)2 type | C (ent-1) | -10 | 35 (100') | 91 | (-)-(R) |
| 10 | C10H21-C(Et)=CH-Et | C | -10 | 94 | 88.5 | (+)-(R) |
| 11 | C6H13-C(Me)=CH-CH2-CO2Et | C | -10 | 91 | 83.5 | (+)-(R,R) |
| 12 | Cy-CH=C(Me)-CH2-CO2Me | C | -10 | 89 | 94 | (+)-(R,R) |
| 13 | 1-Me-cyclohexene | C | -10 | 77 (100 ) | 81 | (+)-(1S,2R) |
| 14 | dioxolane-cyclohexene | C (ent-1) | -10 | 41 | 97.2 | (-)-(R,R) |

Figure 13

Asymmetric Epoxidation of Representative *cis*-Disubstituted & Terminal Olefins by Ketone 1.

| Entry | Substrate | Method | T (°C) | Yield (%) | ee (%) | Config. |
|---|---|---|---|---|---|---|
| 1 | Ph⌒⫽ | B | -10 | 64 | 13.6 | (+)-(R) |
|   |   | C | -10 | 90 | 24.3 |   |
| 2 | C₈H₁₇⌒⫽ | B | -10 | 80 | 27 | (+)-(R) |
|   |   | C | -10 | 92 | 17 |   |
| 3 | iPr₃Si⌒⌒⫽ | B | -10 | 92.2 | 35 | (-) |
|   |   | C | -10 | 99 | 31 |   |
| 4 | Ph-C(=CH₂)Me | B | -10 | 81.3 | 27.6 | (-)-(S) |
|   |   | C | -10 | 95 | 19.6 |   |
| 5 | dihydronaphthalene | B | -10 | 85.2 | 32 | (-)-(1S,2R) |
|   |   | C | -10 | 92 | 12 |   |
| 6 | cyclohexene ketal | B | -10 | 50 | 56.2 | (+)-(R,R) |
|   |   | C | -10 | 43 | 61.4 |   |

The effect of the size of substituents on enantioseletivities using chiral ketone 1 (see Figure 1)

| Asymmetric Epoxidation of Representative Dienes by Ketone 1[a] | | | | | |
|---|---|---|---|---|---|
| Entry | Dienes | Epoxides | %Conv | Ratio | %Yield[b] %ee[c] |
| 1 | Ph~~~Ph | Ph-epoxide-Ph ; Ph-diepoxide-Ph | 94 | 22:1 | 77  98.2 |
| 2 | cyclohexenyl-cyclohexene | cyclohexyl-epoxide ; diepoxide | 100 | 12:1 | 54  95 |
| 3 | ~~~CO2Et | epoxide-CO2Et ; diepoxide-CO2Et | 69 | 7:1 | 41(7)  96(69) |
| 4 | ~~~OAc | epoxide-OAc ; diepoxide-OAc | 100 | 4:1 | 74(18)  92(90) |
| 5 | ~~~OTBS | epoxide-OTBS ; diepoxide-OTBS | 100 | 4:1 | 68(13)  96(90) |
| 6 | ~~~C(Me)2OMe | epoxide-C(Me)2OMe | 100 | only | 72  88 |
| 7 | Me-diene-OH | Me-epoxide-OH | 100 | only | 68  90 |
| 8 | Me-diene-CO2Et | Me-epoxide-CO2Et | 88 | only | 82  95 |
| 9 | branched diene-CO2Et | branched epoxide-CO2Et | 76 | only | 68  93 |
| 10 | ~~~SiMe3 | epoxide-SiMe3 ; diepoxide-SiMe3 | 100 | 3.3:1 | 65  87 |
| 11 | Ph-Me-diene-SiMe3 | Ph-Me-epoxide-SiMe3 | 100 | only | 77  94 |
| 12 | iPr-Ph-diene-SiMe3 | iPr-Ph-epoxide-SiMe3 | 100 | only | 81  95 |
| 13 | Me-diene-SiMe3 | Me-epoxide-SiMe3 | 100 | only | 60  92 |
| 14 | branched-SiMe3 | branched-epoxide-SiMe3 | 100 | only | 79  95 |

Figure 16

The Effects of Different Acid Catalysts on the Rearrangement of 1-benzoyloxy-1,2-epoxycyclohexane(1)

| entry | acid | t(min) | %ee(1) | %ee(2) | %yield |
|---|---|---|---|---|---|
| 1 | p-TsOH | 10 | 93 | 90(R) | 89 |
| 2 | Sn(OTf)$_2$ | 10 | 93 | 85(R) | 84 |
| 3 | AlCl$_3$ | 1 | 92 | 26(R) | 74 |
| 4 | La(OTf)$_3$ | 40 | 93 | 15(R) | 88 |
| 5 | Yb(OTf)$_3$ | 5 | 92 | 66(R) | 67 |
| 6 | YbCl$_3$ | 90 | 93 | 82(S) | 76 |
| 7 | ZnBr$_2$ | 10 | 93 | 12(S) | 48 |
| 8 | ErCl$_3$ | 90 | 90 | 80(S) | 73 |
| 9 | AlMe$_3$ | 5 | 91 | 87(S) | 85 |
| 10 | AlEt$_2$Cl | 17 | 91 | 67(S) | 54 |
| 11 | AlEtCl$_2$ | 10 | 91 | 30(S) | 41 |
| 12 | Silica gel | 720 | 92 | 91(S) | 83 |

Rearrangements of Enol Ester Epoxides Catalyzed by p-TsOH, Silica gel, YbCl₃, or AlMe₃.[a]

| entry | epoxide | acid | time (h) | epoxide (%ee) | product ee (%)[d] | yield (%) |
|---|---|---|---|---|---|---|
| 1 | | p-TsOH | 0.2 | 93 | 90(99)(R) | 89 |
|   | | silica gel | 12 | 92 | 91 (S) | 83 |
|   | | YbCl₃ | 0.5 | 92 | 88 (S) | 73 |
|   | | AlMe₃ | 0.1 | 91 | 87 (S) | 85 |
| 2 | | p-TsOH | 0.1 | 93 | 93(99)(R) | 70 |
|   | | silica gel | 19 | 93 | 88 (S) | 87 |
|   | | AlMe₃ | 0.1 | 91 | 85 (S) | 85 |
| 3 | | p-TsOH | 0.3 | 92 | 87(99)(R) | 72 |
|   | | silica gel | 12 | 92 | 90 (S) | 95 |
|   | | YbCl₃ | 0.5 | 92 | 94 (S) | 79 |
|   | | AlMe₃ | 0.2 | 92 | 89 (S) | 90 |
| 4 | | p-TsOH | 0.3 | 97 | 97 (R) | 77 |
|   | | silica gel | 48 | 97 | 97 (S) | 70 |
|   | | YbCl₃ | 0.3 | 97 | 96 (S) | 84 |
|   | | AlMe₃ | 0.2 | 97 | 69 (S) | 91 |
| 5 | | p-TsOH | 2 | 94 | 90(99)(R) | 68 |
|   | | YbCl₃ | 3 | 94 | 77 (S) | 87 |
|   | | AlMe₃[b] | 0.1 | 94 | 69 (S) | 79 |
| 6 | | p-TsOH | 0.3 | 94 | 94 (R) | 72 |
|   | | AlMe₃[c] | 5 | 94 | 90 (R) | 71 |
| 7 | | p-TsOH | 0.05 | 99 | 99 (R) | 79 |
|   | | silica gel | 48 | 99 | 38 (R) | 45 |
|   | | YbCl₃ | 2.5 | 99 | 57 (R) | 87 |
|   | | AlMe₃ | 0.1 | 99 | 93 (R) | 81 |

Kinetic Resolution of Enol Ester Epoxides Catalyzed by [(R)-BINOL]$_2$-Ti(O$^i$Pr)$_4$ [a]

| entry | substrate | time (h) | conv. (%) | recov'd S.M.(ee%) | epoxide yield (%) | product ee% | $k_{rel}$ [b] ($k_f/k_S$) |
|---|---|---|---|---|---|---|---|
| 1[c] | R=Ph | 1.0 | 50 | 97 (R) | 34 | 90 (R) | >100 |
| 2 | R=p-CH$_3$Ph | 0.5 | 50 | 99 | 34 | 84 (R) | >100 |
| 3 | R=m-CH$_3$Ph | 0.4 | 53[f] | 97 | 36 | 87 | 55 |
| 4 | R=p-ClPh | 0.5 | 52 | 99 | 32 | 87 (R) | >100 |
| 5 | R=p-NO$_2$Ph | 2.2 | 49 | 96 | 39 | 96 (R) | >100 |
| 6 | R=3,5-Me$_2$Ph | 0.6 | 53 | 99 | 35 | 83 | 80 |
| 7 | R=2,6-Me$_2$Ph | 1.7 | 50 | 99 | 37 | 90 | >100 |
| 8 | R=1-Napth. | 0.9 | 52[f] | 98 | 33 | 91 | 91 |
| 9[c] | R=t-Bu | 0.6 | 54 | 97 (R) | 22 | 88 (R) | 43 |
| 10 | R=Me | 1.2 | 68 | 85 (R) |  | 48 (R) | 6 |
| 11[d] |  | 24 | 51[f] | 98 | 33 | 93 | >100 |
| 12 |  | 3.0 | 55 | 99 (R) | 33 | 89 (R) | 49 |
| 13 |  | 6.5 | 54 | 98 (R) | 34 | 80 (R) | 50 |
| 14[e] |  | 68.5 | 63 | 97 (R) | 32 | 71 (R) | 14 |
| 15 |  | 3.0 | 69 | 99 (R) | 30 | 50 (R) | 12 |
| 16[e] |  | 163 | 58 | 54 |  | 38 | 4 |

Figure 23

| n | X | conv. (%) | ee (%) (5) | ee (%) (6) | yield (%) (7) | ee (%) (7) |
|---|---|---|---|---|---|---|
| 1 | CH₂ | 50 | 97 | 90 | 78 | 93 (>99*) |
| 0 | CH₂ | 50 | 91 | 92 | 79 | 92 (>99*) |
| 2 | CH₂ | 54 | 99 | 78 | 83 | 87 (>99*) |
| 3 | CH₂ | 63 | 97 | 71 | 81 | 82 (>99*) |
| 1 | O | 51 | 98 | 93 | 77 | 97 (>99*) |

* the ee's after recrystallization

Asymmetric Epoxidation of Olefins Catalyzed by Ketone 1, using $H_2O_2$ and acetonitrile mixture as the oxidizing agent.
| Entry | Substrate | Yield (%) | ee (%) | Configuration |
|---|---|---|---|---|
| 1 | 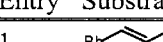 | 84 | 92 | (R,R) |
| 2 | 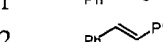 | 77 | 98.7 | (R,R) |
| 3 | 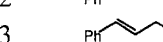 | 74 | 93 | (R,R) |
| 4 | 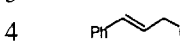 | 55 | 89 | (R,R) |
| 5 |  | 90 | 95 | (R,R) |
| 6 | 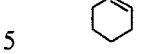 | 75 | 93 | (R,R) |
| 7 |  | 93 | 95 | (R,R) |
| 8 | 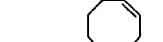 | 76 | 95 | (R,R) |
Figure 25

CATALYTIC ASYMMETRIC EPOXIDATION

CROSS-REFERENCES TO RELATED APPLICATIONS

This application is a Continuation-In-Part of U.S. patent application Ser. No. 09/284,054, filed Apr. 6, 1999 now U.S. Pat. No. 6,348,608, which is a U.S. National Phase Patent Application of PCT Patent Application No. PCT/US97/18310, filed Oct. 8, 1997, which claims the priority benefit of U.S. Provisional Patent Application No. 60/028,009, filed Oct. 8, 1996. This application is also a Continuation-In-Part of U.S. patent application Ser. No. 09/673,335, filed Dec. 4, 2000, now U.S. Pat. No. 6,409,769 which is a U.S. National Phase Patent Application of PCT Patent Application No. PCT/US99/08418, filed Apr. 16, 1999, which claims the priority benefit of U.S. Provisional Patent Application No. 60/082,029, filed Apr. 16, 1998. This application is also a Continuation-In-Part of U.S. patent application Ser. Nos. 09/663,390, filed Aug. 10, 2000 now U.S. Pat. No. 6,369,245 and 09/534,419, filed Mar. 23, 2000, now U.S. Pat. No. 6,384,265 which claim the priority benefits of U.S. Provisional Patent Application Nos. 60/148,904, filed Aug. 13, 1999, and Ser. No. 60/125,687, filed Mar. 23, 1999, respectively. All of the above patent applications are incorporated herein by reference in their entirety.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. CHE-9875497 awarded by National Science Foundation and Grant Nos. GM55704-01 and GM59705-01 awarded by the National Institutes of Health.

FIELD OF THE INVENTION

The present invention is directed to a catalytic asymmetric epoxidation of olefins by contacting an oxidizing agent to a mixture of a cyclic chiral ketone and an olefin.

BACKGROUND OF THE INVENTION

Epoxides are very important chiral building blocks for the synthesis of enantiomerically pure complex molecules. Asymmetric epoxidation of olefins presents a powerful strategy for the synthesis of enantiomerically enriched epoxides. Great success has been achieved in the epoxidation of allylic alcohols, unfunctionalized cis-olefins, and conjugated trisubstituted olefins. However, the epoxidation of trans-olefins bearing no allylic alcohol group with high enantiomeric excess still remains a challenging problem.

Among many other powerful epoxidation methods chiral dioxiranes generated in situ from an oxidizing agent, typically Oxone® (potassium peroxomonosulfate), and a chiral ketone have appeared to be promising reagents for asymmetric epoxidations, particularly for trans-olefins bearing no allylic alcohol groups. Since the first asymmetric epoxidation of olefins with dioxirane were reported in 1984, significant progress has been made in the area. A $C_2$ symmetric cyclic chiral ketone derived from 1,1'-binaphthyl-2,2'-dicarboxylic acid has been used as a catalyst to achieve high enantioselectivity for the epoxidation of trans-4,4'-disubstituted stilbenes. This cyclic chiral ketone, however, is limited to certain substrates.

Therefore, there is a need for an inexpensive, readily available, and general asymmetric epoxidation catalyst which can epoxidize a variety of olefins with high enantioselectivity.

SUMMARY OF THE INVENTION

In general, the present invention is based on enantioselective epoxidation of an olefin by an epoxidizing agent derived from a reaction between an oxidizing agent and a cyclic chiral ketone. Without being bound by any theory, it is believed that a reaction beween the oxidizing agent and the chiral ketone produces a dioxirane that is believed to be the intermediate responsible for the observed enantioselective epoxidation reaction. Thus, the present invention can also be described as contacting the olefin with an epoxidizing agent which is derived from contacting the oxidizing agent with the chiral ketone. However, to reflect a preferred procedure of adding the oxidizing agent to the reaction mixture, the present invention is described herein as contacting the oxidizing agent with an olefin in the presence of the chiral ketone.

In one embodiment of the present invention, the oxidizing agent is derived from a mixture of hydrogen peroxide and a nitrile compound.

The reaction mixture can also include a base. The pH of the reaction mixture is preferably from about pH 5 to about pH 14, more preferably at pH of from about pH 10 to about pH 14, and most preferably from about pH 10 to about pH 12.

In one particular aspect, the present invention provides a method of producing an epoxide from an olefin comprising contacting an oxidizing agent with an olefin in the presence of a chiral ketone under conditions sufficient to produce an epoxide from the olefin.

In another aspect, the present invention provides a method for increasing a relative concentration of at least one stereoisomer of an olefin from the stereoisomer mixture. The method generally involves converting one of the stereoisomers of the olefin to an epoxide at a higher rate than the conversion of the other stereoisomer. The method generally involves contacting an oxidizing agent with a stereoisomer mixture of the olefin in the presence of a chiral ketone described herein. The reaction epoxidizes one of the olefin stereoisomers at a substantially higher rate than the other stereoisomer. This difference in reactivity of stereoisomers results in a relative increase in the concentration of the other olefin stereoisomer.

Yet in another aspect, the present invention provides a method for stereoselectively producing an α-acyloxy carbonyl compound from an enol ester olefin. The method generally involves:

(a) contacting an oxidizing agent with the enol ester olefin in the presence of the chiral ketone described herein under conditions sufficient to stereoselectively produce an enol ester epoxide, and (b) contacting the enol ester epoxide with an acid catalyst under conditions sufficient to stereoselectively produce the α-acyloxy carbonyl compound.

The α-acyloxy carbonyl compound can be produced from the enol ester epoxide with inversion or retention of stereochemistry depending on the acid catalyst used.

BRIEF DESCRIPTION OF THE DRAWINGS

FIGS. 4–7 shows results of asymmetric epoxidation reaction of olefins with various chiral ketones of the present invention;

FIG. 8 shows results of asymmetric epoxidation reaction of various olefins with chiral ketone 6b of FIG. 7;

FIG. 9 shows results of asymmetric epoxidation reaction between trans-stilbene and chiral ketone 1 of FIG. 1 at different reaction time. The reactions were carried out at 0° C. (bath temperature) with substrate (1 eq.), Ketone 1 (1 eq.), Oxone (5 eq.), and NaHCO₃ (15.5 eq.) in CH₃CN-aqueous EDTA (4×10⁻⁴M)(1.5:1, V/V) as in Method A;

FIG. 10 shows the solvent effect on the asymmetric epoxidation reaction of trans-β-methylstyrene with chiral ketones 1 of FIG. 1 and DW-25a of Examples. Reactions in entries 1–24 were carried out with trans-β-methylstyrene (1 mmol), ketone 1 (0.3 mmol), Oxone® (1.38 mmol) in a mixture of 15 mL of organic solvent and 10 mL of 0.05 M Na₂B₄O₇.10H₂O in aqueous EDTA (4×10⁻⁴ M) solution, and the pH was adjusted to 10.5 by using 1.0 M aqueous K₂CO₃ solution. Reaction in entries 25–31 were carried out with trans-β-methylstyrene (0.4 mmol), ketone DW-25a (see Experimental section) (0.02 mmol), Oxone® (0.55 mmol), and K₂CO₃ (2.31 mmol) in organic solvent (6 mL) and buffer (0.05 M Na₂B₄O₇.10H₂O in aqueous EDTA (4×10⁻⁴ M) (4 mL);

FIG. 11 shows the temperature effect on the asymmetric epoxidation reaction of trans-β-methylstyrene with chiral ketone 1 of FIG. 1. All reactions were carried out with trans-β-methylstyrene (1 mmol), Ketone 1 (1 mmol), Oxone® (1 mmol), K₂CO₃ (4.3 mmol), and Bu₄NHSO₄ (0.05 mmol) in 25 mL of CH₃CN—DMM-0.05 M Na₂B₄O₇.10H₂O in aqueous EDTA (4×10⁻⁴ M) solution (1:2:2, V/V); the reactions were stoped after 20 min.

FIG. 12 shows results of the asymmetric epoxidation reaction between various trans-disubstituted olefins with chiral ketone 1 of FIG. 1 and its enantiomer. Ent-1 is enantiomer of chiral ketone 1 shown in FIG. 1. Footnote a: Method A: substrate (1 eq.), ketone (3 eq.), Oxone (5 eq.), and NaHCO₃ (15.5 eq.) in CH₃CN-aqueous EDTA (4×10⁻⁴M) solution (1.5:1, V/V). Method B: substrate (1 eq.), ketone (0.3 eq.), Oxone (1.38 eq.), and K₂CO₃ (5.8 eq.) in CH₃CN-0.05 M Na₂B₄O₇.10H₂O of aqueous EDTA (4×10⁻⁴ M) solution (1:2:2, V/V). Method C: substrate (1 eq.), ketone (0.3 eq.), Oxone (1.38 eq.), and K₂CO₃ (5.8 eq.) in CH₃CN—DMM-0.05 M Na₂B₄O₇.10H₂O of aqueous EDTA (4×10⁻⁴M) solution (1:2:2, V/V). The reactions were stopped after 30 min for 20° C., 1.5 h for 0° C., and 2 h for −10° C. Footnote b: 0.2 eq. of ketone was used.

FIG. 13 shows results of the asymmetric epoxidation reaction between various tri-substituted olefins with chiral ketone 1 of FIG. 1 and its enantiomer. Methods are the same as in FIG. 12.

FIG. 16 shows regio-selectivity of the asymmetric epoxidation reaction between various dienes with chiral ketone 1 of FIG. 1. Footnote a: Reactions were carried out at 0° C. with 1.0 eq. diene, 0.2–0.3 eq. ketone, 1.12–1.38 eq. Oxone®, and 5.8 eq. K₂CO₃ in CH₃CN—DMM-0.05 M Na₂B₄O₇.10H₂O of aqueous EDTA (4×10⁻⁴M) solution (1:2:2, v/v). Oxone was added over 1.5 h unless otherwise stated and the reactions were stopped immediately thereafter. Footnote b: The number in parentheses refers to the yield of the minor epoxide. Footnote c: The number in parentheses refers to the % ee of the minor epoxide.

FIG. 23 shows the results of kinetic resolution of various enol ester epoxides catalyzed by [(R)—BINOL]₂—Ti(O$^i$Pr)₄. Footnote a: All reactios were carried out with substrate (0.5 mmol) and catalyst (5 mol %) in solvent (2 mL) at 0° C. unless otherwise noted. Footnote b: The relative rate was calculated using the equation $k_{rel}=k_f/k_s=\ln[(1-C)(1-ee)]/\ln[(1-C)(1+ee)]$ where C is the conversion and ee is the percent enantiomeric excess of the recovered starting material (see Kagan et al., *Top. Stereochem*. 1988, 18, 249). Footnote c: 2.5 mol % catalyst used. Footnote d: 10 mol % catalyst used. Footnote e: 20 mol % catalyst used. For entry 16, the reaction was carried out at room temperature. Footnote f: The conversion was calculated applying the ee's of the recovered starting material and the product the following equation: ee(SM)/ee(product)=C/(1−C).

FIG. 25 shows the results of asymmetric epoxidation of various olefins catalyzed by chiral ketone 1 of FIG. 1 using an oxidizing agent that is derived from a mixture of hydrogen peroxide and acetonitrile.

DEFINITIONS

Figure 1:
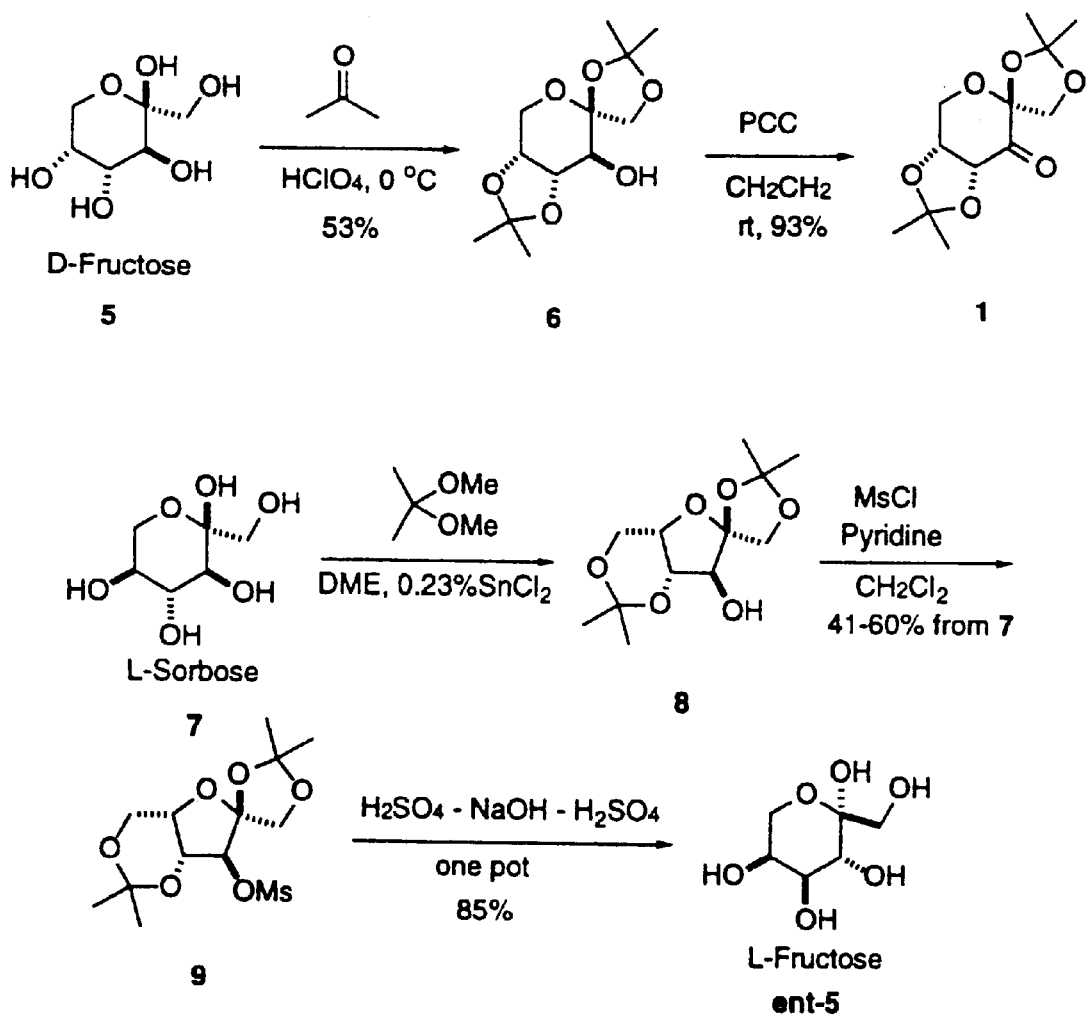
FIG. 1 illustrates a synthetic scheme for a preparation of a ketone derived from D-fructose which is a useful catalyst for the asymmetric epoxidation of olefins as described in the present invention and a synthetic scheme for a preparation of L-fructose from L-sorbose.

"Alkyl" refers to straight or branched aliphatic hydrocarbons. Alkyl groups optionally can be substituted with one or more substituents, such as aryl and cycloalkyl. Exemplary alkyl groups include methyl, ethyl, i-propyl, propy, n-butyl, t-butyl, n-pentyl, hexyl, heptyl, octyl, and the like.

The term "alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Haloalkyl" refers to an alkyl moiety as defined herein in which one or more hydrogen atoms have been replaced with same or different halides. Exemplary haloalkyls include $-CH_2Cl$, $-CH_2F$, $-CF_3$, $-CH_2CF_3$, $-CH_2CCl_3$, and the like. Moreover, haloalkyl also includes perfluoroalkyls in which all alkyl hydrogen atoms are replaced by halides.

"Heteroalkyl" refers to an alkyl moiety as defined herein which comprises one or more heteroatom-containing substituents and/or heteroatoms. Preferably, the heteroatom is selected from the group consisting of N, O, P, and S. Exemplary heteroatom-containing substituents include alkoxides (i.e., ethers), hydroxide, optionally alkylated amines, carbonyls (e.g., ketones, aldehydes, amides, esters, carboxylic acids, thioethers, sulfoxides, sulfones, thiol, and the like.

The terms "halide," "halo" and "halogen" are used interchangeably herein and refer to fluoro, chloro, bromo, or iodo, preferably fluoro or chloro, substituent.

The term "cycloalkyl" refers to a saturated monovalent cyclic hydrocarbon radical of three to eight ring carbons. The cycloalkyl may be optionally substituted independently with one, two, or three substituents selected from alkyl, haloalkyl, halo, nitro, cyano, aryl and the like. Exemplary cycloalkyls include, cyclopropyl, cyclobutyl, cyclopentyl, cyclohexyl, and the like.

The terms "inversion" and "inversion of stereochemistry" are used interchangeably herein and refer to a process in which the product has an opposite stereochemical configuration relative to the starting material. For example, in an acid catalyzed rearrangement reaction in which the α-acyloxy group of an α-acyloxy carbonyl compound having an opposite stereochemical configuration relative to the stereochemistry of the starting epoxide group. This is schematically illustrated in the conversion of compound 3 to compound 8 in FIG. 20. Preferably, when methods of the present invention result in inversion of stereochemistry at least about 75% of the product results from inversion of stereochemistry, more preferably at least about 80%, still more preferably at least about 90%, yet still more preferably at least about 95%, and most preferably substantially all of the product has inversion of stereochemistry.

The terms "retention" and "retention of stereochemistry" are used interchangeably herein and refer to a process in which the product has the same stereochemical configuration as that of the starting material. For example, in an acid catalyzed rearrangement reaction in which the α-acyloxy group of an α-acyloxy carbonyl compound having a same stereochemical configuration relative to the stereochemistry of the starting epoxide group. This is schematically illustrated in the conversion of compound 3 to compound 6 in FIG. 20. Preferably, when methods of the present invention result in retention of stereochemistry at least about 75% of the product results from retention of stereochemistry, more preferably at least about 80%, still more preferably at least about 90%, yet still more preferably at least about 95%, and most preferably at least about 99%.

The terms "enantioselective" and "stereoselective" refer to a process which results in the production of a product having predominantly one particular stereochemistry at the reaction center, i.e., carbon atom(s) which undergo a chemical reaction during the process. It should be appreciated that while the starting material may have other chiral centers other than the reacting site, the terms "enantioselective" and "stereoselective" refer only to the stereochemical center resulting from the given reaction.

The terms "enantiomeric excess" and "stereoisomeric excess" refer to a process in which the product has predominantly one particular stereochemistry at the reaction center, i.e., carbon atom(s) which undergo a chemical reaction during the process. Preferably, methods of the present invention results in the product having an enantiomeric or stereoisomeric excess of at least about 12% ee, more preferably at least about 80% ee, still more preferably at least about 90% ee, and most preferably at least about 95% ee.

"Heterocyclyl" refers to a saturated cyclic moiety of 3 to 8 ring atoms in which one or more, preferably one or two, ring atoms are heteroatoms selected from N, O, or $S(O)_n$ (where n is an integer from 0 to 2), the remaining ring atoms being C. Preferably, the heteroatom is O. In addition, one or two C atoms of the heterocyclyl can also be substituted with carbonyl oxygen atoms. The heterocyclyl ring can be optionally substituted with one or more, preferably one, two, or three, substituents. Exemplary substituents for heterocyclyl moiety include alkyl, haloalkyl, heteroalkyl, aryl, halo, acyl, cycloalkyl, and the like. More specifically the term heterocyclyl includes, but is not limited to, tetrahydropyranyl, tetrahydrofuranyl, 1,3-dioxolanyl, 1,4-dioxonyl, 1,3-dioxonyl, and the derivatives thereof.

Unless the context requires otherwise, the terms "stereoisomeric mixture" and "stereochemical mixture" are used interchangeably herein and refer to a relative ratio of each stereoisomer or enantiomer present in the starting material, e.g., prior to a kinetic resolution. Furthermore, when these terms are used without any value, they refer to the fact that the starting material contains more than one stereoisomer or enantiomer.

The terms "stereoisomerically enriched mixture" and "enantiomerically enriched mixture" of a compound refer to a stereoisomeric and enantiomeric mixture of a compound, respectively, where the relative ratio of each stereoisomer and enantiomer is different than the starting material, e.g., prior to a reaction.

An "enol ester epoxide" refers to an epoxide compound having an acyloxy substituent on one of the carbon atoms of the epoxide ring, i.e., a compound having the formula:

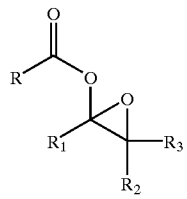

An "α-acyloxy carbonyl compound" refers to a carbonyl compound, e.g., a ketone or aldehyde, having an acyloxy substituent α to the carbonyl functionality, i.e., a compound having the formula:

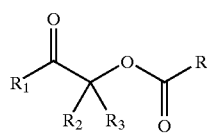

The term "kinetic resolution" refers to a process or a method of increasing the concentration of one particular enantiomer or stereoisomer of the starting material or the product. Such process is preferably affected by converting, i.e., transforming, one particular enantiomer or stereoisomer of the starting material to a different compound at a rate faster than conversion of the other enantiomer or stereoisomer.

"Carbohydrate" refers to a sugar molecule or its derivative. Carbohydrate can be monosaccharide or polysaccharide. Exemplary carbohydrates include glucose, fructose, maltose, lactose, mannose, sorbose, ribose, xylose, rhamnose, galactose, talose, arabinose, gulose, sucrose, cellobiose, cellulose, maltonic acid, heparin, chondroitin sulfate, amylose and amylopectin.

"Protecting group" refers to a moiety that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1–8 (John Wiley and Sons, 1971–1996), which are incorporated herein by reference in their entirety. Representative hydroxy protecting groups include alkyls, acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom to which it is attached.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

"Olefin" refers to a compound having at least one alkene functionality, i.e., a double bond between two carbon atoms. An olefin can have more than one double bond. If more than one double bond is present on the olefin, the double bonds can be conjugated or non-conjugated. Moreover, the olefin can be monosubstituted, di-substituted, tri-substituted or fully substituted. By substituted, it is meant that the olefinic carbon atom is attached to an atom other than hydrogen atom. For example, the olefinic carbon can be substituted with a halogen atom, silicon atom, another carbon atom, oxygen atom, sulfur atom and/or a metal atom such as lithium, sodium or magnesium. Preferably, the olefin is at least a di-substituted olefin. The di-substituted olefin can be geminal, cis-, or trans-substituted olefin. Preferably the di-substituted olefin is a trans-substituted olefin. Generally for olefins having at least three substituent groups, trans-olefin designation refers to the trans relationship between the larger substituents attached to the two different olefinic carbon atoms, whereas cis designation refers to the cis relation between the larger substituents. In addition to cis- and trans- notation an "E" or "Z" notation can used to denote the relative priority of the substituent groups. E- and Z-notations denoting the stereoisomers of alkenes are well known to one of ordinary skill in the art. Preferably, the olefin is E-stereoisomer (i.e., trans-olefin).

"Stereoisomer" refers to any group of compounds having the same molecular formula and the same linkages of bonded atoms but differ in their spatial arrangement. Exemplary stereoisomers includes geometric isomers (e.g., cis- or trans-olefins) and optical isomers (e.g., diastereomers and enantiomers).

Unless otherwise stated, the term "pH" in the present invention refers to an apparent pH.

As used herein, the terms "those defined above" and "those defined herein" when referring to a variable incorporates by reference the broad definition of the variable as well as preferred, more preferred and most preferred definitions, if any.

DETAILED DESCRIPTION

Epoxidation reactions are used in many industrial processes including for producing chiral building blocks for the synthesis of enantiomerically pure complex molecules such as polymers, surfactants, pesticides, insecticides, insect hormones, insect repellants, pheromones, food flavoring, and drugs. The stereochemistry of a molecule is important in many of the properties of the molecule. For example, it is well known that physiological properties of drugs having one or more chiral centers, i.e., stereochemical centers, depend on the stereochemistry of a drug's chiral center. In addition, properties of a polymer containing a chiral monomeric unit depend on the enantiomeric purity of the monomer. Thus, it is advantageous to be able to control the stereochemistry of a chemical reaction. Since an epoxide serve as an intermediate or a starting material for many chemical compounds, it is especially desirable to be able to control the stereochemistry of the epoxide formation.

Moreover, stereoselective epoxidation reaction can also be used for kinetic resolution of an olefinic compound. For example, by epoxidizing a one stereoisomer at a higher rate than the other, the resulting product will comprise a higher amount of one particular stereochemical epoxide and one particular olefinic compound.

As stated above, stereoselectively produced epoxides are useful in the synthesis of other stereoisomerically enriched compounds, e.g., α-acyloxy carbonyl, vic-diol (i.e., 1,2-diol), as well as other products resulting from transformation of the epoxide or other functional group that is present on the epoxide compound.

Some aspects of the present invention are based on a stereoselective epoxidation of an olefin by contacting an oxidizing agent with the olefin in the presence of a chiral ketone. Preferably, the cyclic chiral ketone is of the formula:

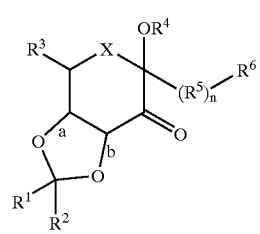

I or a derivative thereof which is capable of converting to the chiral ketone of Formula I under the reaction conditions, wherein bonds a and b are of cis-configuration relative to each other;

n is 0 or 1;

X is selected from the group consisting of O and $CR^7R^8$, where $R^7$ and $R^8$ is independently selected from the group consisting of hydrogen, alkyl, haloalkyl and heteroalkyl, or $R^7$ together with $R^4$ together with the atoms to which they are attached to form an optionally substituted heterocyclyl;

each of $R^1$ and $R^2$ is independently selected from the group consisting of hydrogen or alkyl, or $R^1$ and $R^2$ together with atoms to which they are attached to form a cycloalkyl;

$R^3$ is selected from the group consisting of hydrogen and $OR^9$, where $R^9$ is a hydroxyl protecting group or an aryl group;

$R^5$ is alkylene;

$R^4$ is hydrogen or a hydroxy protecting group; and $R^6$ is hydrogen, alkyl, or —$OR^a$, where $R^a$ is hydrogen or a hydroxy protecting group; or $R_4$ and $R^6$ together with the atoms to which they are attached to form an optionally substituted heterocyclyl.

As stated, the scope of the present invention also includes a derivative of Formula I which is capable of converting to the chiral ketone of Formula I under the reaction conditions. Such derivatives include enols, imines, where the carbonyl group is replaced by an imine group (e.g., =NR, where R is hydrogen or a hydrocarbon), solvated forms, including hydrated forms, salts thereof and other derivatives known to one skilled in the art. In general, the solvated forms, including hydrated forms, are equivalent to unsolvated forms and are encompassed within the scope of the present invention. Furthermore, the present invention also includes all salts of compounds of Formula I along with other derivatives and all stereoisomers whether in a pure chiral form or a racemic mixture or other form of mixture.

Referring to compound of Formula I, preferably, one of $R^4$ and $R^6$ or $R^4$ and $R^7$ together with the atoms to which they are attached form an optionally substituted heterocyclyl, more preferably five or six-membered heterocyclyl.

In one particular embodiment, $R^3$ is hydrogen.

Preferably, X is O or $CH_2$.

In another embodiment, the chiral ketone is of the formula:

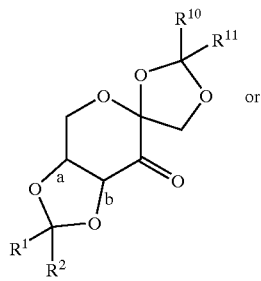

IIA or

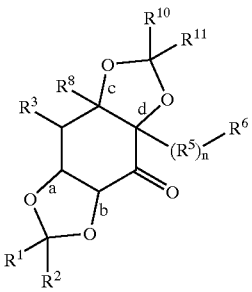

IIB or a derivative thereof which is capable of converting to the chiral ketone of Formula I under the reaction conditions, wherein a, b, n, $R^1$, $R^2$, $R^3$, $R^5$, $R^6$ and $R^8$ are those defined above;

bonds c and d are cis-configuration relative to each other; and $R^{10}$ and $R^{11}$ are independently hydrogen or alkyl; or $R^{10}$ and $R^{11}$ together with atoms to which they are attached to form a cycloalkyl. Preferably, the chiral ketone is of Formula IIA.

In one particular embodiment, each of $R^1$ and $R^2$ is independently hydrogen or $C_1$–$C_4$ alkyl or $R^1$ and $R^2$ together with the atoms to which they are attached to form cyclopentyl, cyclohexyl or cycloheptyl.

Preferably, $R^{10}$ and $R^{11}$ are $C_1$–$C_4$ alkyl or $R^{10}$ and $R^{11}$ together with the atoms to which they are attached to form cyclopentyl, cyclohexyl or cycloheptyl. More preferably, $R^{10}$ and $R^{11}$ are $C_1$–$C_4$ alkyl or $R^{10}$ and $R^{11}$ together with the atoms to which they are attached to form cyclopentyl, cyclohexyl or cycloheptyl.

Exemplary compounds of Formula I include, but are not limited to:

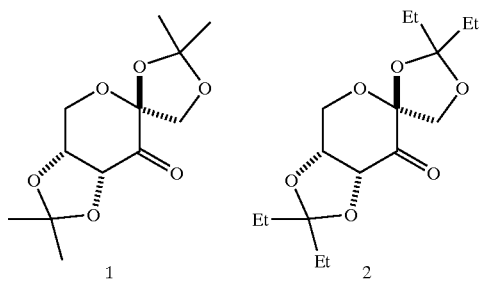

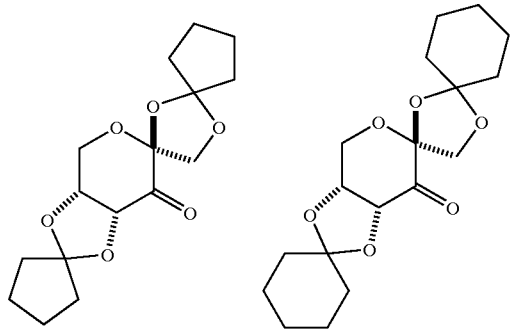

-continued
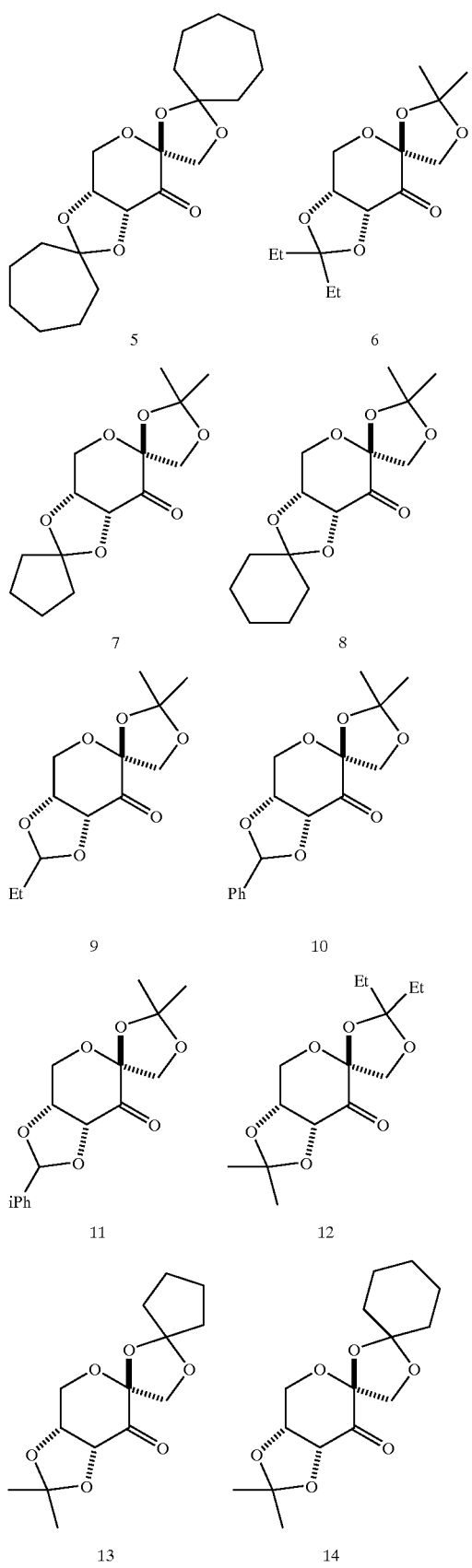
-continued
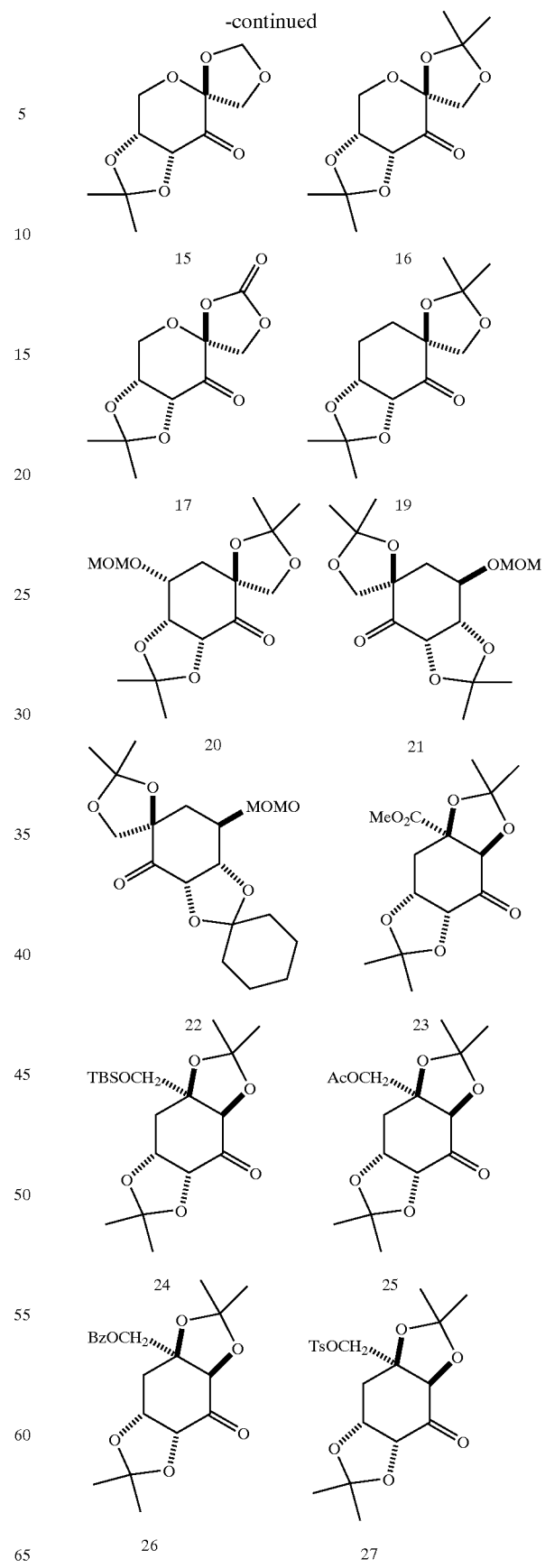

-continued
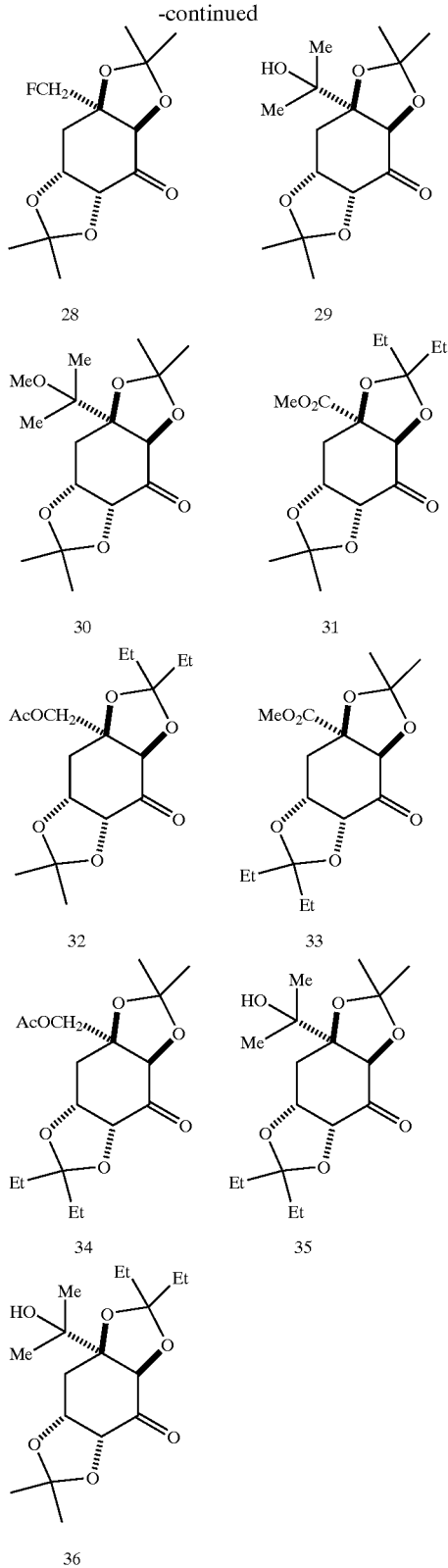
28 29 30 31 32 33 34 35 36
stereoisomers, preferably enantiomers, and derivatives thereof
Specific examples of preferred chiral ketones of Formula I include, but are not limited to:
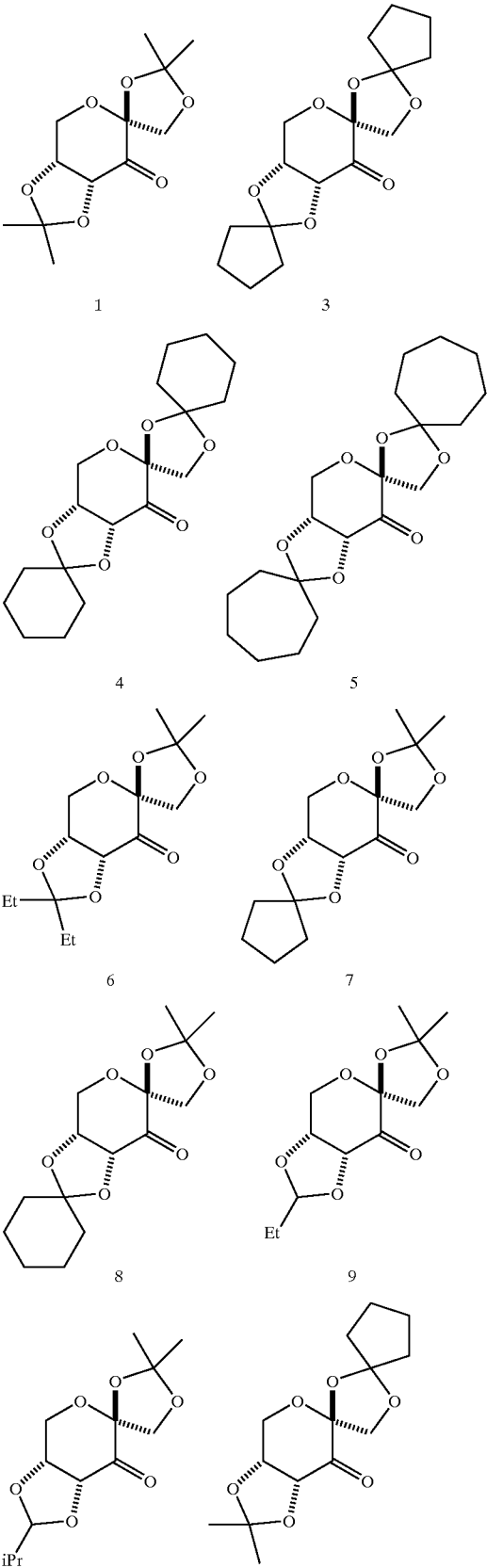
1 3 4 5 6 7 8 9 11 13

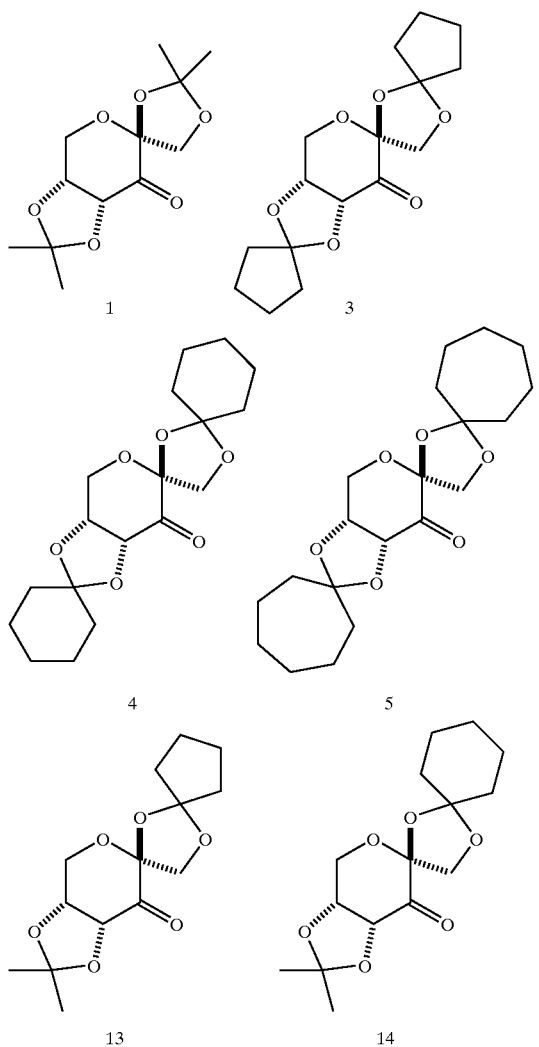

enantiomers, and derivatives thereof.

Specific examples of more preferred chiral ketone of Formula I include, but are not limited to:

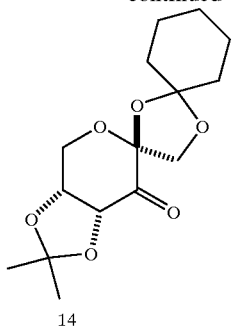

enantiomers, and derivatives thereof specific example of still more preferred chiral ketone of Formula I is of the formula:

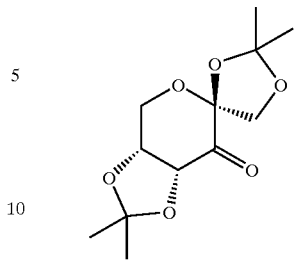

III an enantiomer, and derivatives thereof

One aspect of the present invention provides a method for asymmetrically epoxidizing olefins using a chiral ketone and an oxidizing agent. A chiral center (i.e., stereochemical center, or stereogenic center) is, of course, an atom to which four different groups are attached; however, the ultimate criterion of a chiral center is nonsuperimposability on the mirror image. Facially selective, stereoselective, enantioselective or asymmetric synthetic reactions are those in which one of a set of stereoisomers is formed exclusively or predominantly.

In one embodiment of the present invention, a method for asymmetrically epoxidizing an olefin comprises contacting an oxidizing agent with an olefin in the presence of a chiral ketone of Formula I under conditions sufficient to produce an epoxide. In one particular embodiment, one isomer of the epoxide is produced in at least about 50 percent excess over the other isomer. Preferably, one isomer of the epoxide is produced in at least about 80 percent excess over the other isomer. More preferably, one isomer of the epoxide is produced in at least about 90 percent excess over the other isomer. Even more preferably, one isomer of the epoxide is produced in at least about 95 percent excess over the other isomer.

Without being bound by a theory, it is believed that contacting an oxidizing agent to a chiral ketone produces a chiral dioxirane. In general, the chiral dioxirane is generated and used in situ by contacting (i.e., reacting) a chiral ketone with an oxidizing agent. It is also believed that the reaction between an olefin and the dioxirane provides an epoxide and regenerates the chiral ketone; therefore, the chiral ketone can be used as a catalyst. Thus, less than one equivalent of the chiral ketone, relative to the olefin, can be used in the present invention, i.e., the same molecule of chiral ketone can be used more than once in epoxidizing an olefin. The average number of epoxidation of olefins produced by a ketone molecule is known as a catalytic turn-over number, or simply a turn-over number. Preferably, the ketones of the present invention have a turn-over number of at least about 3, more preferably at least about 50 and most preferably at least about 100. Moreover, since the ketones have such a high turn-over number, the amount of the ketones required to epoxidize a given amount of olefin can be less than the stoichiometric amount, i. e., one equivalent, of the olefin. Preferably no more than about 0.3 equivalents of ketone is used to epoxidize olefins, more preferably no more than about 0.05 equivalents, and most preferably no more than about 0.01 equivalents.

A chiral ketone of Formula I can be derived from any appropriate starting material such as a carbohydrate, carvone, inositol, and quinic acid. In one particular embodiment of the present invention, the chiral ketone of Formula I is derived from a carbohydrate. Preferably, the chiral ketone is derived from an oxidation of an unprotected hydroxy group of a carbohydrate compound having at least one protected hydroxy group. Preferably, the protecting groups for protected hydroxy groups are selected from the group consisting of silyl ethers, ethers, acetals, ketals, esters, ortho esters, sulfonates, phosphates and mixtures thereof. The protecting groups for two or more hydroxy groups of the carbohydrate or its derivative can be interconnected. For example, an acetonide group protecting 4,5-hydroxy groups of fructose can be considered to be "two interconnected acetal protecting groups" since they protect two hydroxy groups on the fructose. The oxidation of a hydroxy group of a carbohydrate to form a carbonyl group is well known to one skilled in the art. See Mio et al. *Tetrahedron* 1991, 47, 2133–2144. For example, pyridinium chlorochromate (PCC), pyridinium dichromate (PDC), Swern oxidation condition or other oxidizing conditions can be used to oxidize a hydroxy group of a carbohydrate or its derivative to a ketone compound of the present invention. Preferably, the carbohydrate is selected from the group consisting of fructose, sorbose, arabinose, mannose, and glucose.

More preferably, the carbohydrate is selected from the group consisting of (D)-fructose, (L)-fructose, (L)-sorbose, (L)-arabinose, and (D)-arabinose.

Although the actual epoxidizing agent (e.g., dioxirane) can be generated in a separate reaction prior to contacting with an olefin, it is more advantageous to combine the chiral ketone and the olefin in a single reaction mixture and generate the dioxirane in situ by adding an oxidizing agent to the reaction mixture. While the present invention is described in reference to dioxirane as being the actual epoxidizing agent, the scope of the present invention is not limited to such. Generally, any reactive species which stereoselectively generates the epoxide from the reaction mixture provided herein is within the scope of the present invention. However, for brevity and consistancy throughout this disclosure, the reactive species is described as being a dioxirane of the chiral ketone.

Depending on the nature of the oxidizing agent, it is added as a solution or a solid to the reaction mixture comprising the chiral ketone and the olefin. In this manner, the chiral ketone can be used in an amount less than the stoichiometric amount relative to the amount of the olefin. It should be appreciated that in situ generation of dioxirane from a ketone generally requires the oxidizing agent to be more reactive towards the ketone than the olefin to avoid competing oxidation of olefin by the oxidizing agent. However, when the reactivity of the oxidizing agent with the olefin is similar or greater than with the ketone then one method of providing a higher amount of reaction between the oxidizing agent and the ketone to generate the dioxirane is to use the ketone in an amount substantially more than the amount of the olefin. In these cases, preferably the amount of ketone used is at least about 3 times more than the amount olefin, more preferably at least about 5 times, and most preferably at least about 10 times.

Any oxidizing agent capable of providing dioxiranes from a corresponding ketone can be used in the present invention. However, for economic reasons a relatively inexpensive oxidizing agents such as peracids, hydrogen peroxide, sodium hypochlorite, potassium peroxomonosulfate, sodium perborate and hypofluoride (HOF) are preferred. Non-organic oxidizing agents (i.e., a compound that does not contain any carbon atom) are particularly preferred as these oxidizing agents and their reaction products can be easily removed from the reaction mixture by a simple aqueous extraction.

The amount of oxidizing agent used in the present invention depends on a variety of factors including the reactivity of the ketone, olefin, and the decomposition rate of the oxidizing agent. Typically, the amount of an oxidizing agent used is at least about 1 times the amount of the ketone, preferably at least about 9 times, and more preferably at least about 100 times. In another embodiment of the present invention, the amount of an oxidizing agent used is less than about 10 times the amount of the olefin, and more preferably less than about 3 times. However, it should be appreciated that the present invention is not limited to these particular amounts of the oxidizing agent.

In one embodiment, the oxidizing agent is potassium peroxomonosulfate.

In another embodiment, the oxidizing agent is derived from contacting hydrogen peroxide with a nitrile compound. In this embodiment, generally from about 1 equiv. to about 10 equiv. of hydrogen peroxide is used, preferably from about 1 equiv. to about 5 equiv., and more preferably from about 3 equiv. to about 5 equiv. However, the present invention is not limited to these particular amounts of hydrogen peroxide. Without being bound by any theory, it is believed that contacting hydrogen peroxide with a nitrile compound (e.g., $R_{12}$—CN) generates the imidoperacid of the formula:

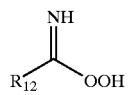

It is believed that this imidoperacid reacts with the ketone to generate the corresponding dioxirane which then epoxidizes the olefin to produce the corresponding epoxide. While the present invention is described in reference to imidoperacid as being the active agent in reacting with the chiral ketone, the scope of the present invention is not limited to such. Generally, any reactive species which is produced in reaction between hydrogen peroxide and the nitrile compound that reacts with the chiral ketone of Formula I to ultimately produce the epoxide from the olefin is within the scope of the present invention. However, for brevity and consistency throughout this disclosure, the reactive oxidative species that is generated from the reaction between hydrogen peroxide and the nitrile compound is described herein as being an imidoperacid.

The nitrile compound can be any compound containing a nitrile functional group (i.e., —CN functional group). Preferably, the nitrile compound does not contain other functional group which may react with other components of the reaction mixture. More preferably, the nitrile compound is of the formula $R_{12}$—CN, where $R^{12}$ is $C_1$–$C_{10}$ alkyl, $C_3$–$C_{10}$ cycloalkyl, $C_6$–$C_{20}$ aryl, $C_7$–$C_{21}$ aralkyl. Preferably $R_{12}$ is $C_1$–$C_6$ alkyl or $C_6$–$C_{15}$ aryl, an more preferably $R_{12}$ is methyl, ethyl, or phenyl (i.e., $R_{12}$—CN is acetonitrile, propionitrile and benzonitrile, respectively). Most preferred nitrile is acetonitrile.

The nitrile compound can be used as a solvent or it can be used as a reagent. When using the nitrile compound as a reagent, typically from about 1 equiv. to about 20 equiv., relative to the amount of olefin, is used. Preferably, from about 1 equiv. to about 10 equiv., relative to the amount of olefin, is used, and more preferably from about 2 equiv. to about 4 equiv.

It should be appreciated that other activators can be used in addition to or in place of the nitrile compound. Exemplary activators which are useful include diimides such as 1,3-dicyclohexylcarbodiimide (DCC); isocyanates; chloroformates cyanate, carbonyl bitriazoles, carbonyldiimidazoles, acetals, ortho esters, orthocarbonates, acid chlorides, anhydrides, aldehydes, formamide, benzeneseleninic acid, Vilsmeier reagent, phosphinic anhydrides and other phosphorus electrophiles, and organosulfonic acids and derivatives thereof.

Other oxidizing agents capable of producing an imidoperacid from the corresponding nitrile compound can also be used. However, for economical reasons, both in terms of the cost and purification process, hydrogen peroxide is the preferred oxidizing agent. Exemplary oxidizing agents which can be used in place of hydrogen peroxide include, but are not limited to, organic oxidizing agents and inorganic oxidizing agents, such as sodium percarbonate. Non-organic oxidizing agents (i.e., a compound that does not contain any carbon atom) are particularly preferred as these oxidizing agents and their reaction products can be easily removed from the reaction mixture by a simple aqueous extraction.

The amount of hydrogen peroxide used in the present invention depends on a variety of factors including the reactivity of the ketone, the olefin, and the nitrile compound. Typically, however, the amount of hydrogen peroxide used is at least about 1 equiv. relative to the amount of the ketone, preferably at least about 9 equiv., and more preferably at least about 100 equiv. In a particular embodiment of the present invention, the amount of hydrogen peroxide used is less than about 10 equiv. relative to the amount of the olefin, preferably less than about 3 equiv., and more preferably about 1 equiv. However, it should be appreciated that the present invention is not limited to these particular amounts of hydrogen peroxide.

As shown on FIG. 9, the reaction time affects both the yield of the epoxide as well as the enantiomeric excess of the epoxide produce. Thus, while a longer reaction period provides higher yield of the epoxide, the enantiomeric excess begins decrease after awhile. Therefore, obtaining a maximum yield of the epoxide while maintaining a sufficient level of enantiomeric excess requires a compromise between the two diametrically opposed results. Preferably, the reaction time is from about 0.1 h to about 24 h, more preferably from about 0.1 h to about 8 h, and most preferably from about 0.1 h to about 3 h. However, it should be appreciated that the present invention is not limited to these particular reaction times.

Figure 2:
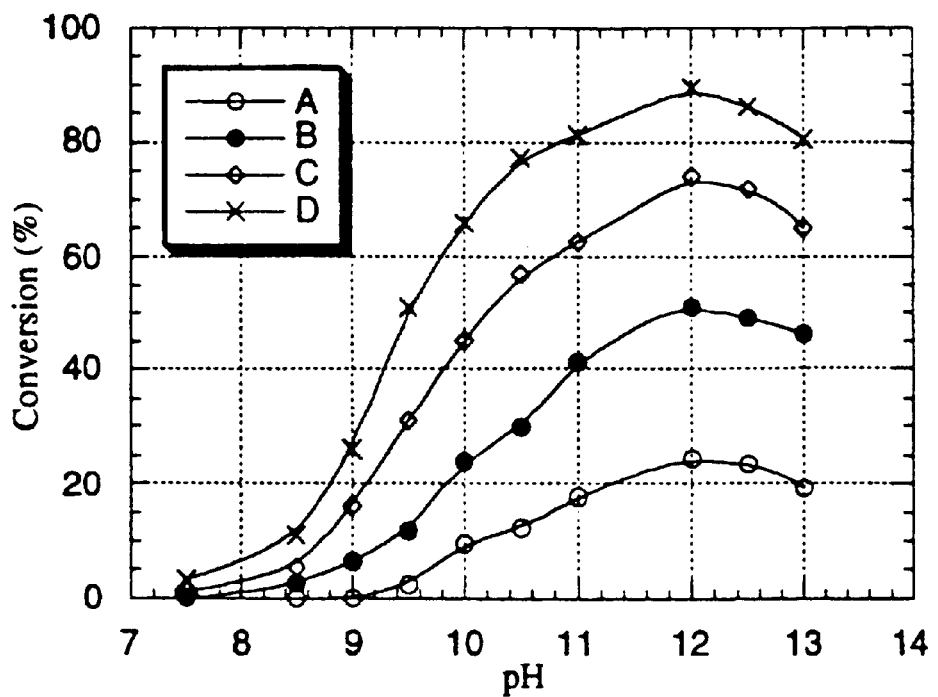
FIG. 2 is a plot of % conversion of trans-β-methylstyrene against pH of the epoxidation reaction using 3 equivalents of acetone as the catalyst in H₂O—CH₃CN (1:1.5, V/V) solvent system at different time intervals.

The pH is also an important factor for the epoxidation with dioxiranes generated in situ. In some cases, generally higher pH results in more rapid decomposition of the dioxirane and/or the oxidizing agent, which leads to the decrease in epoxidation efficiency. For this reason, most non-asymmetric epoxidations are usually carried out at pH 7–8. In some cases, the optimal pH is within a narrow window of 7.8–8.0. As shown in FIG. 2, some epoxidations are more effective at a higher pH. Lines A, B, C and D in FIG. 2 represent samples taken at a reaction time of 0.5 h, 1.0 h, 1.5 h and 2.0 h, respectively. In all cases, the optimal pH is about 12 for epoxidation of methylstyrene with acetone as a catalyst.

Figure 3:
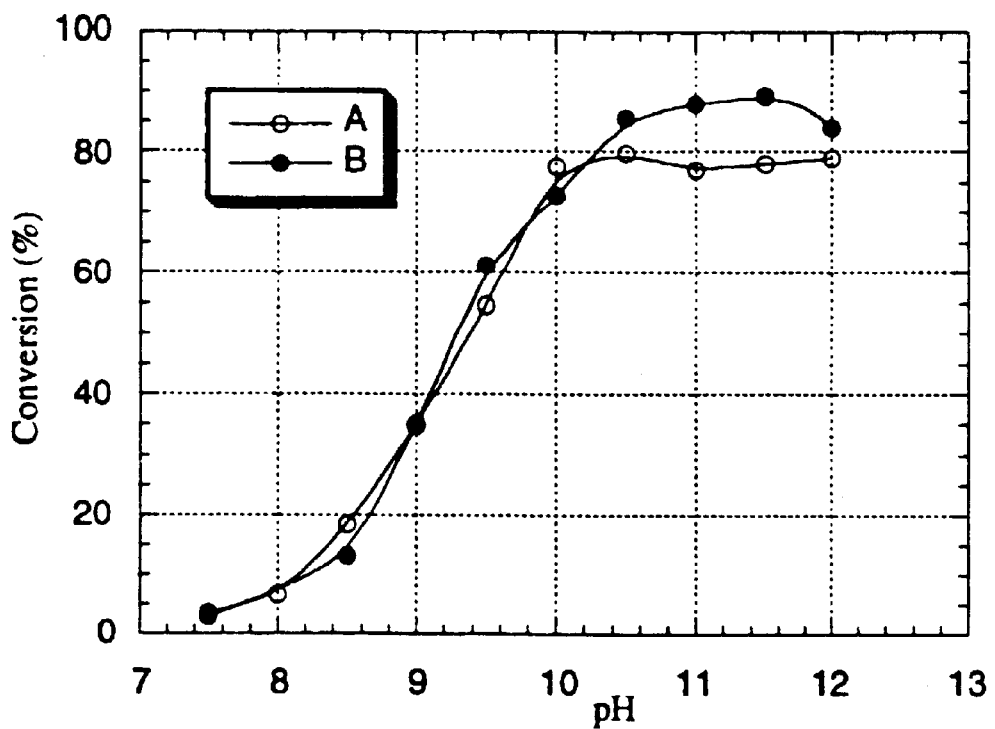
FIG. 3 is a plot of % conversion of trans-β-methylstyrene against pH of the epoxidation reaction using 20 mol % of ketone 1 at 0° C. at 1.5 h reaction time.
Figure 4:
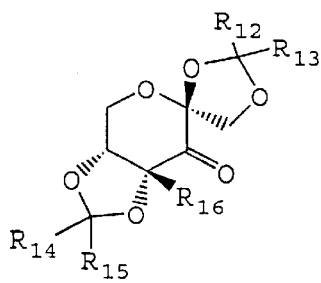
Figure 6:
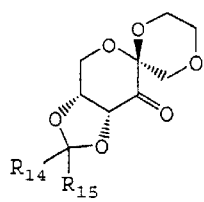
Figure 7:
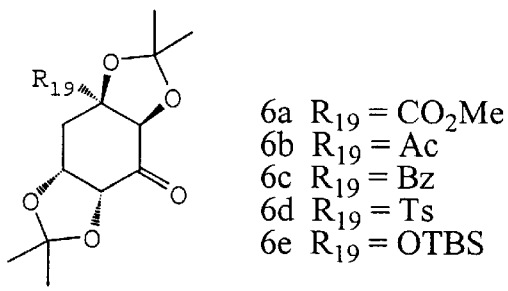

In general, it has been found that higher pH generally provides a higher conversion rate of the olefin to the epoxide (i.e., higher yield of epoxides from olefins) and higher catalytic efficiency (i.e., higher turn-over number). As shown in FIG. 3, the pH has a profound effect on the amount of epoxide produced by the methods of the present invention. In FIG. 3, line A represents a reaction solvent system comprising 1:1.5, V/V, of $H_2O$—$CH_3CN$ and line B represents a reaction solvent system comprising 2:1:2, V/V, of $H_2O$—$CH_3CN$—DMM. In certain cases, the production of epoxides from olefins increased more than 10 fold from a lower pH (7–8) to a higher pH (>10) while maintaining a high enantioselectivity (90–92% ee). In addition, the amount of oxidizing agent can be reduced significantly. The optimal pH range is broad, which increases the utility of the present invention to a wide variety of olefins. Preferably, the pH is at least about 5, more preferably at least about 8, still more preferably at least about 10. Even more preferably the pH is from about 5 to about 14, yet even more preferably from about 10 to about 14, and most preferably from about 10 to about 12. The pH of the reaction solution can be conveniently achieved by adding sufficient amount of base to maintain the pH at the desired level. The base can be added separately, it can be added to the solution containing the ketone, or it can be added to the solution containing the oxidizing agent. Alternatively, a solid mixture of the base and oxidizing agent can be added to the reaction mixture. Preferably the base is selected from the group consisting of hydroxides, carbonates, bicarbonates, borates and phosphates. More preferably the base is selected from the group consisting of potassium carbonate, potassium bicarbonate, lithium carbonate, lithium bicarbonate, sodium carbonate, sodium bicarbonate, calcium carbonate, sodium borate, sodium phosphate, potassium phosphate, lithium hydroxide, sodium hydroxide, potassium hydroxide, magnesium hydroxide and calcium hydroxide, most preferably the base is selected from the group consisting of potassium carbonate, potassium bicarbonate, sodium bicarbonate, sodium carbonate, sodium hydroxide, sodium borate, sodium phosphate, potassium phosphate and potassium hydroxide. Alternatively, the desire pH of the reaction can be more easily maintained by using a buffer solution.

Another factor which may determine the yield of epoxide and/or enantioselectivity of the reaction is the solvent system used. Typically, any organic solvent can be used for the present invention. Exemplary solvents include, nitriles such as acetonitrile and propionitrile, dimethoxymethane (DMM), dimethoxyethane (DME), ethers such as tetrahydrofuran (THF), dichloromethane, chloroform, ethyl acetate, hexane, benzene, toluene, xylenes, dioxane, dimethyl formamide (DMF), pentane, alcohols including, but not limited to, methanol, ethanol and i-propyl alcohol, and mixtures thereof.

Preferably, the solvent is selected from the group consisting of acetonitrile, DMM, DME, DMF, dioxane and mixtures thereof. In certain cases, a mixture of solvents provides higher yield and/or enantioselectivity, for example, a mixture of $CH_3CN$ and DMM is particularly useful.

In another embodiment of the present invention, a mixture of organic solvent and aqueous solution is used as a reaction solution. As FIG. 10 shows, a wide variety of solvents can be used for the present invention. Percentage of enantiomeric excess (% ee), which is a measure of enantioselectivity, is equal to % of one enantiomer (e.g. stereoisomer)–% of the other enantiomer. Thus for example, if the reaction produces (R,R) and (S,S) epoxides in 99% and 1%, respectively, the enantiomeric excess percentage (% ee) will be 98%. Preferably, the methods of the present invention provides asymmetric epoxidation of olefins in at least about 50 % ee, more preferably at least about 80 % ee, and most preferably at least about 90 % ee. In another embodiment of the present invention, the yield of the epoxide from asymmetric epoxidation of an olefin is at least about 10%, more preferably at least about 50%, and most preferably at least about 80%.

As FIGS. 10 and 11 show, the temperature of the reaction also can affect the yield of the reaction and enantioselectivity of the epoxide. Generally, a lower reaction temperature requires a longer reaction time but results in higher enantioselectivity. Preferably, the reaction temperature is about 50° C. or less, more preferably about 30° C. or less, and most preferably about 0° C. or less. However, the scope of the present invention is not limited to these particular reaction temperatures.

As FIGS. 12–16 show, the present invention is useful for providing an epoxide from a variety of olefins. High enantiomeric excess can be obtained especially with trans-substituted olefins. The olefins can bear a wide range of groups, such as tert-butyl silyl (TBS) ether, trityl, acetal, chloride, and ester. Trisubstituted olefins also show high selectivity (See FIG. 13).

Figures 14, 15:
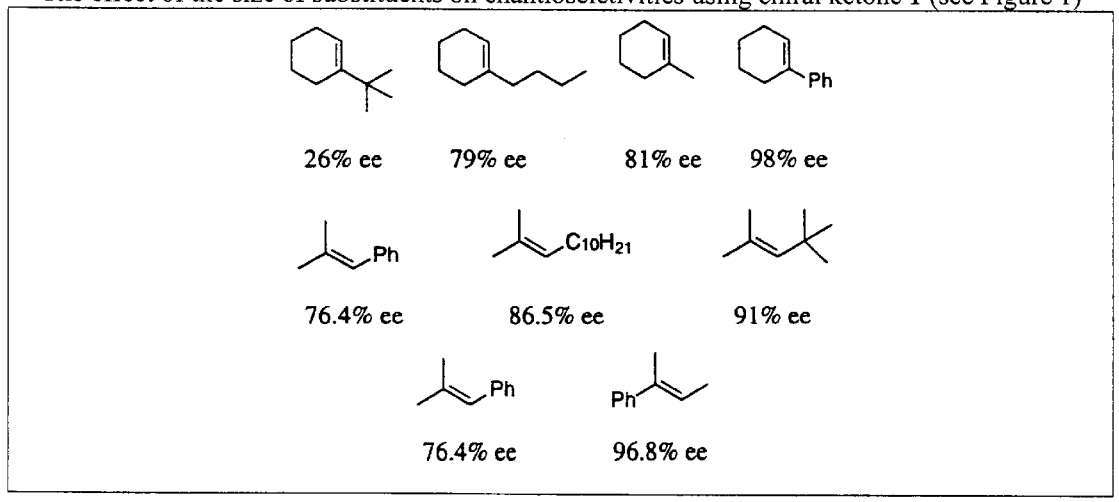
FIG. 14 shows results of the asymmetric epoxidation reaction between various cis-disubstituted & terminal olefins with chiral ketone 1 of FIG. 1. Methods are the same as in FIG. 12. All reactions were stopped after 2 h.
FIG. 15 shows the effect of the size of substituents on the olefins on enantioselectivities of the asymmetric epoxidation reaction with chiral ketone 1 of FIG. 1.

The methods of the present invention can also be used for epoxidation of cis-disubstituted and terminal olefins as shown in FIG. 14. However, as FIG. 15 illustrates, the size of substituent group on the olefin can effect the % ee of the epoxide product. For example, in tri-substituted olefins of a general structure:

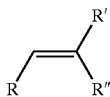

decreasing the size of R' and/or increasing the size of R typically increases the % ee.

As shown in FIG. 16, the methods of the present invention can also be used in regio- and enantioselective monoepoxidation of conjugated polyenes. A "polyene" is a compound which has more than one unsaturated bonds including dienes, trienes and enynes. Using the methods of the present invention, monoepoxidation of polyenes can be achieved by the use of appropriate amount of chiral ketone. If both olefins in a diene are disubstituted, regioselectivity can be controlled by using steric and/or electronic effects. For example, as shown in entry 3 of FIG. 16, a presence of an electron withdrawing group results in formation of the distal epoxide as the major product. And allylic electron withdrawing groups such as an acetate which is not conjugated to the olefin can also substantially deactivate the proximal olefin by the inductive effect (see entry 4 of FIG. 16). The regioselectivity can also be effected by steric hindrance. As illustrated in FIG. 16, entry 6, steric hindrance can be used to control the formation of a single monoepoxide from a polyene compound. As shown by entry 7 of FIG. 16, when a diene contains a disubstituted and a trisubstituted olefins, the epoxidation occurs selectively on the trisubstituted olefin.

One of the advantages of the present invention is availability of relatively inexpensive starting materials for producing chiral ketones. For example, as shown in FIG. 1, chiral ketones can be easily synthesized in high overall yield from readily available carbohydrates, such as fructose and sorbose. In addition, chiral ketones of the present invention can also be synthesized from other inexpensive and readily available compounds such as carvone, inositol, and quinic acid. Some of the chiral ketones which can be easily prepared from readily available starting materials and their representative epoxidation of olefins are shown in FIGS. 4–7.

Asymmetric epoxidation of olefins according to the present invention can be performed in a variety of different sequences. The addition sequences of the olefin, ketone, and oxidizing agents (and base if added) can be interchanged depending on the nature of each components. Typically, however, an oxidizing agent and a separate base are added to a reaction mixture comprising the chiral ketone and the olefin. A reverse-addition technique can also be used depending upon the reactivity of each component. A reverse-addition is where the chiral ketone is added to the reaction mixture comprising the oxidizing agent. Typically, the initial concentration of the olefin is from about 0.001 mole/liter (M) to about 10 M, preferably from about 0.02 M to about 1 M.

When a solution comprising an oxidizing agent is used, preferably the initial concentration of oxidizing agent is from about 0.1 mole/liter (M) to about 1 M, more preferably from about 0.2 M to about 0.5 M. The rate of addition of the oxidizing agent to the solution comprising the ketone and the olefin will vary depending upon a various factors such as the size of the reaction and the substrates.

In some instances, the epoxide can be easily separated from the ketone. For example, some epoxides readily dissolve and remain in relatively non-polar organic solvents such as hexane, pentane, and the like, whereas some ketones remains in aqueous solution. In such instances, the reaction mixture is typically diluted with an extraction solvent to separate the epoxide from the ketone. Additionally, aqueous solution can also be added to the reaction mixture to further facilitate removal of the ketone from the organic layer. After separating the two layers, the extraction solvent layer comprising the epoxide can further be washed with an aqueous solution to further remove the ketone that may be present in the extraction solvent layer. This washing can be repeated until substantially all of the ketone is removed from the extraction solvent layer. Conversely, the aqueous layer can be further washed with the extraction solvent to further obtain the epoxide that may be present in the aqueous layer. Again, this extraction can be repeated until substantially all the epoxide has been obtained. The epoxide which is separated from the ketone can further be purified by any of the current separation methods such as chromatography, distillation, and crystallization.

Another aspect of the present invention provides a method for increasing a relative concentration of at least one stereoisomer of an olefin from a stereoisomer mixture of the olefin, i.e., kinetic resolution of an olefin. Methods of the present invention can be used to enrich (i.e., increase a relative concentration of) a geometric isomer, a diastereomer and/or an enantiomer. Preferably, the method of the present invention enriches a diastereomer or an enantiomer.

In this aspect of the present invention, the olefin compound contains at least one chiral center. A chiral center (i.e., stereochemical center, or stereogenic center) is, of course, an atom to which four different groups are attached; however, the ultimate criterion of a chiral center is nonsuperimposability on the mirror image. Preferably, the chiral center is spatially in close proximity to the olefinic moiety that undergoes epoxidation by the methods of the present invention. In this manner, the chiral center of the compound influences the rate of epoxidation of the olefin moiety by, among others, its interaction with the chiral center(s) of the chiral ketone.

The kinetic resolution of the present invention is based on the observation that the rate of asymmetric epoxidation using a chiral ketone is influenced by the presence of a chiral center proximal to the olefin moiety that undergoes epoxidation. Thus, the kinetic resolution methods of the present invention involve converting one of the stereoisomer of the olefin to an epoxide at a higher rate than the other isomer, which results in a relative enrichment of the other stereoisomer. The terms "enrichment" and "relative enrichment" are used herein interchangeably to describe an increase of one stereoisomer relative to the other. It should be appreciated that enrichment of an olefin is a result of a decrease in the amount of one stereoisomer by conversion to an epoxide.

Another aspect of the present invention provides a method for producing an α-acyloxy carbonyl compound from an enol ester olefin, i.e., a compound having a general structure of:

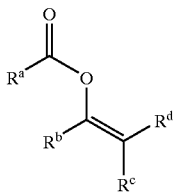

where each of $R^a$, $R^b$, $R^c$ and $R^d$ is independently hydrogen or a hydrocarbon moiety. The α-acyloxy carbonyl compound producing method comprises:

(a) contacting an oxidizing agent with an enol ester olefin in the presence of a chiral ketone of Formula I under conditions sufficient to produce a non-racemic enol ester epoxide from the enol ester olefin, and (b) contacting the non-racemic enol ester epoxide with an acid catalyst under conditions sufficient to stereoselectively produce a non-racemic α-acyloxy carbonyl compound.

Methods for producing the non-racemic α-acyloxy carbonyl compound can also include enantiomerically enriching the non-racemic enol ester epoxide prior to the acid catalyzed rearrangement reaction of step (b) above. Any suitable methods for enantiomerically enriching a chiral compound can be used, including chiral liquid or gas chromatography, recrystallization, derivatization, enzymatic resolution, as well as other chiral separation methods known to one skilled in the art.

The acid catalyzed rearrangement reaction of step (b) can further provide a kinetic resolution (i.e., enantiomeric enrichment) of the non-racemic enol ester epoxide by converting one particular stereoisomer of the enol ester epoxide to an α-acyloxy carbonyl compound at a rate faster than the other enol ester epoxide stereoisomer. This kinetic resolution results in production of enantiomeric enrichment of the α-acyloxy carbonyl compound and enantiomeric enrichment of the unreacted (or slower reacting) enol ester epoxide isomer. The enantiomerically enriched enol ester epoxide resulting from this kinetic resolution can be further converted to α-acyloxy carbonyl compound, thereby increasing the yield of the total α-acyloxy carbonyl compound with a desired stereochemistry. For example, converting the non-racemic chiral enol ester epoxide to the α-acyloxy carbonyl compound with inversion of stereochemistry and converting the enantiomerically enriched slower reacting enol ester epoxide isomer with retention of stereochemistry, or vice versa, results in same α-acyloxy carbonyl compound isomer. Alternatively, the resulting enantiomerically enriched enol ester epoxide can be separated and converted to the α-acyloxy carbonyl compound with inversion of stereochemistry; thus, allowing production of stereoisomerically enriched α-acyloxy carbonyl compound of both stereoisomers.

In one embodiment of the present invention, methods for producing α-acyloxy carbonyl compound include contacting the non-racemic enol ester epoxide with a catalyst, preferably an acid catalyst, under conditions sufficient to produce α-acyloxy carbonyl compound with inversion of stereochemistry. Preferably, the catalyst is a Lewis acid comprising a chiral ligand. In particular, the Lewis acid comprises a metal. Preferably, the metal is selected from the group consisting of Al, B, Sn, transition metals, lanthanide metals, actinide metals, and mixtures thereof. More preferably, the metal is titanium.

Suitable chiral ligands of the present invention are those possessing one or more chiral centers and are capable of exerting facial selectivity of a reaction based on their chirality. Any conventional chiral ligands known to one skilled in the art and are compatible with the reaction conditions can be used. Exemplary chiral ligands include BINOL, tartrate, and other chiral ligands which are used in a variety of organic reactions. In one particular embodiment of the present invention, BINOL is used as a chiral ligand. Preferably, the chiral ligand is selected from the group consisting of (R)—BINOL and (S)—BINOL.

In another embodiment, the methods for producing α-acyloxy carbonyl compound include contacting the non-racemic enol ester epoxide with a catalyst, preferably an acid catalyst, under conditions sufficient to produce α-acyloxy carbonyl compound with retention of stereochemistry.

Figure 20:
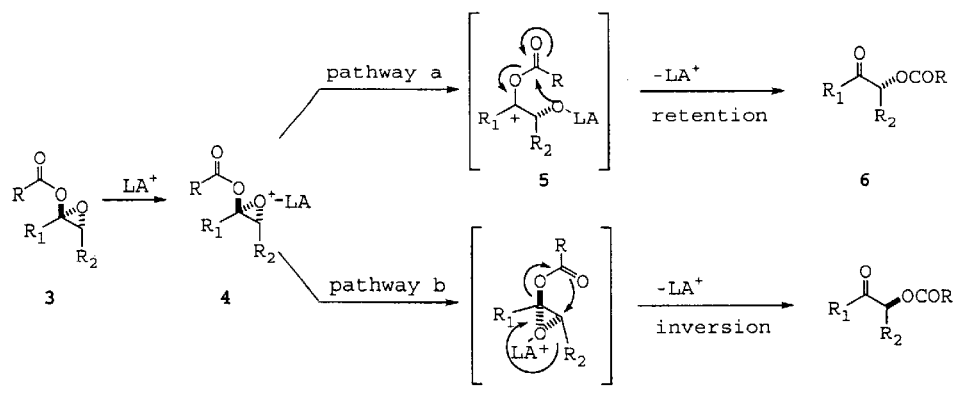
FIG. 20 illustrates two possible mechanisms of acid catalyzed enol ester epoxide rearrangement to produce α-acyl carbonyl compound.
Figures 21, 22:
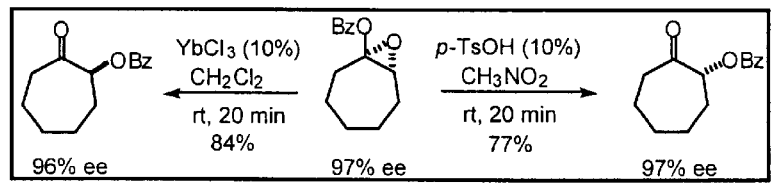
FIG. 21 shows the results of rearrangement of enol ester epoxides catalyzed by different acids. Footnote a: All reactions were carried out at room temperature with 10 mol % p-TsOH (dried by azeotropic removal of its hydrate) in dry CH₃NO₂, or 5–10 times (by weight) silica gel (Davisil 35–60 mesh, pH 7.0) in CH₃NO₂, or 10 mol % YbCl₃ in CH₂Cl₂, or 10 mol % AlMe₃ in CH₃NO₂ unless otherwise noted. Footnote b: 100 mol % AlMe₃ was used. Footnote c: 20 mol % AlMe₃ was used. Footnote d: The values in parentheses are the ee's after recrystallization.
FIG. 22 shows the results of rearrangement of enol ester epoxides catalyzed by YbCl₃ and P-TsOH.

The stereoselectivity of acid catalyzed rearrangement reaction of step (b) can vary depending on a variety of factors. For example, as FIGS. 20–22 show a particular Lewis acid catalyst used in converting an enol ester epoxide can affect the enantiomeric excess of the resulting α-acyloxy carbonyl compound. Thus, while some acids such as p-TsOH, $Sn(OTf)_2$ and $Yb(OTf)_3$ provide high ee % of the retention product, other acids such as $YbCl_3$, $ErCl_3$, $AlMe_3$, $AlEt_2Cl$ and silica gel provide high ee % of the inversion product.

A wide variety of Lewis acids can be used to convert an enol ester epoxide to an α-acyl carbonyl compound. There are many acid catalysts known to one of ordinary skill in the art which produce an α-acyl carbonyl compound from an enol ester epoxide with retention of stereochemistry.

As shown in FIGS. 20–22, some Lewis acid catalysts are capable of stereoselectively producing an α-acyl carbonyl compound from an enol ester epoxide with an inversion of stereochemistry. By utilizing the disclosure of the present invention, one of ordinary skill in the art can readily determine other Lewis acid catalysts which are capable of providing an inversion of stereochemistry during the rearrangement reaction. For example, one of ordinary skill in the art can use the reaction shown in FIGS. 19–22 or in the Examples section to determine whether a particular acid catalyst is capable of converting an enol ester epoxide to an α-acyloxy carbonyl compound with inversion of stereochemistry. Thus, using an appropriate Lewis acid catalyst, an α-acyloxy carbonyl compound with an inversion of stereochemistry having an enantiomeric excess of at least about 12% ee can be obtained by the method of the present invention, preferably with an enantiomeric excess of at least about 80% ee, more preferably at least 90% ee, and most preferably at least about 95% ee.

Figure 19:
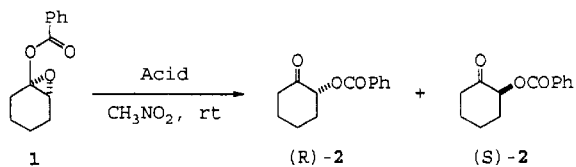
FIG. 19 shows the effects of different acid catalysts on the rearrangment reaction of 1-benzoyloxy-1,2-epoxycyclohexane. All reactions were carried out in nitromethane under anhydrous conditions at room temperature using 10 mol % acid catalyst except entry 12 where 5–10 times (by weight) silica gel (Davisil 35–60 mesh, pH 7.0) was used. Epoxide 1 was freshly made and stored at −20° C. prior to use to avoid decomposition.

Without being bound by any theory, FIG. 20 shows two possible pathways involved in the acid-catalyzed rearrangement of enol ester epoxides, thus leading to two different enantiomers. Pathways a and b outlined in FIG. 20 provide plausible mechanisms for the results. In pathway a, it is believed that the complexation of a relatively strong acid catalyst to the epoxide oxygen of 3 leads to cleavage of the $C_1$—O bond to form a carbocation intermediate 5. Subsequent acyl migration with retention of configuration gives acyloxy ketone 6. In pathway b, the complexation of a relatively weak acid to 3 weakens both epoxide bonds, facilitating acyloxy migration with inversion of configuration as shown in intermediate 7. Thus, it is believed that the acidity of the catalyst is one of the factors determining whether the catalyst is capable of producing an α-acyloxy carbonyl compound from an enol ester epoxide with inversion of stereochemistry. For example, as shown in FIG. 19, when Yb(OTf)$_3$ was used as the catalyst, the R enantiomer of the rearranged product was obtained in 66% ee (FIG. 19, entry 5), i.e., retention product predominates. On the other hand, when a weaker Lewis acid YbCl$_3$ was used, the S enantiomer was obtained in 82% ee (FIG. 19, entry 6), i.e., the product is predominantly derived from inversion of stereochemistry. In most cases, the enantiomeric excess of α-acyloxy carbonyl compound could be further enhanced, for example, by recrystallization.

The reaction temperature also can affect the stereoselectivity of rearrangement. Preferably, the reaction temperature of rearrangement is kept at about 25° C. or less, more preferably at about 10° C. or less, and most preferably at about 0° C. or less.

A wide variety of solvent system can be used to affect the stereoselective conversion of an enol ester epoxide to an α-acyloxy carbonyl compound. Exemplary solvents useful in the rearrangement include $CH_3NO_2$, $CH_2Cl_2$, $CHCl_3$, diethyl ether, benzene, tetrahydrofuran, dimethylformamide, toluene, xylenes, dimethylsulfoxide, acetonitrile, hexane, pentane, and mixtures thereof. Preferably, the solvent is selected from the group consisting of nitromethane, methylene chloride and mixtures thereof.

The amount of catalyst used in conversion of enol ester epoxide to an α-acyloxy carbonyl compound depends on a variety of factors. Generally, however, from about 1 mole % to about 100 mole % of catalyst relative to the enol ester epoxide is used. Preferably from about 5 mole % to about 100 mole % of catalyst relative to the enol ester epoxide, more preferably from about 5 mole % to about 50 mole % of catalyst relative to the enol ester epoxide, and most preferably from about 5 mole % to about 10 mole % of catalyst relative to the enol ester epoxide.

The reaction time also depends on a variety of factors such as temperature and concentration of each components. Generally, however, the reaction time is from about 0.1 h to about 48 h, preferably from about 0.1 h to about 10 h, and more preferably from about 0.1 h to about 1 h.

As shown in FIG. 22, synthesis of either enantiomer of an α-acyloxy carbonyl compound from one enantiomer of an enol ester epoxide is possible by carefully selecting reaction conditions, e.g., by selecting a particular acid catalyst. To test the generality of the rearrangement via pathway b, silica gel, YbCl$_3$, and AlMe$_3$ were used (FIG. 21). In most cases the isomer with inverted configuration was the major product when silica gel, YbCl$_3$, and AlMe$_3$ are used as the catalyst; however, in two cases (FIG. 21, entries 6 and 7) the rearrangement proceeded with retention of configuration. The preference for pathway a with these benzylic epoxides is believed to be due to a stabilized carbocation intermediate.

Thus, methods of the present invention also provide the flexibility to synthesize either enantiomer of α-acyloxy carbonyl compound from one enantiomer of an enol ester epoxide by judicious choice of reaction conditions, e.g., see FIG. 22.

It is believed that the ratio of chiral ligand to metal is important both for the reactivity and selectivity. Preferably, methods of the present invention uses two or more equivalents of BINOL per Ti. In addition, while a variety of aprotic organic solvent may be used in a kinetic resolution of enol ester epoxides, Et$_2$O and CH$_2$Cl$_2$ are particularly preferred solvents.

Methods of the present invention are applicable to a wide variety of ester groups with different steric and electronic properties. For example, as shown in FIG. 23, a wide range of ester groups can be present in the enol ester epoxide. In addition, methods of the present invention are applicable to enol ester epoxides containing a variety of carbocyclic ring systems, including 5, 6, 7, and 8-membered ring systems (FIG. 23, entries 1–14). Moreover, methods of the present invention provide recovery of enol ester epoxides with high enantiomeric excess. Furthermore, substantially pure epoxides can be isolated in reasonable yields.

Figure 24:
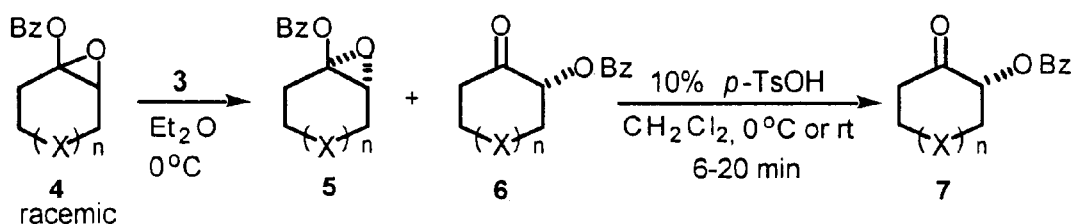
FIG. 24 shows conversion of a racemic mixture of enol ester epoxides to enantiomerically enriched α-acyloxy carbonyl compounds.

As discussed above, one embodiment of the present invention provides rearrangements, i.e., conversion of enol ester epoxide to α-acyloxy carbonyl compound, with inversion of configuration. As a result, the remaining epoxide and the rearranged α-acyloxy ketone have the same configuration at C$_2$ carbon atom. The unreacted epoxide can be then converted to the α-acyloxy ketone using an acid catalyst which is capable of catalyzing the rearrangement with retention of configuration. In this manner a high yield (>50%) of enantiomerically enriched α-acyloxy ketone can be obtained. For example, after the kinetic resolution reaction of 1-benzoyloxy-1,2-epoxycyclohexane, removal of the chiral catalyst by a filtration through a plug of silica gel, and treating the resulting mixture with 10% p-TsOH at room temperature for 20 min. gave 2-benzoyloxycyclohexanone in 78% overall isolated yield with 93% ee (FIG. 24). The % ee could be further enhanced to >99% by a single recrystallization from Et$_2$O. In this manner, both stereoisomers of enol ester epoxides in a racemic mixture can be stereoselectively converted to an enantiomerically enriched α-acyloxy carbonyl compound using a catalytic amount of a chiral Lewis acid followed by a catalytic amount of an achiral acid.

Alternatively, the remaining (i.e., enantiomerically enriched) enol ester epoxide can be separated and converted to the α-acyloxy carbonyl compound with inversion of stereochemistry, thereby providing methods for producing two separate and isomeric enantiomerically enriched α-acyloxy carbonyl compounds from a single racemic mixture of enol ester epoxides.

Additional objects, advantages, and novel features of this invention will become apparent to those skilled in the art upon examination of the following examples thereof, which are not intended to be limiting.

EXAMPLES

The following examples are offered to illustrate, but not to limit the claimed invention.

General Methods

Oxone® (potassium peroxymonosulfate) was purchased from Aldrich (Milwaukee, Wis.). It has been found that the oxidation activity of the purchased Oxone® occasionally varies with different batches. All glassware used for the epoxidation was carefully washed to be free of any trace metals which catalyze the decomposition of Oxone. Silica gel 60 of E-Merck Co. was employed for all flash chromatography.

Synthesis of Ketone 1 and Ent-1 (FIG. 1)

As shown in FIG. 1, ketone 1 is readily prepared from very inexpensive D-Fructose by ketalization and oxidation. See Mio et al. *Tetrahedron* 1991, 47, 2133–2144. The enantiomer of ketone catalyst 1 (ketone ent-1) is prepared in the same way from L-fructose (ent-5), which can be prepared from readily available L-sorbose by ketalization, mesylation, and one pot acid-base treatment based on the reported procedure. See Chen et al., *Carbohydr. Res.* 1988, 175, 265–271. Ketone ent-1 prepared by this way shows the same enantioselectivity for the epoxidation as ketone 1.

1,2:4,5-Di-O-isopropylidene-D-erythro-2,3-hexodiuro-2,6-pyranose (1)

Perchloric acid (70%) (8.6 mL) was added to a suspension of D-fructose (36.84 g, 204.7 mmol) in acetone (740 mL) and 2,2-dimethoxypropane (14.8 mL, 120 mmol) at 0° C. (ice bath). After the reaction mixture was stirred under nitrogen at 0° C. for 6 h, concentrate ammonium hydroxide was added to pH=7–8. After the resulting mixture was stirred for another 5 min, the solvent was removed under reduced pressure, and the solid residue was recrystallized from hexane/$CH_2Cl_2$ (4/1, V/V) to afford white needles (alcohol 6) (28.34 g, 53.2%).

PCC (11.64 g, 54 mmol) was added portionwise over 15 min to a mixture of alcohol 6 (5.2 g, 20 mmol) and powdered 3 A molecular sieves (22 g, activated at 180–200° C. under vacuum) in $CH_2Cl_2$ (100 mL). After the reaction mixture was stirred for 3 h under nitrogen, it was filtered through celite and washed carefully with ether. The filtrate was concentrated and the residue was purified by passing through a short silica gel column (hexane:ether=1:1, V/V) to afford a white solid (4.80 g, 93.0%), which was recrystallized from hexane/$CH_2Cl_2$ to give white crystals (ketone 1).

1,2:4,5-Di-O-isopropylidene-L-erythro-2,3-hexodiuro-2,6-pyranose (ent-1).

A solution of 1,2-dimethoxyethane (0.5 mL) containing $SnCl_2$ (0.0125 g, 0.066 mmol) was added to a suspension of L-sorbose (5 g, 27.75 mmol) in 2,2-dimethoxypropane (15 mL). The mixture was refluxed gently with stirring until it was clear, then evaporated to a syrup (alcohol 8).

The syrup was dissolved in $CH_2Cl_2$ (15 mL), followed by the addition of pyridine (3.5 mL, 43.3 mmol) and DMAP (catalytic amount). The solution was then cooled in an ice bath, and methanesulfonyl chloride (3.3 mL, 42.6 mmol) was added dropwise. After the reaction mixture was stirred for 2 h at 0° C., water was added. The mixture was extracted with $CH_2Cl_2$. The combined organic layers were washed with brine, dried ($Na_2SO_4$), filtered, and concentrated to give crude mesylate 9. Recrystallization from ethanol gave colorless needles (3.63 g, 41% yield for two steps). In a separate run the crude mesylate was flash chromatographed (hexane:EtOAc=3:1, V/V) to give 9 as a pale yellow solid (5.3 g, 60%).

To a solution of mesylate 9 (29.5 g, 87.3 mmol) in acetone (236 mL), was added an aqueous solution of 0.25% $H_2SO_4$ (177 mL). After being stirred at 25° C. for 20 h, the solution was made alkaline with 9 M NaOH (23.6 mL). The resulting mixture was heated at 70–80° C. for 48 h, acidified to about pH 1 with 9 M $H_2SO_4$, and heated at 70–80° C. for 20 min. After being neutralized with 2 M NaOH, the mixture was taken to dryness and the residue was extracted with ethanol (500 mL). The ethanol solution was concentrated to a syrup (L-fructose) (14 g, 85%).

The resulting crude L-fructose was directly converted to ketone ent-1 using the same procedure as D-fructose. The resulting ketone ent-I showed the same enantioselectivity as ketone 1.

Procedure for pH Study

To a 100 mL three-neck round bottom flask were added buffer (10 mL) [$4\times10^{-4}$ M aq. $Na_2$EDTA adjusting with 1.0 M KOH for pH 7.5–8.0; 0.05 M $Na_2B_4O_7 \cdot 10H_2O$ in $4\times10^{-4}$ M aq. $Na_2$EDTA adjusting with 1.0 M aq. $KH_2PO_4$ for pH 8.5–10.5; 0.05 M aq $K_2HPO_4$ plus 0.1 M aq. NaOH (2:1, V/V) adjusting with 1.0 M $KH_2PO_4$ for pH 11.0–12.0; 0.05 M aq $K_2HPO_4$ plus 0.1 M aq. NaOH (2:1, V/V) adjusting with 1.0 M KOH for pH 12.5–13.0], acetonitrile (15 mL), trans-β-methylstyrene (0.118 g, 1 mmol), tetrabutylammonium hydrogen sulfate (0.015 g, 0.04 mmol), and ketone 1 (0.0516 g, 0.2 mmol). The reaction mixture was cooled by an ice bath. A solution of Oxone® (1.54 g, 2.5 mmol) in aq. $Na_2$EDTA ($4\times10^{-4}$ M, 10 mL) was added through a syringe pump at a speed of 4.1 mL/h. The reaction pH was monitored by a Corning 320 pH meter with a Corning "3 in 1" pH combination electrode and was maintained within ±0.1 by adding 0.5 N aq. KOH.

The conversion and ee values were checked by GC every 30 min.

General Epoxidation Procedures

Method A

Aqueous $Na_2$EDTA ($1\times10^{-4}$ M, 10 mL) and a catalytic amount of tetrabutylammonium hydrogen sulfate were added to a solution of trans-stilbene (0.18 g, 1 mmol) in acetonitrile (15 mL) with vigorous stirring at 0° C. A mixture of Oxone® (3.07 g, 5 mmol) and sodium bicarbonate (1.3 g, 15.5 mmol) was pulverized and a small portion of this mixture was added to the reaction mixture to bring the pH to >7. After 5 min, ketone 1 (0.77 g, 3 mmol) was added portionwise over a period of 1 h. Simultaneously, the rest of Oxone® and sodium bicarbonate was added portion was added portionwise over 50 min. After the completion of the addition of ketone 1, the reaction mixture was stirred for another 1 h at 0° C., diluted with water (30 mL), and extracted with hexanes (4×40 mL). The combined extracts were washed with brine, dried ($Na_2SO_4$), filtered, concentrated, and purified by flash chromatography [the silica gel was buffered with 1% triethylamine solution in hexane; hexane/ether (1/0 to 50/1, V/V) was used as the eluent] to afford trans-stilbene oxide as white crystals (0.149 g, 73% yield, 95.2% ee).

Method B

To a 100 mL three-neck round bottom flask, were added buffer (0.05 M $Na_2B_4O_7 \cdot 10H_2O$ in $4\times10^{-4}$ M aq. $Na_2$EDTA, 10 mL), acetonitrile (15 mL), trans-β-methylstyrene (0.118 g, 1 mmol), tetrabutylammonium hydrogen sulfate (0.015 g, 0.04 mmol), and ketone 1 (0.0774 g, 0.3 mmol). The reaction mixture was cooled by an ice bath. A solution of Oxone® (0.85 g, 1.38 mmol) in aq. $Na_2$EDTA ($4\times10^{-4}$ M, 6.5 mL) and a solution of $K_2CO_3$ (0.8 g, 5.8 mmol) in water (6.5 mL) were added dropwise through two separate addition funnels over a period of 1.5 h (under this condition, the reaction pH is around 10.5. At this point, the reaction was immediately quenched by addition of pentane and water. The mixture was extracted with pentane (3×30 mL), washed with brine, dried over $Na_2SO_4$, purified by flash chromatography [the silica gel was buffered with 1% $Et_3N$ in pentane, pentane/ether (1/0 to 50/1, V/V) was used as eluent] to afford trans-β-methylstyrene oxide as colorless liquid (0.124 g, 93% yield, 92% ee).

Method C

Reaction at 20° C.: trans-Stilbene (0.181 g, 1 mmol) was dissolved in acetonitrile/DMM (15 mL, ½, V/V). subsequently were added buffer (10 mL, 0.05 M solution of $Na_2B_4O_7 \cdot H_2O$ in $4\times10^{-4}$ M aqueous $Na_2$EDTA), tetrabutylammonium hydrogen sulfate (0.015 g, 0.04 mmol), and ketone 1 (0.0774 g, 0.3 mmol). A solution of Oxone® (1.0 g, 1.6 mmol) in aqueous $Na_2$EDTA ($4\times10^{-4}$ M, 6.5 mL) and a solution of $K_2CO_3$ (0.93 g, 6.74 mmol) in water (6.5 mL) were added dropwise separately over a period of 30 min (via additional funnels). The reaction was then worked up by the same procedure as Method A to afford trans-stilbene oxide (0.166 g, 85% yield, 97.9% ee).

Reaction at 0° C.: trans-Stilbene (0.181 g, 1 mmol) was dissolved in acetonitrile/DMM (15 mL, ½, V/V), subsequently were added buffer (10 mL, 0.05 M solution of $Na_2B_4O_7.H_2O$ in $4\times10^{-4}$ M aqueous $Na_2EDTA$), tetrabutylammonium hydrogen sulfate (0.015 g, 0.04 mmol), and ketone 1 (0.0774 g, 0.3 mmol). The mixture was cooled by an ice bath. A solution of Oxone® (0.85 g, 1.38 mmol) in aqueous $Na_2EDTA$ ($4\times10^{-4}$ M, 6.5 mL) and a solution of $K_2CO_3$ (0.8 g, 5.8 mmol) in water (6.5 mL) were added dropwise separately over a period of 1.5 h (via syringe pumps or additional funnels). The reaction was then worked up by the same procedure as Method A to afford trans-stilbene oxide (0.153 g, 78% yield, 98.9% ee).

Reaction at −10° C.: trans-β-methylstyrene (0.181 g, 1 mmol) was dissolved in acetonitrile/DMM (15 mL, ½, V/V). Buffer (10 mL, 0.05 M solution of $Na_2B_4O_7.H_2O$ in $4\times10^{-4}$ M aqueous $Na_2EDTA$), tetrabutylammonium hydrogen sulfate (15 mg, 0.04 mmol), and ketone 1 (0.0774 g, 0.3 mmol) were added with stirring. The mixture was cooled to about −10° C. via a NaCl-ice bath. A solution of Oxone® (0.85 g, 1.38 mmol) in aqueous $Na_2EDTA$ ($4\times10^{-4}$ M, 6.5 mL) and a solution of $K_2CO_3$ (0.8 g, 5.8 mmol) in water (6.5 mL) were added dropwise separately over a period of 2 h (via syringe pumps or addition funnels). The reaction was then worked up by the same procedure as Method B to afford trans-β-methylstyrene oxide (0.126 g, 94% yield, 95.5% ee).

(R,R)-2-[(tert-Butyldimethylsiloxy)methyl]-3-phenyloxirane (FIG. 12, entry 3): The olefin substrate was prepared from cinnamyl alcohol and tert-butyldimethylsilyl chloride. See Corey et al., *J. Am. Chem. Soc.* 1972, 94, 6190–6191.

(R,R)-2-Phenyl-3-[(triphenylmethoxy)methyl]oxirane (FIG. 12, entry 4): The olefin was prepared from cinnamyl alcohol and triphenylmethyl chloride according to the procedure by Chaudlrary et al., *Tetrahedron Letter* 1979, 95–98, to yield white crystals.

(2S,3R)-2-(Ethylenedioxymethyl)-3-phenyloxirane (FIG. 12, entry 6): The olefin was prepared by ketalization of cinnamyl aldehyde with ethylene glycol according to the procedure by Daignault et al., *Org. Synth. Collect.* Vol V 1973, 303–306, to provide a colorless oil.

(R,R)-2-Methyl-3-(2-methylphenyl)oxirane (FIG. 12, entry 7): The olefin was prepared from o-methylbenzyltriphenylphosphonium bromide and acetaldehyde by Wittig reaction with a ratio of trans/cis=2.3 (determined by $^1H$ NMR).

(R,R)-2-Isopropyl-3-(2-methylphenyl)oxirane (FIG. 12, entry 8): The olefin was prepared from o-methylbenzyltriphenylphosphonium bromide and isobutyradehyde via Wittig reaction with a ratio of trans/cis=4.1 (determined by $^1H$ NMR).

(R,R)-2-[(tert-Butyldimethylsiloxy)methyl]-3-propyloxirane (FIG. 12, entry 9): The olefin was prepared from trans-2-hexene-1-ol and tert-butyldimethylsilyl chloride according to the procedure by Corey et al., *J. Am. Chem. Soc.* 1972, 94, 6190–6191, to provide a colorless oil.

(R,R)-2-[1-(tert-Butyldimethylsiloxy)ethyl]-3-ethyloxirane (FIG. 12, entry 10): The olefin was prepared from trans-3-hexene-1-ol and tert-butyldimethylsilyl chloride according to the procedure by Corey et al., *J. Am. Chem. Soc.* 1972, 94, 6190–6191, to provide a colorless oil.

(R,R)-2-Ethyl-3-(4,4-Ethylenedioxypentyl)oxirane (FIG. 12, entry 13): The olefin was prepared according to Look's method. Look, *J. Chem. Ecol.* 1976, 2, 83–86.

(R,R)-2-Benzyl-3-[2-(methoxycarbonyl)ethyl]oxirane (FIG. 12, entry 14): The olefin was prepared by Johnson-Claisen rearrangement from an allylic alcohol resulting from an addition of vinylmagnesium bromide to phenylacetaldehyde according to the method of Johnson et al., *J. Am. Chem. Soc.* 1970, 92, 741–743, to provide a colorless oil.

(R)-3-Decyl-2,2-diphenyloxirane (FIG. 13, entry 5): The olefin was prepared from undecyltriphenylphosphonium bromide and benzophenone via Wittig reaction.

(R,R)-2,3-Dimethyl-2-Phenyloxirane (FIG. 13, entry 6): The starting α,β-dimethylstyrene was prepared from ethyltriphenylphosphonium iodide and acetophenone via Wittig reaction by the method of Barton et al., *Tetrahedron* 1990, 46, 5273–5284 with a ratio of trans/cis=5 (determined by $^1H$ NMR).

(R)-2,2-Dimethyl-3-phenyloxirane (FIG. 13, entry 7): The olefin was prepared from benzyltriphenylphosphonium bromide and acetone via Wittig reaction by the method of Barton et al., *Tetrahedron* 1990, 46, 5273–5284, to provide a colorless oil.

(R)-3-Decyl-2,2-Dimethyloxirane (FIG. 13, entry 8): The olefin was prepared from undecyltriphenylphosphonium iodide and acetone via Wittig reaction.

(R)-3-Decyl-2,2-diethyloxirane (FIG. 13, entry 10): The olefin was prepared from undecyltriphenylphosphonium iodide and 3-pentanone via Wittig reaction.

(R,R)-2-[2-(Ethoxycarbonyl)ethyl]-3-hexyl-2-methyloxirane (FIG. 13, entry 11): The olefin was prepared by Johnson-Claisen rearrangement from an allylic alcohol resulting from an addition of hexylmagnesium bromide to methacrolein as described by Johnson et al., *J. Am. Chem. Soc.* 1970, 92, 741–743.

(R,R)-3-Cyclohexyl-2-[2-(methoxycarbonyl)ethyl]-2-methyloxirane (FIG. 13, entry 12): The olefin was prepared by Johnson-Claisen rearrangement from an allylic alcohol resulting from an addition of cyclohexylmagnesium bromide to methacrolein as described by Johnson et al., *J. Am. Chem. Soc.* 1970, 92, 741–743.

(R,R)-1-Methyl-3,3-ethylenedioxycyclohexene oxide (FIG. 13, entry 14): The olefin was prepared by ketalization of 3-methyl-2-cyclohexenone with 1,2-bis(trimethylsiloxy)ethane. See Tsunoda et al., *Tetrahedron Letters* 1980, 21, 1357–1358.

(R,R)-3,3-Ethylenedioxycyclohexene oxide (FIG. 14, entry 6): The olefin was prepared by ketalization of 2-cyclohexenone with 1,2-bis(trimethylsiloxy)ethane. See Tsunoda et al., *Tetrahedron Letters* 1980, 21, 1357–1358.

1-Butylcyclohexene oxide (FIG. 15): The olefin was prepared by reductive alkylation of cyclohexene oxide with n-BuLi. See Doris et al., *Tetrahedron Letters* 1994, 35, 7943–7946.

1-tert-Butylcyclohexene oxide (FIG. 15): The olefin was prepared by reductive alkylation of cyclohexene oxide with t-BuLi. See Doris et al., *Tetrahedron Letters* 1994, 35, 7943–7946.

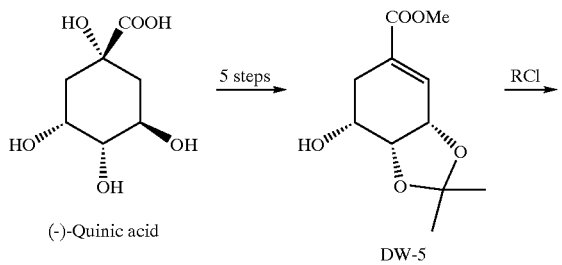

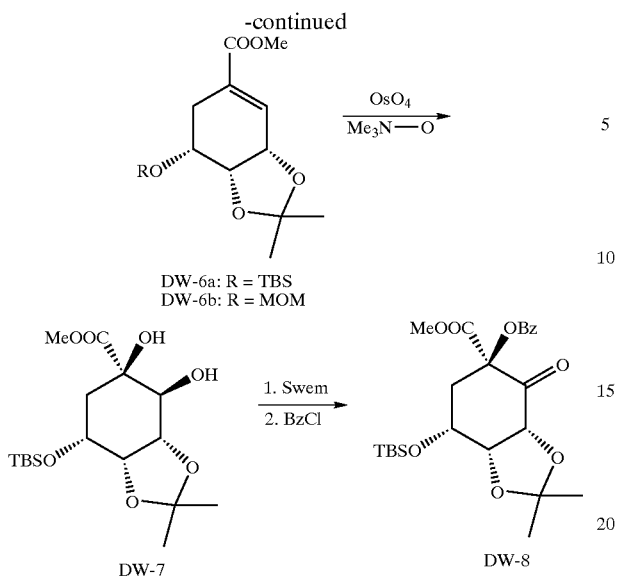

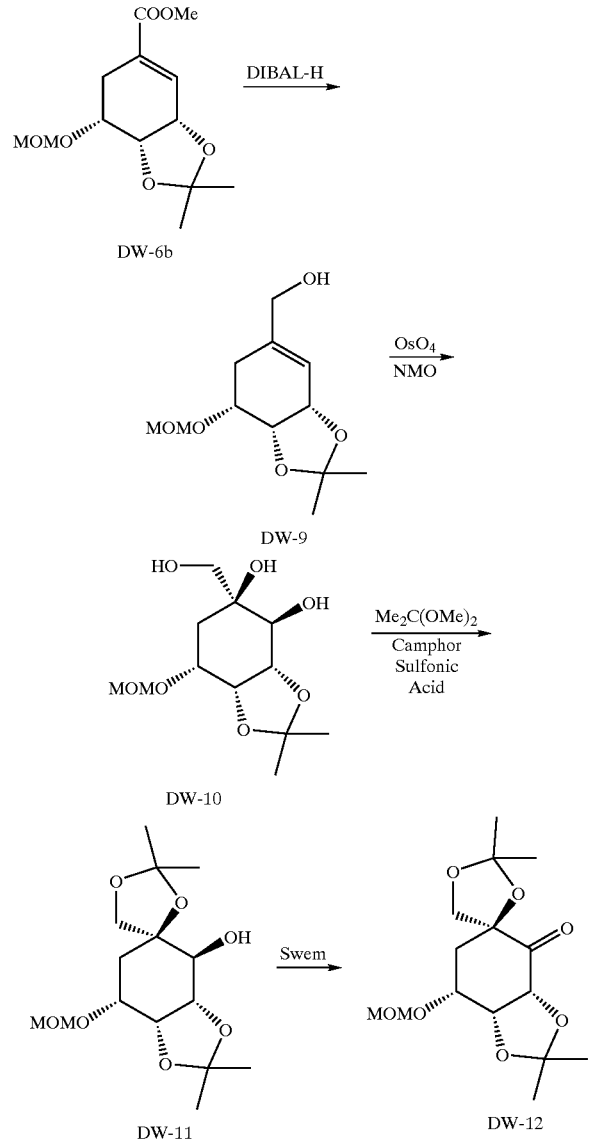

Preparation of DW-5

DW-5 was prepared based on a known procedure from (−)-Quinic acid with 5 steps. see: T. K. M. Shing et al, Tetrahedron, 1991, 47, 4571–4578. $^1$H NMR showed DW-5 was obtained a mixture of 2,3-O-isopropylidene and 1,2-O-isopropylidene with a ratio of 91.5:8.5.

Preparation of DW-6a.

To a solution of DW-5 (1.1 g, 4.8 mmol), imidazole (0.65 g, 9.6 mmol), and a catalytic amount of DMAP in dry $CH_2Cl_2$ (20 mL) was added TBSCl (0.9 g, 6.0 mmol) at room temperature. After being stirred for 10 hours, the reaction mixture was quenched with aqueous $NH_4Cl$ and extracted with $CH_2Cl_2$(3×20 mL). The combined extracts were washed with water and brine, dried over $Na_2SO_4$, concentrated and purified by flash chromatography (hexane:ether, 10:1 to 5:1) to afford 2,3-O-isopropylidene (DW-6a, 1.2 g) and 1,2-O-isopropylidene (0.16 g).

Preparation of DW-7

To a solution of DW-6a (1.0 g, 2.9 mmol), trimethylamine N-oxide dihydrate (0.6 g, 5.4 mmol), pyridine (1.8 mL), and water (0.3 mL) in t-BuOH (8 mL) was added $OsO_4$ (0.01 g, 0.039 mmol) under $N_2$. After refluxing for 10 hours, the reaction mixture was cooled, then quenched with saturated aqueous $Na_2SO_3$ (5 mL). The mixture was then passed through a short silica-gel column and eluted with ethyl acetate. The eluent was concentrated and redissolved in $CH_2Cl_2$. The resulting solution was washed with saturated aqueous $Na_2SO_3$ and water, dried over $Na_2SO_4$, and concentrated to afford DW-7 as white crystals.

Preparation of Ketone DW-8

To a stirred solution of DMSO (0.120 g, 1.6 mmol) in dry $CH_2Cl_2$ (0.5 mL) at −78° C. under nitrogen was added dropwise oxalyl chloride (0.072 mL, 0.75 mmol). The mixture was stirred for 10 min, then removed from the cold bath for 3 min, and recooled to −78° C. Alcohol DW-7 (0.19 g, 0.5 mmol) in dry $CH_2Cl_2$ (1.5 mL) was added in one portion and the mixture was stirred for 10 min. Triethylamine (0.34 mL, 2.5 mmol) was added, and the mixture was stirred for another 10 min, then slowly warmed to room temperature. The reaction mixture was quenched with saturated aqueous $NH_4Cl$, extracted with $CH_2Cl_2$, dried ($Na_2SO_4$), concentrated, and purified with flash chromatography (hexane:ethyl acetate, 5:1 to 2:1) to give the hydroxyl-ketone (0.115 g, 60%).

To a solution of the above hydroxyl-ketone (0.09 g, 0.24 mmol) in pyridine (1 mL) was added DMAP (0.005 g) and BzCl (0.2 mL). After being stirred at room temperature for 2 hours, the reaction mixture was quenched with saturated aqueous $NH_4Cl$, extracted with ether (4×10 mL), washed with water, brine, dried over $Na_2SO_4$, concentrated, and purified by flash chromatography (hexane;ethyl acetate, 8:1) to afford ketone DW-8 as a colorless syrup (0.096 g, 87%).

Preparation of DW-6b.

To solution of alcohol DW-5 (10.3 g, 45.3 mmol) in dry $CH_2Cl_2$ (55 mL) were added i-$Pr_2$NEt (12 mL), MOMCl (5.6 mL), and a catalytic amount of DMAP at 0° C. After being stirred at room temperature overnight, the reaction mixture was quenched with saturated aqueous $NH_4Cl$, extracted with $CH_2Cl_2$, washed with water and brine, dried over $Na_2SO_4$, concentrated, and purified by flash chromatography (hexane:ethyl acetate, 4:1) to give DW-6b (10.4 g, 90%).

Preparation of DW-9

To a solution of DW-6b (8.8 g, 32 mmol) in dry THF (10 mL) was added dropwise a solution of DIBAL-H (1.0 M in hexane, 70 mL) over 20 min at −15° C. The mixture was stirred at 0° C. for 1 h, quenched with the saturated aqueous $NH_4Cl$, filtered, washed with ether, and concentrated to give DW-9 as a colorless syrup (7.9 g, 99%) which was pure enough for next step.

Preparation of DW-10

To a solution of DW-9 (7.8 g, 32 mmol), NMO (6.0 g, 51 mmol), pyridine (15 mL, 192 mmol), water (3 mL, 160 mmol) in t-BuOH (60 mL) was added $OsO_4$ (0.06 g) under nitrogen with stirring. After refluxing for 5 hours, the reaction mixture was cooled, quenched with saturated aqueous $Na_2S_2O_5$ (20 mL), and concentrated. The resulting residue was filtered through a short silica-gel filter and washed with ethyl acetate and $CH_2Cl_2$—EtOH (2:1). The filtrate was concentrated and the residue was recrystallized from hexane-$CH_2Cl_2$ to give DW-10 white crystals (6.8 g, 77%).

Preparation of Ketone DW-12

To a suspension of DW-10 (1.38 g, 5 mmol) in 2,2-dimethoxypropane (20 mL) was added catalytic amount of CSA at 0° C. with stirring. After being stirred at 0° C. for 2 hours, the reaction mixture was slowly warmed to room temperature, and stirred at this temperature for another 2 hours. The reaction was quenched with triethylamine (0.2 mL), and diluted with water and ether. The aqueous solution was extracted with ether. The combined extracts were washed with water and brine, dried over $Na_2SO_4$, and concentrated to give a syrup which was used for next step without further purification.

To a solution of DMSO (0.69 g, 8.9 mmol) in dry $CH_2Cl_2$ (2 mL) was added dropwise oxalyl chloride (0.43 mL, 4.45 mmol) at −78° C. The solution was stirred at −78° C. for 10 min, then removed from cold bath for 3 min, and recooled to −78° C. A solution of the above crude alcohol in dry $CH_2Cl_2$ (5 mL) was added. After the solution was stirred at −78° C. for 1 hour, triethylamine (1.86 mL, 13.5 mmol) was added dropwise, and the resulting mixture was stirred at −78° C. for 10 min, then warmed to room temperature. After the addition of saturated aqueous $NH_4Cl$ (20 mL), the mixture was extracted with ether, washed with water and brine, dried over $Na_2SO_4$, concentrated and purified by flash chromatography (hexane:ethyl acetate, 5:1 to 2:1) to give ketone DW-12 as a light yellow oil, which was recrystallized from hexane to give white crystals (0.66 g, 42% from DW-11).

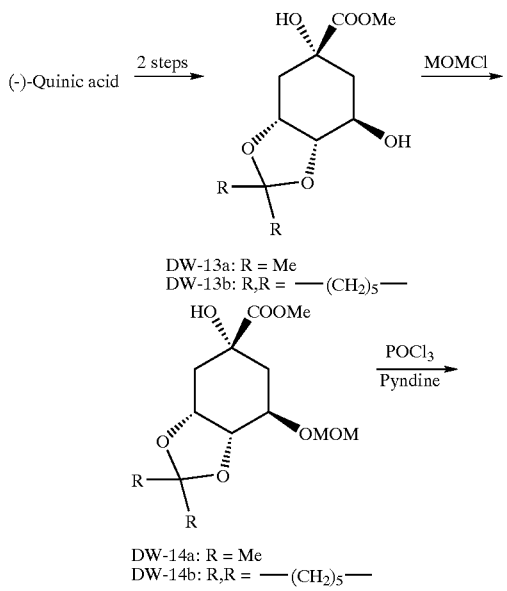

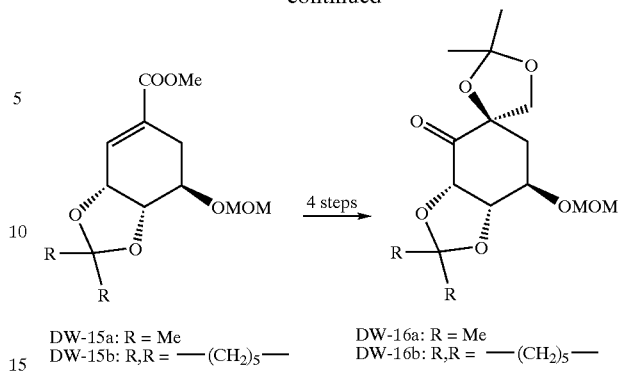

Preparation of DW-13a.

To a suspension of (−)-Quinic acid (46 g, 0.239 mol) in 2,2-dimethoxypropane (60 mL) and benzene (180 mL) was added TsOH (0.1 g). After refluxing for 15 hours, the reaction mixture was cooled to room temperature and quenched with triethylamine (0.5 mL). The solvent was removed under reduced pressure, and the residue was treated with ethyl acetate (100 mL). After filtration, the filtrate was concentrated and recrystallized in hexane-ethyl acetate to yield a lactone as white needles (43 g, 83.8%).

To a solution of the above lactone (13.4 g, 63.5 mmol) in MeOH (75 mL) was added MeONa (4.4 g, 81.5 mmol). After being stirred at room temperature for 3 hours, AcOH (4.66 mL, 81.5 mmol) was added dropwise and the solvent was removed under reduce pressure. The resulting syrup was dissolved in ether (200 mL), filtered through a thin silica-gel, washed with ether and ethyl acetate,. concentrated, and purified by flash chromatography (hexane:ethyl acetate 3:1 to 1:2, V/V) to give alcohol DW-13a as a slightly yellow syrup (10.1 g, 82%) along with recovered lactone (2 g).

Preparation of DW-13b.

DW-13b was prepared based on a reported procedure. see: T. K. M. Shing et al, Tetrahedron, 1990, 46, 6575–6584.

Preparation of DW-14a and 14b.

MOMCl (2.81 g, 35 mmol) was added dropwise to a solution of DW-13a (6.3 g, 25 mmol), i-$Pr_2NEt$ (6.3 mL, 35 mmol), and catalytic amount of DMAP in $CH_2Cl_2$ (50 mL) at 0° C. After being stirred at 0° C. for 15 hours, the reaction mixture was quenched with saturated aqueous $NH_4Cl$, and extracted with $CH_2Cl_2$, washed with water and brine, dried ($Na_2SO_4$), and concentrated to give a yellow syrup which was used for next step without further purification.

DW-14b was prepared similarly from DW-13b with 95%.

Preparation of DW-15a and 15b $POCl_3$ (2.5 mL) was added to a solution of crude DW-14a in pyridine (50 mL) at 0° C. with stirring. After being stirred at room temperature for 3 hours, the reaction mixture was diluted with ether, and quenched with saturated aqueous $NH_4Cl$ at 0° C. The aqueous layer was extracted with ether (4×30 mL), washed with water (3×50 mL), dried over $Na_2SO_4$, concentrated and purified by flash chromatography (hexane:ether, 2:1) to give DW-15a as a colorless syrup (3.7 g, 54% from DW-13a).

DW-15b was prepared Similarly from DW-14b with 60% yield.

Preparation of Ketone DW-16a and DW-16b.

The synthesis of DW-16a was similar to the synthesis of DW-12 from DW-6b. Colorless syrup.

DW-16b was prepared similarly from DW-15b.

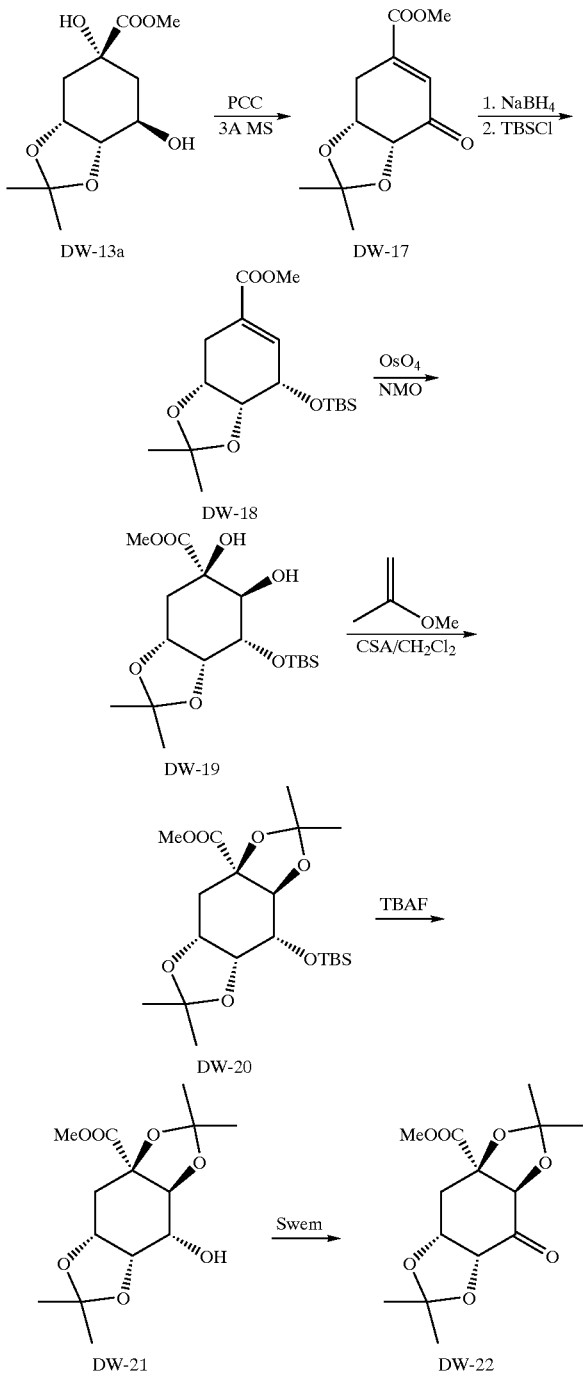

Preparation of DW-17

PCC (25 g, 116 mmol) and powdered 3 A molecular sieve (17 g) were added to a solution of DW-13a (10 g, 40 mmol) and pyridine (10 mL) in dry $CH_2Cl_2$ (100 mL). After being stirred at room temperature for 24 hours, the reaction mixture was diluted with ether (300 mL), filtered through celite, and washed with ether. The filtrate was concentrated and purified with flash chromatography (hexane:ethyl acetate, 3:1) to give enone DW-17 as white needles (5.5 g, 60%).

Preparation of DW-18

NaBH4 (1.0 g, 26 mmol) was added portionwise to a solution of enone DW-17 (5 g, 22.1 mmol) in MeOH (30 mL). After being stirred at room temperature for 0.5 hour, the reaction mixture was quenched with saturated aqueous $NH_4Cl$ (15 mL). After the removal of MeOH under reduced pressure, the resulting aqueous solution was extracted with $CH_2Cl_2$ (4×15 mL), washed with brine, dried over $Na_2SO_4$, and concentrated to give an allylic alcohol as a white solid (5 g, 98%) which was used for next step without further purification.

To a solution of the above allylic alcohol (3.2 g, 0.014 mol), Imidazole (1.7 g, 0.025 mol) and catalytic amount of DMAP in dry $CH_2Cl_2$ (50 mL), was added tert-butyldimethylsilyl chloride (3.0 g, 0.02 mol). After being stirred at room temperature for 2 hours, the reaction mixture was quenched with saturated aqueous $NH_4Cl$, extracted with ether (3×30 mL), washed with water and brine, dried over $Na_2SO_4$, concentrated and purified with flash chromatography (hexane:ether, 5:1, V/V) to give DW-18 as a colorless syrup.

Preparation of DW-19

$OsO_4$(10 mg) was added to a solution of DW-18 (4.6 g, 13.5 mmol), NMO (2.8 g, 24 mmol), pyridine (7 mL), and water (1.4 mL) in t-BuOH (45 mL) at room temperature under $N_2$. The solution was refluxed under $N_2$ for 3 hours, then cooled to room temperature, and quenched with saturated aqueous $Na_2S_2O_5$ (15 ml). Upon removing the solvent under reduced pressure, the residue was purified by flash chromatography (hexane:ether, 1:1, V/V) to afford diol DW-19 as a colorless syrup (4.8 g, 95%).

Preparation of DW-20

To a solution of diol DW-19 (4.8 g, 12.8 mmol) and 2-methoxypropene (8 mL) in dry $CH_2Cl_2$ (80 mL) was added catalytic amount of CSA under $N_2$ at room temperature. The resulting solution was stirred for 2 hours, then quenched with triethylamine (0.5 mL). Upon removing the solvent, the resulting residue was purified by flash chromatography (hexane:ether, 10:1 to 5:1. the silica-gel was pre-buffered with 1% triethylamine in hexane) to afford DW-20 as a colorless syrup (5.0 g, 94%).

Preparation of DW-21

DW-20 (1.6 g, 3.9 mmol) was dissolved in a solution of TBAF in THF (1M, 15 mL). After being stirred at room temperature for 1 hour, the reaction mixture was quenched with saturated aqueous $NH_4Cl$, extracted with ether (3×20 mL), washed with water and brine, dried ($Na_2SO_4$), concentrated and purified by flash chromatography (hexane:ether, 2:1 to 1:1, V/V) to give DW-21 as white crystals (0.82 g, 70%).

Preparation of Ketone DW-22

To a solution of DMSO (0.53 g, 6.7 mmol) in dry $CH_2Cl_2$ (2 mL) was added dropwise oxalyl chloride (0.29 mL, 3.3 mmol) under $N_2$ at −78° C. The mixture was stirred at −78° C. for 10 min, then removed from coolant and stirred for 3 min. Upon recooling to −78 ° C., a solution of alcohol DW-21 (0.67 g, 2.2 mmol) in dry $CH_2Cl_2$ (7 mL) was added in one portion. The resulting reaction mixture was stirred at −78° C. for additional 1 hour, then triethylamine (1.4 mL) was added dropwise. After being stirred at −78° C. for an another 10 mi, the reaction mixture was warmed to room temperature, quenched with saturated aqueous $NE_4Cl$ (5 mL), extracted with $CH_2Cl_2$ (3×20 mL), washed with water and brine, dried ($Na_2SO_4$), concentrated, and purified by flash chromatography (hexane:ether, 1:1 to 1:2, V/V) to give ketone DW-22 as a white solid (0.66 g, 99%).

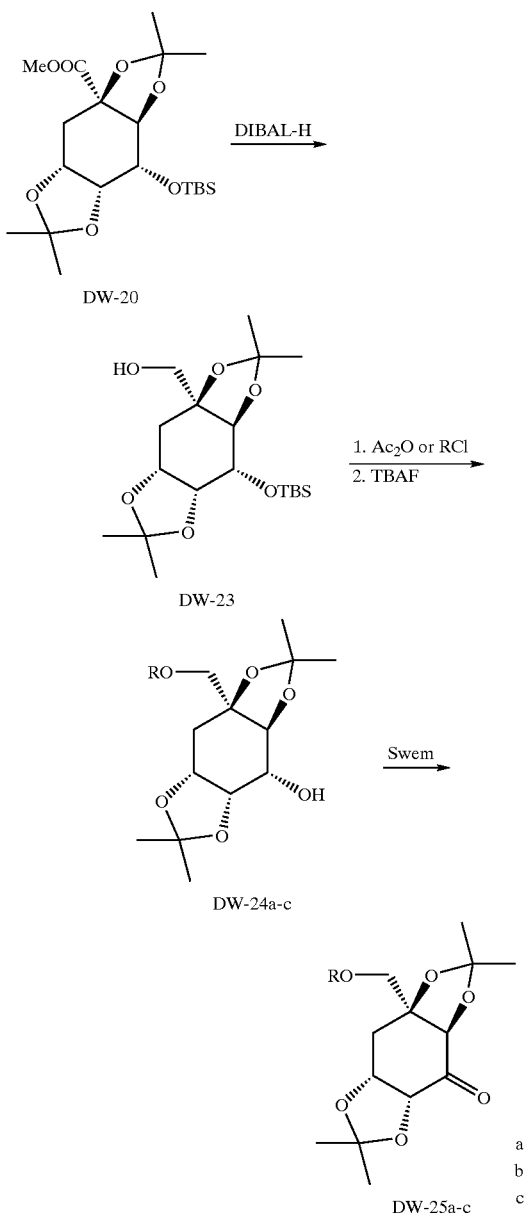

Preparation of DW-23

DIBAL-H (1.0 M in Hexane, 30 mL, 0.03 mol) was added dropwise to a solution of DW-20 (5.0 g, 0.0121 mol) in dry THF (30 mL) at −20° C. under $N_2$ over 30 min. After being stirred at 0° C. for 2 hours, the reaction mixture was quenched with saturated aqueous $NH_4Cl$ (10 mL) and filtered. The cake was washed with ether. The filtrate was extracted with ether, washed with brine, dried ($Na_2SO_4$), concentrated and purified by flash chromatography (hexane:ether, 2:1, V/V) to give DW-23 as a colorless syrup (4.3 g, 92.3%).

Preparation of DW-24a.

Acetic anhydride (0.4 mL, 4.2 mmol) was added to a solution of DW-23 (0.9 g, 2.33 mol), triethylamine (0.9 mL, 6.46 mmol), and catalytic amount of DMAP in dry $CH_2Cl_2$ (5 mL). After being stirred at room temperature for 2 hours, the reaction mixture was quenched with saturated aqueous $NH_4Cl$, extracted with $CH_2Cl_2$ (3×20 mL), washed with water and brine, dried over $Na_2SO_4$, and concentrated to give a colorless syrup which was used for next step directly.

The above crude acetate was dissolved in a solution of TBAF in THF (1 M, 8 mL). After being stirred at room temperature for 2 hours, the reaction mixture was quenched with saturated aqueous $NH_4Cl$, extracted with $CH_2Cl_2$ (4×15 mL), washed with water and brine, dried ($Na_2SO_4$), concentrated and purified by flash chromatography (hexane:ethyl acetate, 5:1 to 2:1, V/V) to afford DW-24a as white crystals (0.58 g, 86%).

Preparation of Ketone DW-25a.

To a solution of DMSO (0.41 g, 5.2 mmol) in dry $CH_2Cl_2$ (1.5 mL) was added dropwise oxalyl chloride (0.226 mL, 0.0026 mol) under $N_2$ at −78° C. The mixture was stirred at −78° C. for 10 min, then removed from coolant and stirred for 3 min. Upon recooling to −78° C., a solution of alcohol DW-24a (0.54 g, 0.00172 mol) in dry $CH_2Cl_2$ (5 mL) was added in one portion. After the mixture was stirred at −78° C. for additional 1 hour, triethylamine (1.1 mL) was added dropwise. The resulting mixture was stirred at −78° C. for an another 10 min, and warmed to room temperature. The reaction mixture was quenched with saturated aqueous $NH_4Cl$ (4 mL), extracted with $CH_2Cl_2$ (3×15 mL), washed with water and brine, dried over $Na_2SO_4$, concentrated and purified by flash chromatography (hexane:ether, 2:1 to 1:2, V/V) to give ketone DW-25a as a white solid (0.53 g, 95%).

Preparation of DW-24b.

Benzoyl chloride (0.3 mL, 2.5 mmol) was added to a solution of alcohol DW-23 (0.77 g, 2 mmol), triethylamine (0.5 mL), and catalytic amount of DMAP in dry $CH_2Cl_2$ (5 mL). After being stirred at room temperature for 2 hours, the reaction mixture was quenched with saturated aqueous $NH_4Cl$, extracted with $CH_2Cl_2$ (3×20 mL), washed with water and brine, dried over $Na_2SO_4$, and concentrated to give a crude benzoate.

The above crude benzoate was dissolved in a solution of TBAF in THF (1 M, 8 mL). After being stirred at room temperature for 1 hour, the reaction mixture was quenched with saturated aqueous $NH_4Cl$, extracted with ether, washed with water and brine, dried ($Na_2SO_4$), concentrated and purified by flash chromatography (hexane:ethyl acetate, 2;1, V/V) to give DW-24b as a colorless syrup (0.75 g, 99%).

Preparation of Ketone DW-25b.

To a solution of DMSO (0.453 g, 5.8 mmol) in dry $CH_2Cl_2$ (2 mL) was added dropwise oxalyl chloride (0.254 mL, 2.9 mmol) under $N_2$ at −78° C. The mixture was stirred at −78° C. for 10 min, then removed from coolant and stirred for 3 min. Upon recooling to −78° C., a solution of alcohol DW-25b (0.73 g, 1.93 mmol) in dry $CH_2Cl_2$ (6 mL) was added in one portion. After the mixture was stirred at −78° C. for additional 1 hour, triethylamine (1.1 mL) was added dropwise. The resulting mixture was stirred at −78° C. for an another 10 min, warmed to room temperature, quenched with saturated aqueous $NH_4Cl$ (4 mL), extracted with $CH_2Cl_2$ (3×20 mL), washed with water and brine, dried over $Na_2SO_4$, concentrated and purified by flash chromatography (hexane:ether, 2:1 to 1:2, V/V) to give ketone DW-25b as a colorless syrup (0.71 g, 96%).

Preparation of DW-24c:

TsCl (0.475 g, 2.5 mmol) was added to a solution of DW-23 (0.77 g, 2 mmol), pyridine (0.5 mL), and catalytic amount of DMAP in dry $CH_2Cl_2$ (5 mL) at 0° C. After being stirred at room temperature for 30 hours, the reaction mixture was quenched with saturated aqueous $NH_4Cl$, extracted with $CH_2Cl_2$ (3×20 mL), washed with water and brine, dried over $Na_2SO_4$, and concentrated to give the crude compound.

The above crude compound was dissolved in a solution of TBAF in THF (1 M, 10 mL). After being stirred at room temperature for 1 hour, the reaction mixture was quenched with saturated aqueous NH$_4$Cl, extracted with ether, washed with water and brine, dried (Na$_2$SO$_4$), concentrated, and purified by flash chromatography (hexane:ethyl acetate, 2:1, V/V) to give DW-24c as white crystals (0.7 g, 82%).

Preparation of Ketone DW-25c.

To a solution of DMSO (0.375 g, 4.8 mmol) in dry CH$_2$Cl$_2$ (1.5 mL) was added dropwise oxalyl chloride (0.21 mL, 2.4 mmol) under N$_2$ at −78° C. The mixture was stirred at −78° C. for 10 min, then removed from coolant and stirred for 3 min. Upon recooling to −78° C., a solution of alcohol DW-24c (0.67 g, 1.55 mol) in dry CH$_2$Cl$_2$ (4.5 mL) was added in one portion. After the mixture was stirred at −78° C. for 1 hour, triethylamine (1.05 mL) was added dropwise. The resulting mixture was stirred at −78° C. for an another 10 min, warmed to room temperature, quenched with saturated aqueous NH$_4$Cl (4 mL), extracted with CH$_2$Cl$_2$ (3×15 mL), washed with water and brine, dried over Na$_2$SO$_4$, concentrated, and purified by flash chromatography (hexane:ethyl acetate, 5:1 to 1:1, V/V) to give ketone DW-25c as a colorless syrup (0.67 g, 100%).

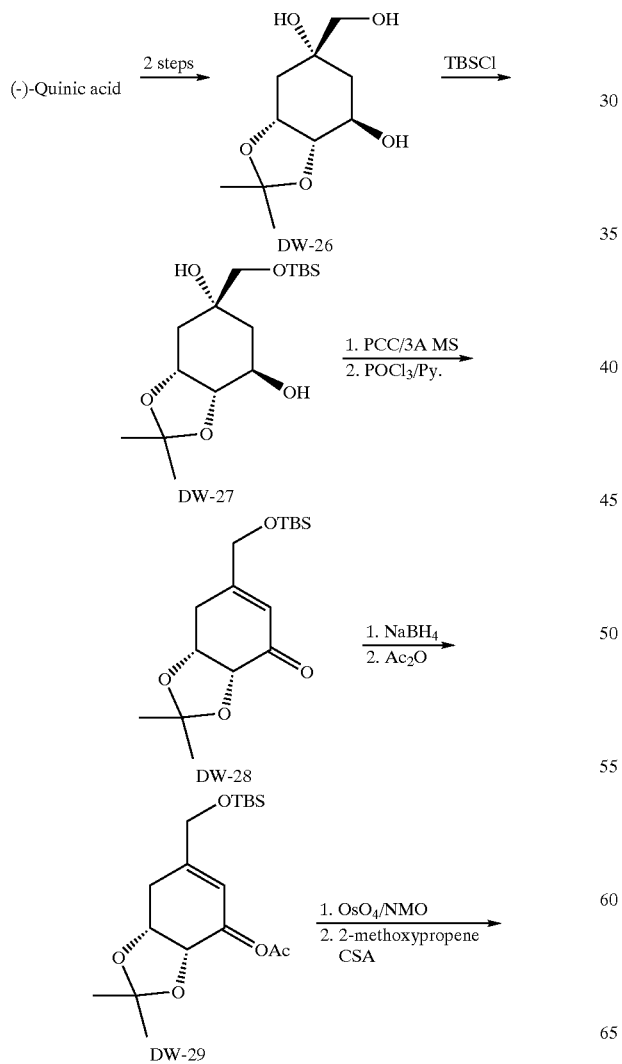

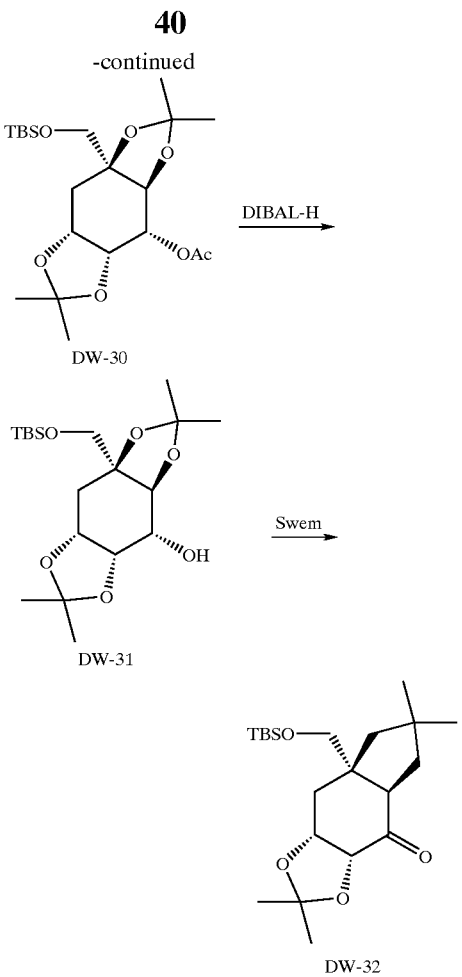

Preparation of DW-26.

After the lactone (6.2 g, 29.4 mmol) prepared from (−)-Quinic acid (see the preparation of DW-13a) was dissolved in EtOH (120 mL), NaBH$_4$ (4 g) was added. After being stirred at room temperature for 15 hours, saturated aqueous NaCl (50 mL) was added, and the mixture was stirred for an another 15 hour. Upon removing EtOH and water under reduced pressure, the resulting solid was extracted with CH$_2$Cl$_2$/MeOH (2/1, V/V). The extracts was concentrated and the residue was recrystallized from EtOH to give triol DW-26 as white crystals (6.2 g, 98%).

Preparation of DW-27.

To a solution of triol DW-26 (4.1 g, 18.8 mmol), imidazole (1.9 g, 33 mmol), and catalytic amount of DMAP in dry CH$_2$Cl$_2$ (50 mL) was added portionwise tert-butyldimethylsilyl chloride (3.5 g, 23 mmol) at 0 C. After being stirred at 0° C. for 2 hours, the reaction mixture was diluted with ether (100 mL), filtered through a thin silica-gel, and washed with ether (200 mL). The filtrate was concentrated to give DW-27 as a colorless oil (5.5 g), which was used for next step directly.

Preparation of DW-28.

After the crude DW-27 (5.5 g) was dissolved in CH$_2$Cl$_2$ (100 mL), powdered 3A MS (7 g), PCC (9 g, 41.7 mmol), and pyridine (5 mL) were added. After being stirred at room temperature overnight, the reaction mixture was diluted with ether (300 mL), filtered through thin silica-gel, and washed with ether. The filtrate was concentrated to give a colorless syrup. After the syrup was dissolved in pyridine (20 mL), the POCl$_3$ (2 mL) was added, the reaction mixture was stirred at room temperature for 16 hours, quenched with saturated aqueous NH$_4$Cl and ether, extracted with ether (3×50 mL), washed with water and brine, dried over Na$_2$SO$_4$, concentrated, purified by flash chromatography (hexane:ethyl acetate, 4:1, V/V) to afford enone DW-28 as a colorless syrup (3.1 g, 54% yield from DW-26).

Preparation of DW-29.

To a solution of enone DW-28 (1.1 g, 3.4 mmol) in EtOH (10 mL) was added NaBH$_4$ (0.3 g, 7.6 mmol). After being stirred at room temperature for 2 hours, the reaction mixture was quenched with saturated aqueous NH$_4$Cl (10 mL), extracted with CH$_2$Cl$_2$ (5×20 mL), washed with water, and brine, dried (Na$_2$SO$_4$), and concentrated to give a crude alcohol.

After the above crude alcohol was dissolved in dry CH$_2$Cl$_2$ (10 mL), pyridine (0.7 mL), acetic anhydride (0.7 mL), and catalyst amount of DMAP were added. After being stirred at room temperature for 10 hours, the reaction mixture was quenched with saturated aqueous NH$_4$Cl, extracted with CH$_2$Cl$_2$ (3×20 mL), washed with water and brine, dried over Na$_2$SO$_4$, concentrated, and purified by flash chromatography (hexane:ether, 3:1, V/V) to give DW-29 as a colorless syrup (1.2 g, 96%).

Preparation of DW-30

OsO$_4$ (10 mg) was added to a solution of DW-29 (1.2 g, 3.5 mmol), NMO (0.65 g, 5.5 mmol), pyridine (1.75 mL), and water (0.35 mL) in t-BuOH (10 mL) at room temperature under N$_2$. After being refluxed under N$_2$ for 3 hours, the reaction mixture was cooled to room temperature and quenched with saturated aqueous Na$_2$S$_2$O$_5$ (5 mL). Upon removing the solvent under reduced pressure, the resulting residue was purified by flash chromatography (hexane:ether, 1:1, V/V) to afford a diol as a colorless syrup (1.0 g, 72%).

To a solution of the above diol (0.8 g, 2 mmol) and 2-methoxypropene (1.3 mL) in dry CH$_2$Cl$_2$ (15 mL) was added catalytic amount of CSA under N$_2$ at room temperature. After being stirred for 2 hours, the reaction mixture quenched with triethylamine (0.1 mL), concentrated, and purified by flash chromatography (hexane:ether, 10:1 to 5:1. the silica-gel was prebuffered with 1% triethylamine in hexane) to afford DW-30 as a colorless syrup (0.81 g, 96%).

Preparation of DW-31.

To a solution of DW-30 (0.81 g, 1.88 mmol) in dry THF (10 mL) was added dropwise DIBAL-H solution (1.0 M in hexane, 6 mL) at −20° C. over 30 min. After being stirred at 0° C. for 3 hours, the reaction mixture was quenched with saturated aqueous NH$_4$Cl (3 mL), filtered, and washed with ether. The filtrate was concentrated and purified by flash chromatography (hexane:ether, 2:1, V/V) to give DW-31 as a colorless syrup (0.75 g, 94%).

Preparation of Ketone DW-32.

To a solution of DMSO (0.422 g, 5.4 mmol) in dry CH$_2$Cl$_2$ (1.5 mL) was added dropwise oxalyl chloride (0.250 mL, 2.7 mmol) under N$_2$ at −78° C. The mixture was stirred at −78° C. for 10 min, then removed from coolant and stirred for 3 min. Upon recooling to −78° C., a solution of alcohol DW-31 (0.70 g, 1.8 mmol) in dry CH$_2$Cl$_2$ (6 mL) was added in one portion. After the mixture was stirred at −78° C. for 1 hour, triethylamine (1.23 mL) was added dropwise. After being stirred at −78° C. for an another 10 min and warmed to room temperature, the reaction mixture was quenched with saturated aqueous NH$_4$Cl (4 mL), extracted with CH$_2$Cl$_2$ (3×20 mL), washed with water and brine, dried over Na$_2$SO$_4$, concentrated, and purified by flash chromatography (hexane:ether, 5:1 to 2:1, V/V) to give ketone DW-32 as a colorless syrup (0.63 g, 90%).

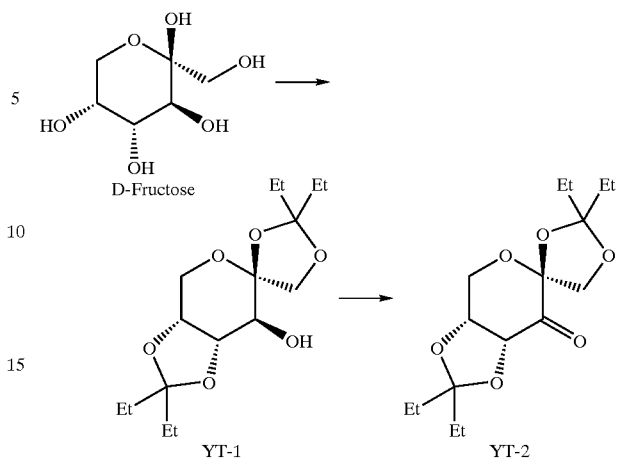

To a solution of 3-pentanone (10.6 mL, 8.6 g, 100 mmol) and trimethyl orthoformate (8.8 mL, 8.5 g, 80 mmol) in methanol (50 mL) was added TsOH.H$_2$O (0.01 g). After the solution was heated at 60–70° C. for 3 hours (during this time methyl formate formed was distilled off), the bath temperature was raised to 90° C. and maintained at that temperature for 30 minutes to distill off the methanol. Upon cooling to room temperature, dioxane (100 mL) and D-fructose (7.2 g) were added. The reaction mixture was cooled in an ice bath, and 0.1 mL of 70% perchloric acid was added. After being stirred for 6 hours, the reaction was quenched by adding triethylamine and concentrated. The resulting residue was dissolved in dichloromethane (50 mL), washed with brine, dried over sodium sulfate, concentrated, and purified by flash chromatography (hexane:ether, 20:1 to 2:1, v/v) to give alcohol YT-1 as a syrup (7.81 g, 61%).

PCC (11.8 g, 55 mmol) was added portionwise over 15 min to a mixture of alcohol YT-1 (7.52 g, 24 mmol) and powdered 3A molecular sieves (22 g, activated at 180–200° C. under vacuum) in dichloromethane (100 mL). After the reaction mixture was stirred for 3 hours under nitrogen, it was filtered through celite and washed carefully with ether. The filtrate was concentrated and the residue was purified by passing through a short silica gel column (hexane:ether, 1:1, v/v) to afford a syrup (YT-2) which solidified in refrigerator after a few hours (1.47 g, 81%).

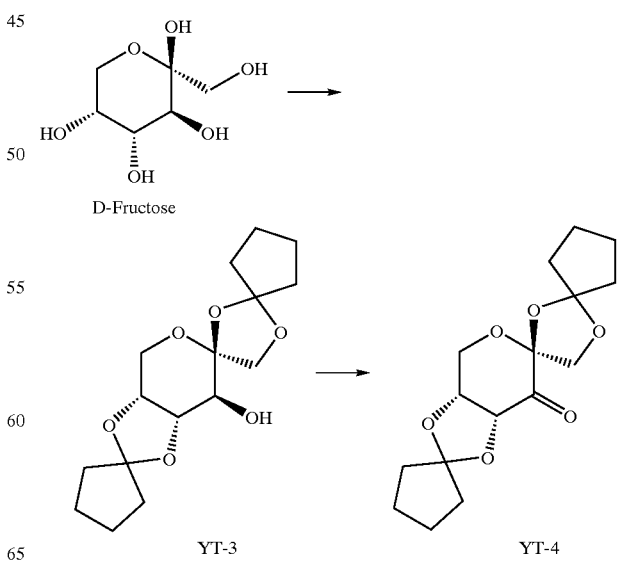

Preparation of Ketone YT-4

Perchloric acid (70%) (0.1 g) was added to a suspension of D-fructose (1.8 g, 10 mmol) in cyclopentanone (30 mL) and 1,1-dimethoxycyclopentane (2.86 g, 22 mmol) at 0° C. (ice bath). After being stirred under nitrogen at 0° C. for 6 hours, the reaction mixture was neutralized with con. ammonium hydroxide and concentrated. The resulting residue was dissolved in $CH_2Cl_2$ (20 mL), washed with brine, dried over sodium sulfate, concentrated, and purified by flash chromatography (hexane:ether, 20:1 to 2:1, v/v), and followed by recrystallization (hexane) to give alcohol YT-3 as a white needle (1.15 g, 36.9%).

PCC (1.86 g, 8.6 mmol) was added portionwise over 15 min to a mixture of alcohol YT-3 (1.0 g, 3.2 mmol) and powdered 3A molecular sieves (3.5 g) in dichloromethane (100 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-4 as colorless crystal (0.83 g, 83%).

recrystallized (hexane) to give alcohol YT-5 as a white needle (13.6 g, 36.0%).

PCC (17.46 g, 81 mmol) was added portionwise over 15 min to a mixture of alcohol YT-5 (10.2 g, 30 mmol) and powdered 3A molecular sieves (31.8 g) in dichloromethane (150 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-6 as a white solid (8.11 g, 80.0%).

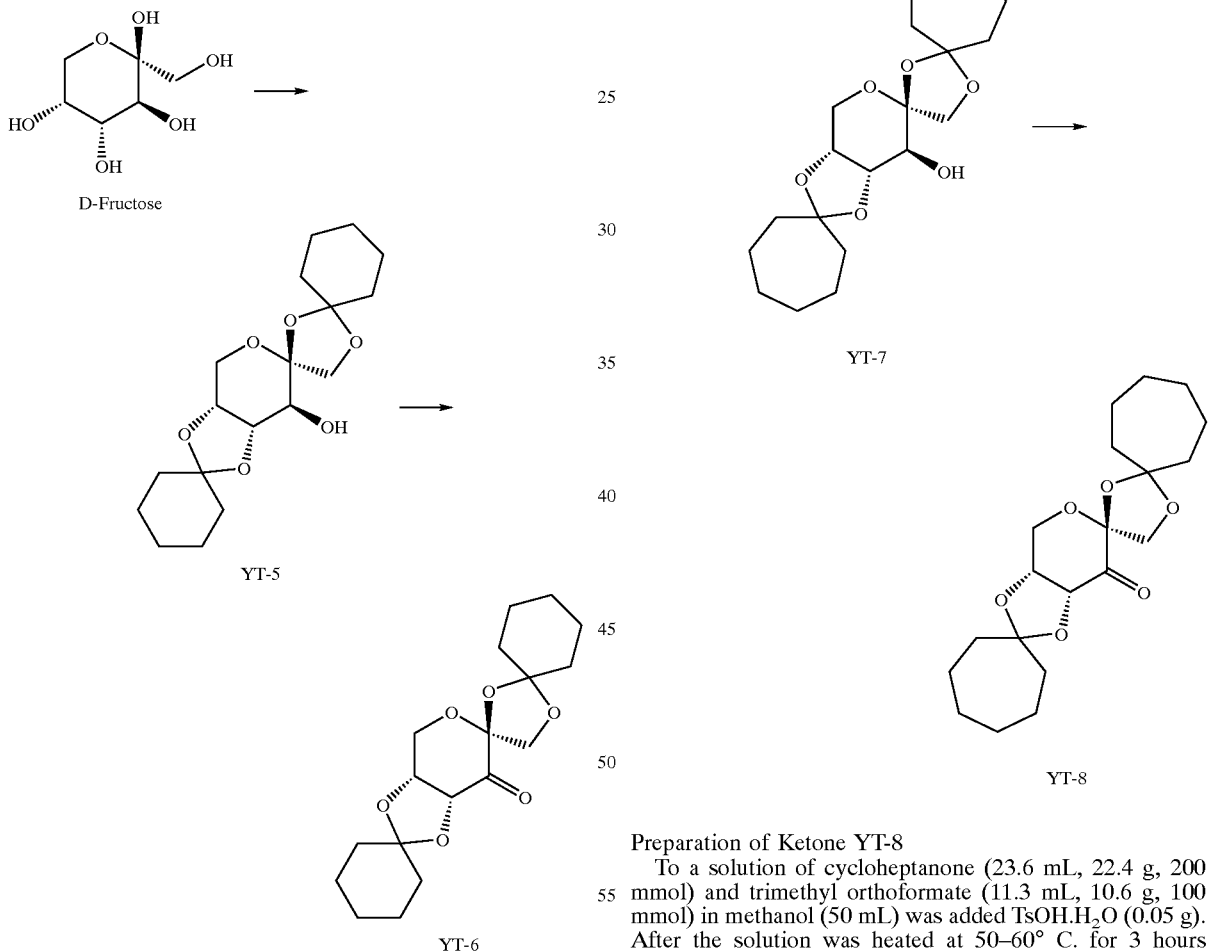

Preparation of Ketone YT-6

To a solution of con. sulfuric acid (3 mL) in cyclohexanone (40 mL) at 0° C. was added powered D-fructose (20.0 g, 111.1 mmol). The reaction mixture solidified after 40 min stirring at 0° C. After being stood at room temperature for additional 24 hours, the reaction mixture was dissolved in chloroform (150 mL) and washed with saturated sodium carbonate, brine, saturated ammonium chloride, water, brine, dried over magnesium sulfate, concentrated, and

Preparation of Ketone YT-8

To a solution of cycloheptanone (23.6 mL, 22.4 g, 200 mmol) and trimethyl orthoformate (11.3 mL, 10.6 g, 100 mmol) in methanol (50 mL) was added $TsOH \cdot H_2O$ (0.05 g). After the solution was heated at 50–60° C. for 3 hours (during this time methyl formate formed was distilled off), the bath temperature was raised to 90° C. and maintained at that temperature for 30 minutes to distill off the methanol. Upon cooling to room temperature, dioxane (50 mL) and D-fructose (9.0 g, 50 mmol) were added. The reaction mixture was cooled in an ice bath, and 1 mL of 70% perchloric acid was added. After being stirred for 6 hours, the reaction mixture was neutralized by adding triethylamine and concentrated. The resulting residue was dissolved in dichloromethane (80 mL), washed with brine, dried over sodium sulfate, concentrated, and purified by flash chromatography (hexane:ether, 20:1 to 2:1) to give alcohol YT-7 as a white solid (3.64 g, 19.8%).

PCC (3.4 g, 16 mmol) was added portionwise over 15 min to a mixture of alcohol YT-7 (2.51 g, 6.8 mmol) and powdered 3A molecular sieves (7.0 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-8 as a white solid (2.25 g, 90.1%).

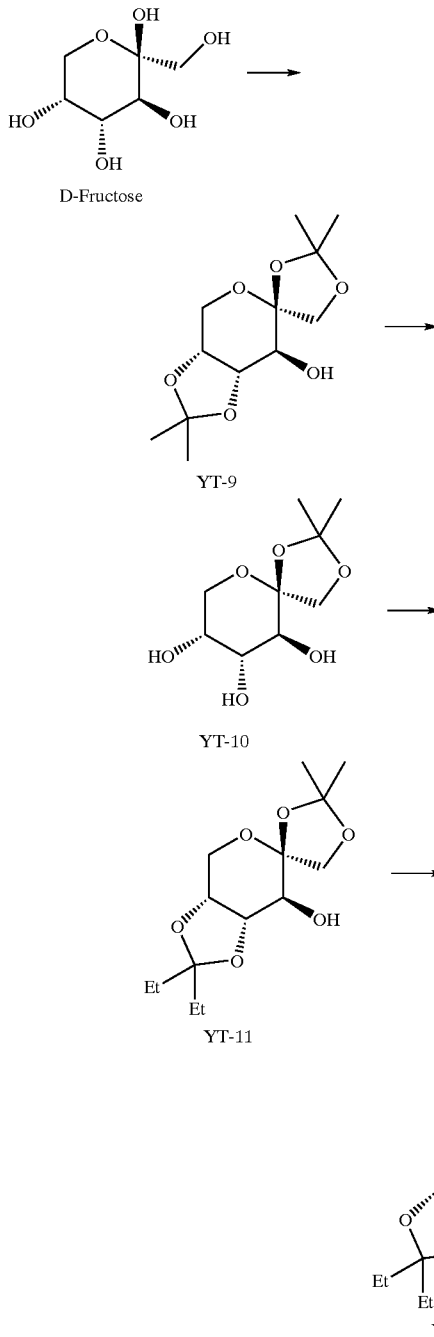

hours, the reaction mixture was neutralized with con. ammonium hydroxide and concentrated. The resulting solid residue was recrystallized from hexane-CH$_2$Cl$_2$ (4:1, v/v) to afford alcohol YT-9 as white needles (28.34 g, 53.2%).

To a solution of alcohol YT-9 (13.34 g, 51 mmol) in 150 mL of acetonitrile-water (9:1, v/v) was added DDQ (1.13 g, 5 mmol). After the mixture was stirred at room temperature for 6 hours, the solvent was evaporated. The resulting reddish solid residue was dissolved in ethyl acetate, dried over sodium sulfate, and concentrated to give alcohol YT-10 as a reddish solid (9.98 g, 88%).

To a solution of 3,3-dimethoxylpentane (4.41 g, 30 mmol) in 3-pentanone (22 mL) were added cupric sulfate (1.0 g) and con. sulfuric acid (0.05 g). After the mixture was stirred for 5 min, alcohol YT-10 (2.97 g, 13.5 mmol) was added. After being stirred additional 3.5 hours at room temperature, the reaction mixture was neutralized with triethylamine (0.8 mL) and filtered. The filtrate was concentrated and purified by flash chromatography (hexane:ether, 20:1 to 2:1, v/v) to afford alcohol YT-11 as a syrup (2.39 g, 61.5%).

PCC (4.10 g, 19.0 mmol) was added portionwise over 15 min to a mixture of alcohol YT-11 (2.03 g, 7.0 mmol) and powdered 3A molecular sieves (8.2 g) in dichloromethane (60 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-12 as a white solid (1.61 g, 79%).

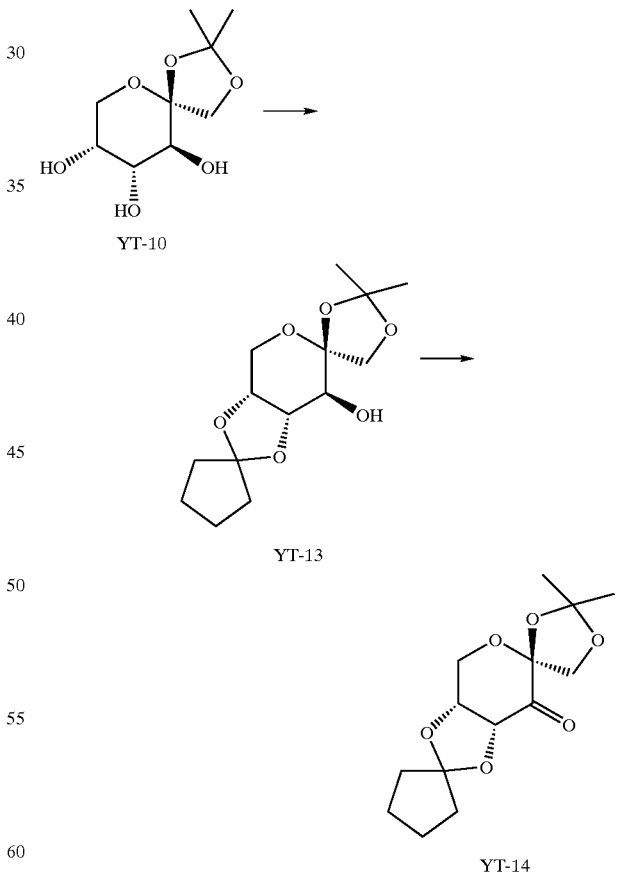

Preparation of Ketone YT-12

Perchloric acid (70%) (8.6 mL) was added to a suspension of D-fructose (36.84 g, 204.7 mmol) in acetone (740 mL) and 2,2-dimethoxypropane (14.8 mL, 120 mmol) at 0° C. (ice bath). After being stirred under nitrogen at 0° C. for 6

Preparation of Ketone YT-14

To a solution of 1,1-dimethoxylcyclopentane (3.9 g, 30 mmol) in cyclopentanone (20 mL) was added a solution of cupric sulfate (6.0 g) and con. sulfuric acid (0.2 g) in dioxane (20 mL). Upon stirring for 5 min, alcohol YT-10 (5.50 g, 25 mmol) was added. After being stirred 1.5 hours at room temperature, the reaction mixture was neutralized by adding triethylamine (1.0 mL) and filtered. The filtrate was concentrated and purified by flash chromatography (hexane:ehter, 20:1 to 3:2) to give alcohol YT-13 (2.45 g, 33.6%).

PCC (1.85 g, 19 mmol) was added portionwise over 15 min to a mixture of alcohol YT-13 (0.91 g, 3.2 mmol) and powdered 3A molecular sieves (8.2 g) in dichloromethane (60 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-14 as a white solid (0.69 g, 76%).

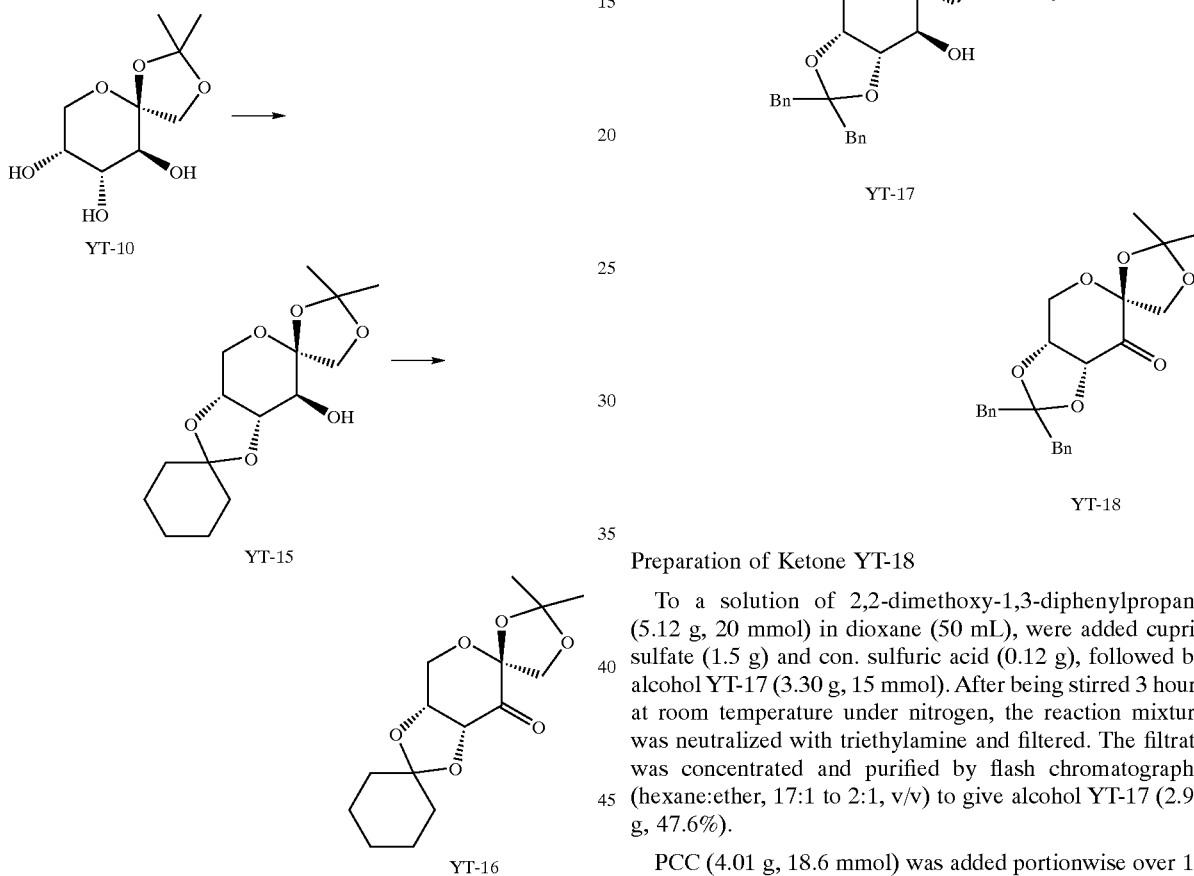

Preparation of Ketone YT-16

To a mixture of alcohol YT-10 (2.91 g, 13.2 mmol) in cyclohexanone (30 mL) and 1,1-dimethoxylcyclohexane (5.0 mL) were added cupric sulfate (5.0 g) and con. sulfuric acid (0.05 g). After being stirred for 50 min at room temperature under nitrogen, the reaction mixture was neutralized with triethylamine (1.0 mL) and filtered. The filtrate was concentrated and purified by flash chromatography (hexane:ether, 20:1 to 3:2) to give alcohol YT-15 (2.60 g, 65.5%).

PCC (5.06 g, 23.5 mmol) was added portionwise over 15 min to a mixture of alcohol YT-15 (2.60 g, 8.7 mmol) and powdered 3A molecular sieves (10.0 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 20:1 to 8:1, v/v) to afford YT-16 as a white solid (1.89 g, 73%).

Preparation of Ketone YT-18

To a solution of 2,2-dimethoxy-1,3-diphenylpropane (5.12 g, 20 mmol) in dioxane (50 mL), were added cupric sulfate (1.5 g) and con. sulfuric acid (0.12 g), followed by alcohol YT-17 (3.30 g, 15 mmol). After being stirred 3 hours at room temperature under nitrogen, the reaction mixture was neutralized with triethylamine and filtered. The filtrate was concentrated and purified by flash chromatography (hexane:ether, 17:1 to 2:1, v/v) to give alcohol YT-17 (2.94 g, 47.6%).

PCC (4.01 g, 18.6 mmol) was added portionwise over 15 min to a mixture of alcohol YT-17 (2.84 g, 6.9 mmol) and powdered 3A molecular sieves (8.02 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 20:1 to 2:1, v/v) to afford YT-18 as a white solid (1.96 g, 69.4%).

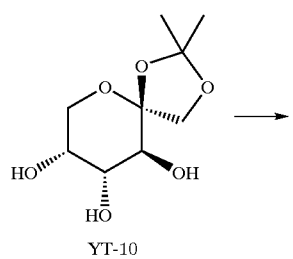
YT-10

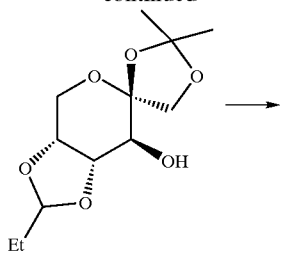

YT-19

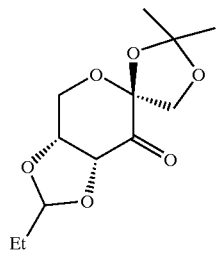

YT-20

Preparation of Ketone YT-20

To a mixture CH(OMe)$_3$ (2.2 mL, 2.22 g, 20 mmol), alcohol YT-10 (2.20 g, 10 mmol), and propanal (11.6 g, 200 mmol) in THF (40 mL) was added TsOH.H$_2$O (0.5 g) at room temperature. After being stirred overnight, the reaction mixture was neutralized by with triethylamine, concentrated, and purified by flash chromatography (hexane:ether, 20:1 to 4:3, v/v) to give alcohol YT-19 as a white solid (1.20 g, 46%).

PCC (2.2 g, 10.3 mmol) was added portionwise over 15 min to a mixture of alcohol YT-19 (1.0 g, 3.8 mmol) and powdered 3A molecular sieves (4.4 g) in dichloromethane (20 mL). After being stirred for 3 hours under nitrogen, the reaction mixture was filtered through celite and silicon gel (lower layer) and washed carefully with hexane-ether (1:1, v/v), the filtrate was concentrated to afford YT-20 as a solid (0.83 g, 84%).

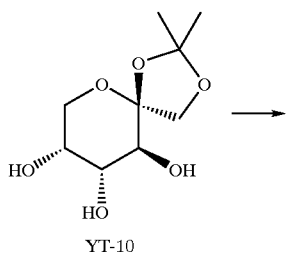

YT-10

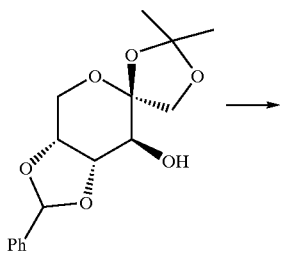

YT-21

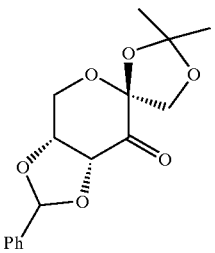

YT-22

Preparation of Ketone YT-22

To a mixture CH(OEt)$_3$ (3 mL, 18 mmol) and TsOH.H$_2$O (0.5 g) in dioxane (30 mL) was added benzaldehyde (15 mL) room temperature. After stirring for 1 hour, YT-10 (2.20 g, 10 mmol) was added. After 4 hours another patch of CH(OEt)$_3$ (2.0 mL, 12 mmol) was added. The reaction mixture was stirred for another 2 hours, neutralized with triethylamine (1 mL), concentrated, and purified by flash chromatography (hexane:ether, 20:1 to 3:2, v/v) to give alcohol YT-21 as a white solid (1.60 g, 52%).

PCC (1.9 g, 8.8 mmol) was added portionwise over 15 min to a mixture of alcohol YT-21 (1.0 g, 3.3 mmol) and powdered 3A molecular sieves (3.8 g) in dichloromethane (20 mL). After being stirred for 3 hours under nitrogen, the reaction mixture was filtered through celite and silicon gel (lower layer) and washed carefully with hexane:ether (1:1, v/v). The filtrate was concentrated to afford YT-22 as a solid (0.73 g, 74%).

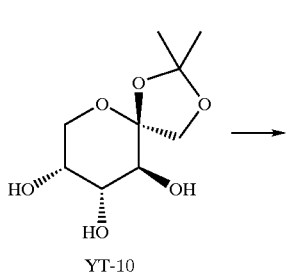

YT-10

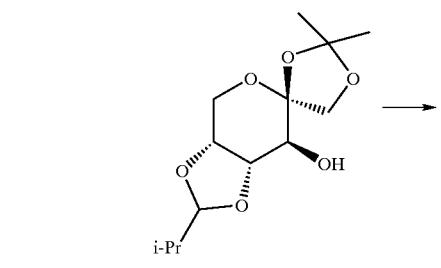

YT-23

YT-24

Preparation of Ketone YT-24

To a mixture CH(OEt)$_3$ (3 mL, 18 mmol) and TsOH.H$_2$O (0.2 g) in dioxane (30 mL) at 0° C. was added isobutanal (30 mL) room temperature. After stirring for 1 hour, YT-10 (2.2 g, 10 mmol) was added. After 4 hours, another patch of CH(OEt)$_3$ (2.0 mL, 12 mmol) was added. The reaction mixture was stirred for another 2 hours, neutralized with triethylamine (1 mL), concentrated, and purified by flash chromatography (hexane:ether, 20:1 to 3:2, v/v) to give alcohol YT-23 as a white solid (1.48 g, 54%).

PCC (1.93 g, 9.0 mmol) was added portionwise over 15 min to a mixture of alcohol YT-23 (0.91 g, 3.3 mmol) and powdered 3A molecular sieves (3.86 g) in dichloromethane (20 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-24 as a solid (0.64 g, 71%).

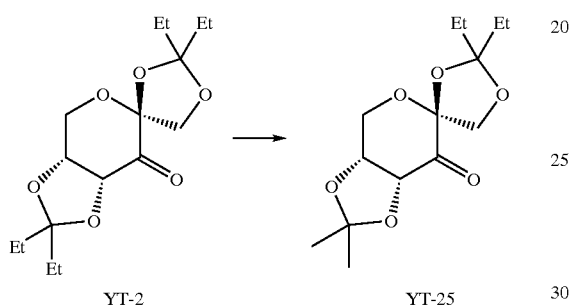

Preparation of Ketone YT-25

TsOH.H$_2$O (0.6 g) was added to a solution of ketone YT-2 (1.47 g, 4.7 mmol) in acetone (60 mL). After being stirred for 0.5 hour at room temperature, 2,2-dimethoxypropane (2.0 mL, 1.69 g, 16 mmol) was added. The mixture was stirred at room temperature for 3.5 hours, neutralized with triethylamine, concentrated, and purified by flash chromatography (hexane:ether, 15:1 to 10:1, v/v) to afford YT-25 as a syrup (0.62 g, 46.0%).

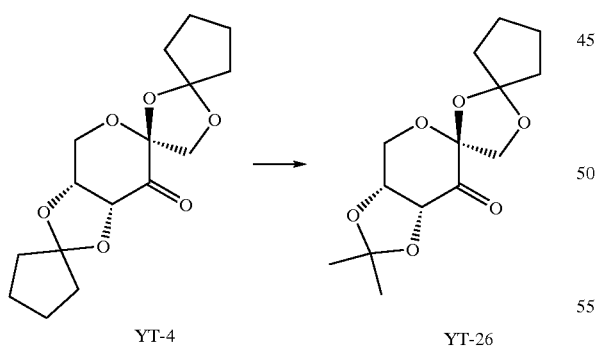

Preparation of Ketone YT-26

TsOH.H$_2$O (0.25 g) was added to a solution of ketone YT-4 (0.62 g, 2.0 mmol) in acetone (30 mL). After being stirred for 0.5 hour at room temperature, 2,2-dimethoxypropane (1.0 mL, 0.84 g, 8 mmol) was added. The mixture was stirred at room temperature for 3.5 hours, neutralized with triethylamine, concentrated, and purified by chromatography to give YT-26 as a solid (0.30 g, 52%).

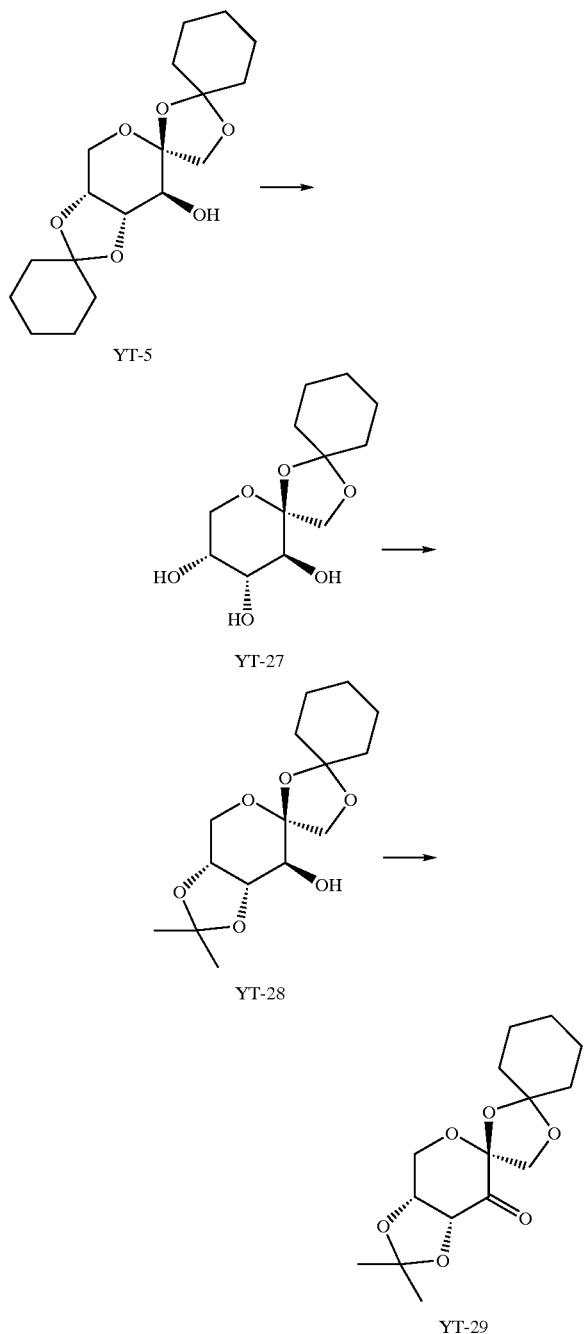

Preparation of Ketone YT-29

To a solution of alcohol YT-5 (5.10 g, 15 mmol) in acetonitrile-water (100 mL, 9:1, v/v ) was added DDQ (0.64 g, 3 mmol). After being stirred at room temperature for 3 hours, the reaction mixture was concentrated to a reddish residue. After being washed with ethyl acetate, the residue was dried under vacuum to give a reddish solid (YT-27) (2.19 g) which could be directly used for next reaction.

To a mixture of alcohol YT-27 (2.91 g), 2,2-dimethoxypropane (2.0 mL, 18 mmol), cupric sulfate (5.0 g) and acetone (40 mL) was added con. sulfuric acid (0.06 g). After being stirred for 1.5 hour at room temperature, the reaction mixture was neutralized with triethylamine (1 mL) and filtered. The filtrate was concentrated and purified by flash chromatography (hexane:ether, 10:1 to 3:2) to afford YT-28 as a solid (1.92 g, 76%).

PCC (3.05 g, 14.1 mmol) was added portionwise over 15 min to a mixture of alcohol YT-28 (1.57 g, 5.2 mmol) and powdered 3A molecular sieves (7.1 g) in dichloromethane (30 mL). After being stirred for 3 hours under nitrogen, the reaction mixture was diluted with hexane (50 mL), filtered through celite, and washed carefully with ether. The filtrate was concentrated and purified by passing through a short silica gel column (hexane:ether, 20:1 to 8:1, v/v) to afford YT-29 as a white solid (1.26 g, 80.8%).

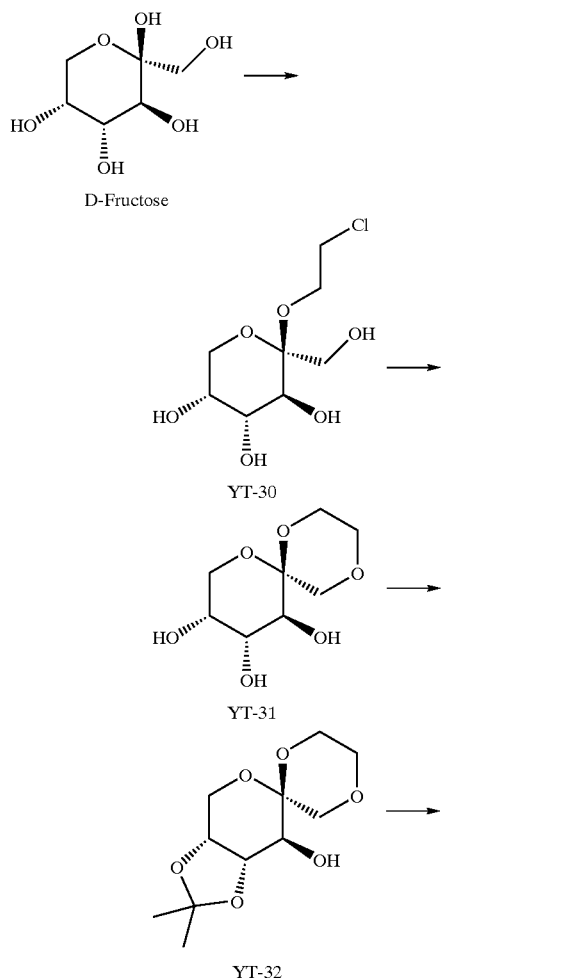

Preparation of Ketone YT-33

Perchloric acid (70%) (1 mL) was added to a mixture of alcohol YT-31 (10.08 g, 52 mmol) (for preparation see: J. Y. C. Chan, P. P. L. Cheong, L. Hough, and A. C. Richardson, *J. Chem. Soc. Perkin Trans.* 1, 1985,1447 ) and 2,2-dimethoxypropane (8.0 mL, 65 mmol) in acetone (100 mL) at 0° C. After being stirred under nitrogen at the temperature overnight, the reaction mixture was neutralized with con. $NH_4OH$ solution, and concentrated. The resulting residue was dissolved in dichloromethane (100 mL), washed with brine, dried with sodium sulfate, concentrated, and purified with flash chromatography (ethyl acetate:hexane, 3:1 to 1:1, v/v) to give alcohol YT-32 as a solid (4.22 g, 33%).

PCC (5.82 g, 27 mmol) was added portionwise over 15 min to a mixture of alcohol YT-32 (2.46 g, 10 mmol) and powdered 3A molecular sieves (11 g) in dichloromethane (50 mL). After being stirred overnight under nitrogen, the reaction mixture was filtered through celite and washed carefully with ether. The filtrate was concentrated and purified by passing through a short silica gel column (hexane:ether, 1:1, v/v) to afford YT-33 as a white solid (2.04 g, 83.6%).

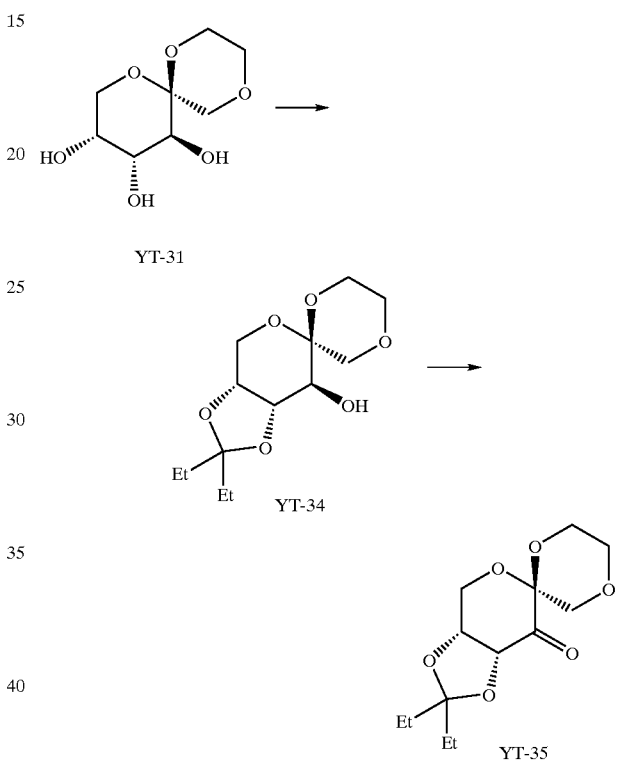

Preparation of Ketone YT-35

To a solution of 3-pentanone (3.44 g, 40 mmol) and trimethyl orthoformate (4.4 mL, 4.24 mmol) in methanol (10 mL) was added $TsOH.H_2O$ (0.05 g). After the solution was heated at 50–60° C. for 2 hours (during this time methyl formate formed was distilled off), the bath temperature was raised to 80° C. to distill off the methanol. Upon cooling to room temperature, a solution of alcohol YT-31 (6.18 g, 30 mmol) in THF (100 mL) was added, followed by 4 drops of 70% perchloric acid. After being stirred at room temperature overnight, the reaction mixture was neutralized with con. $NH_4OH$ and concentrated. The resulting residue was dissolved in dichloromethane (200 mL), washed with brine, dried over sodium sulfate, concentrated, and purified by flash chromatography (hexane:ether, 20:1 to 3:2, v/v) to give alcohol YT-34 as a solid (5.08 g, 61.8%).

PCC (10.52 g, 48.8 mmol) was added portionwise over 15 min to a mixture of alcohol YT-34 (5.00 g, 27.4 mmol) and powdered 3A molecular sieves (8.02 g) in dichloromethane (50 mL). After being stirred for 3 hours under nitrogen, the reaction mixture was filtered through celite and washed carefully with ether. The filtrate was concentrated and purified by passing through a short silica gel column

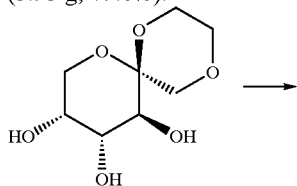

YT-31

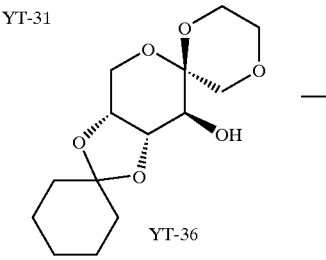

YT-36

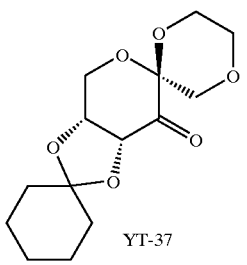

YT-37

Preparation of Ketone YT-37

To a solution of cyclohexanone (5.88 g, 60 mmol) and trimethyl orthoformate (4.4 mL, 4.24 mmol) in methanol (20 mL) was added TsOH.H$_2$O (0.05 g). After the solution was heated at 50–60° C. for 3 hours (during this time methyl formate formed was distilled off), the bath temperature was raised to 80° C. to distill off the methanol. Upon cooling to room temperature, a solution of alcohol YT-31 (8.24 g, 40 mmol) in THF (100 mL) was added, followed by 4 drops of 70% perchloric acid. After being stirred at room temperature for 5 hours, the reaction mixture was neutralized con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-36 as a solid (7.64 g, 66.3%).

PCC (10.52 g, 48.8 mmol) was added portionwise over 15 min to a mixture of alcohol YT-36 (5.76 g, 20 mmol) and powdered 3A molecular sieves (9.92 g) in dichloromethane (100 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-37 as a white solid (4.98 g, 86.5%).

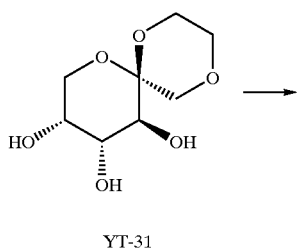

YT-31

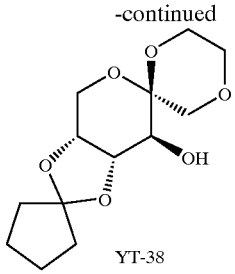

YT-38

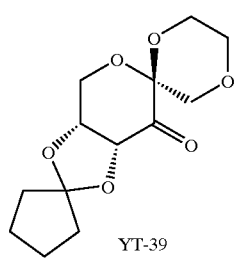

YT-39

Preparation of Ketone YT-39

To a solution of cyclopetanone (5.04 g, 60 mmol) and trimethyl orthoformate (4.4 mL, 4.24 g, 40 mmol) in methanol (20 mL) was added TsOH.H$_2$O (0.05 g). After the solution was heated at 50–60° C. for 3 hours (during this time methyl formate formed was distilled off), the bath temperature was raised to 80° C. to distill off the methanol. Upon cooling to room temperature, a solution of alcohol YT-31 (8.24 g, 40 mmol) in THF (100 mL) was added, followed by 4 drops of 70% perchloric acid. After being stirred at room temperature for 5 hours, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-38 as a solid (5.97 g, 51.8%).

PCC (9.92 g, 46 mmol) was added portionwise over 15 min to a mixture of alcohol YT-38 (5.48 g, 20 mmol) and powdered 3A molecular sieves (20 g) in dichloromethane (100 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-39 as a white solid (4.29 g, 78%).

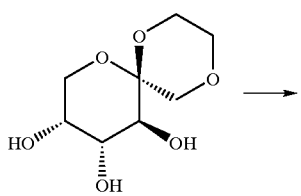

YT-31

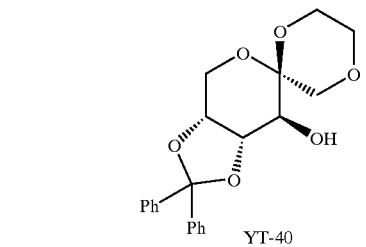

YT-40

-continued

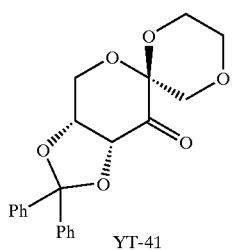

YT-41

Preparation of ketone YT-41

To a solution of benzophenone (4.86 g, 26.7 mmol) and trimethyl orthoformate (3.1 mL, 28.3 mmol) in methanol (20 mL) was added TsOH.H$_2$O (0.02 g).

After the solution was heated at 50–60° C. for 3 hours (during this time methyl formate formed was distilled off), the bath temperature was raised to 100° C. to distill off the methanol. Upon cooling to room temperature, a solution of alcohol YT-31 (6.18 g, 30 mmol) in THF (150 mL) was added, followed by 3 drops of 70% perchloric acid. After being stirred at room temperature overnight, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-40 as a solid (7.24 g, 67%).

PCC (4.0 g, 18.6 mmol) was added portionwise over 15 min to a mixture of alcohol YT-40 (2.79 g, 8.1 mmol) and powdered 3A molecular sieves (80 g) in dichloromethane (80 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-41 as a white solid (1.43 g, 51%).

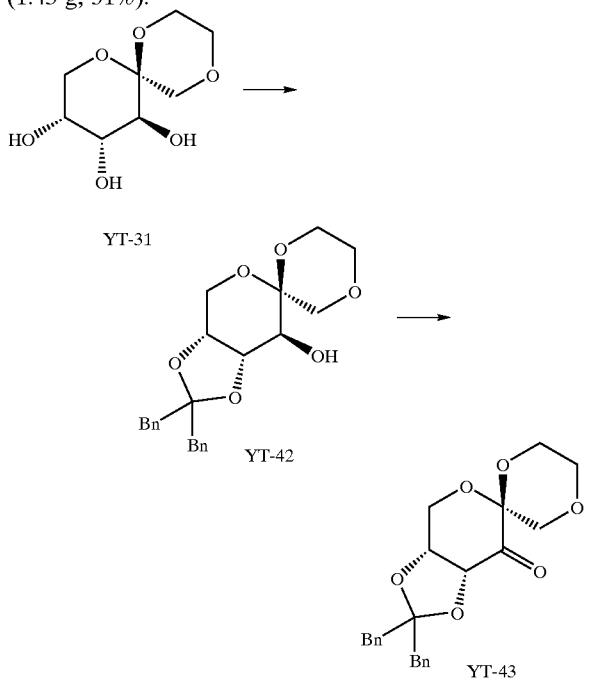

Preparation of ketone YT-43

To a solution of 1,3-diphenylacetone (2.1 g, 10 mmol) and trimethyl orthoformate (1.2 mL, 11 mmol) in methanol (10 mL) was added TsOH.H$_2$O (0.01 g). After the solution was heated at 50–60° C. for 3 hours (during this time methyl formate formed was distilled off), the bath temperature was raised to 90° C. to distill off the methanol. Upon cooling to room temperature, a solution of alcohol YT-31 (3.10 g, 15 mmol) in THF (100 mL) was added, followed by 3 drops of 70% perchloric acid. After being stirred at room temperature overnight, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-42 (2.36 g, 59.2%).

PCC (2.34 g, 10.4 mmol) was added portionwise over 15 min to a mixture of alcohol YT-42 (1.8 g, 4.5 mmol) and powdered 3A molecular sieves (5.0 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-43 as a solid (1.68 g, 93%).

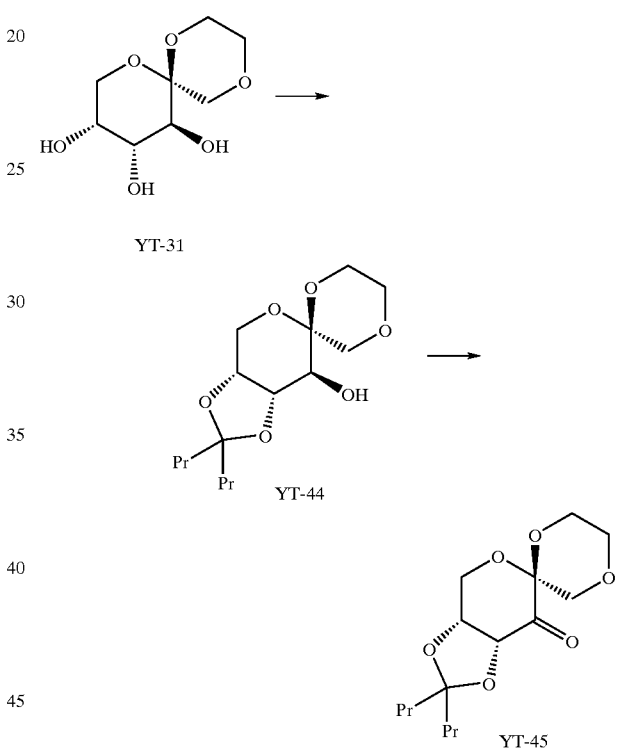

Preparation of Ketone YT-45

To a solution of 4-heptanone (11.4 g, 100 mmol) and trimethyl orthoformate (4.24 g, 40 mmol) in methanol (50 mL) was added TsOH.H$_2$O (0.01 g). After the solution was heated at 50–70° C. for 2 hours (during this time methyl formate formed was distilled off), the bath temperature was raised to 100° C. to distill off the methanol. Upon cooling to room temperature, a solution of alcohol YT-31 (8.8 g, 43 mmol) in dioxane (60 mL) was added, followed by cupric sulfate (6.0 g) and 3 drops of con. sulfuric acid. After being stirred at room temperature overnight, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 50:1 to 3:1, v/v) to give alcohol YT-44 as a syrup (5.56 g, 43%).

PCC (9.12 g, 42.3 mmol) was added portionwise over 15 min to a mixture of alcohol YT-44 (4.73 g, 15.7 mmol) and powdered 3A molecular sieves (18.24 g) in dichloromethane (100 mL). After being stirred for 3 h under nitrogen, the reaction mixture was filtered through celite and washed carefully with ether. The filtrate was concentrated and purified by passing through a short silica gel column (hexane:ether, 1:1, v/v) to afford YT-45 as a syrup (3.89 g, 83%).

Epoxidation Using Hydrogen Peroxide and a Nitrile Compound as the Oxidant

This example illustrates the asymmetric epoxidation of a variety of olefins using a mixture of hydrogen peroxide and a nitrile compound as the oxidizing agent for the chiral ketone 1, and the effect of variety of solvents on the epoxide yield.

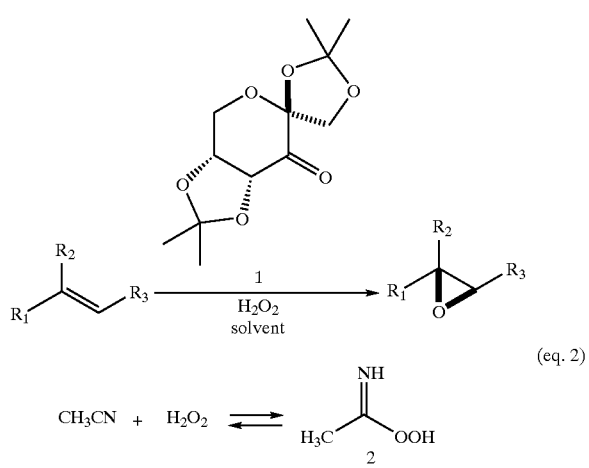

(eq. 1)

(eq. 2)

A solution of the olefin (1 mmol), ketone 1 (0.3 mmol), hydrogen peroxide (30%, 0.5 mL, 5 mmol) in $CH_3CN$ (2 mL)-buffer ($AcOH$—$K_2CO_3$) (the buffer pH was adjusted to 10.3 by adding HOAc to 0.1 M $K_2CO_3$) (1 mL) was stirred at room temperature for 2 h, a 40% conversion was obtained. Analysis of the epoxide product using chiral GC (Chiraldex G-TA) showed 86% ee. When the reaction was carried out in other solvents, such as DMF, THF, $CH_2Cl_2$, EtOH, or dioxane, instead of $CH_3CN$, only trace amounts of the epoxide (<1%) were detected by GC, suggesting that hydrogen peroxide itself could not effectively generate the dioxirane and that $CH_3CN$ acted as an activator. Without being bound by any theory, it is believed that in the case of $CH_3CN$, the actual oxidant responsible for the formation of the dioxirane was peroxyimidic acid 2 (eq. 2). Asymmetric epoxidation also occurred when other nitrites such as $CH_3CH_2CN$, $CH_3CH_2CH_3CN$ were used.

Effect of pH on Epoxidation using Hydrogen Peroxide and a Nitrile Compound

This example illustrates the effect pH on the yield and the reaction kinetics of epoxidation using a mixture of hydrogen peroxide and a nitrile compound as the oxidizing agent for the chiral ketone 1.

Figure 17:
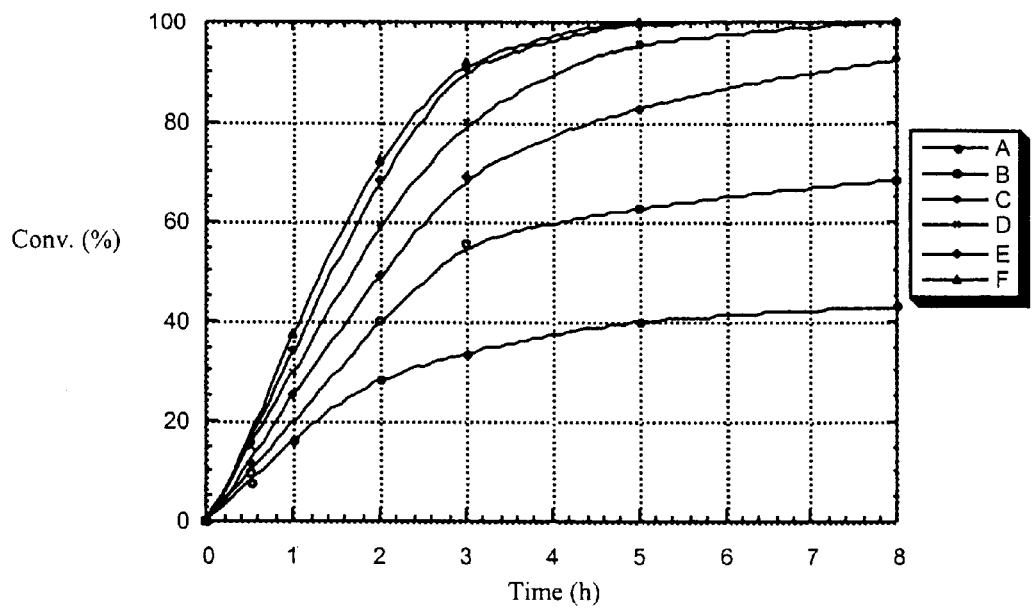
FIG. 17 shows the effect of the concentration of potassium carbonate on epoxidation reaction using chiral ketone 1 of FIG. 1 and an oxidizing agent derived from a mixture of hydrogen peroxide and a nitrile compound.

Using trans-β-methylstyrene as the olefin, the epoxidation procedure described above for using hydrogen peroxide and a nitrile compound was followed using a various amount of $K_2CO_3$. The results of potassium carbonate at 0.05 M, 0.1 M, 0.4 M, 0.6 M, 0.8 M and 1.0 M are plotted as shown in FIG. 17. High conversion of the olefin to the epoxide was obtained when the sufficient amount of potassium carbonate was used. When potassium carbonate was above 0.6 M, over 90% ee of the epoxide was obtained.

Figure 18:
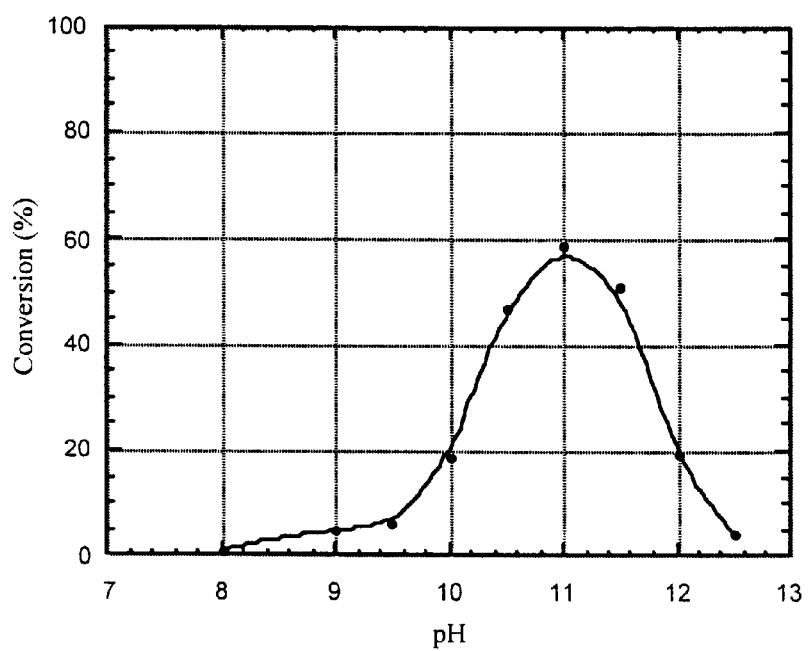
FIG. 18 shows the pH effect of epoxidation reaction of trans-β-methylstyrene using CF₃COCH₃ as a ketone.

In FIG. 17, the curves presented are: (A) 0.05 M $K_2CO_3$ in $4 \times 10^{-4}$ M of EDTA (pH11.1), (B) 0.1 M $K_2CO_3$ in $4 \times 10^{-4}$ M of EDTA (pH 11.3), (C) 0.4 M $K_2CO_3$ in $4 \times 10^{-4}$ M of EDTA (pH 11.6), (D) 0.6 M $K_2CO_3$ in $4 \times 10^{-4}$ M of EDTA (pH 11.7), (E) 0.8 M $K_2CO_3$ in $4 \times 10^{-4}$ M of EDTA (pH 11.8), (F) 1.0 M $K_2CO_3$ in $4 \times 10^{-4}$ M of EDTA (pH 11.9) (The pH indicated above is the pH of the $K_2CO_3$ solution. The pH varied upon adding other reaction components as well as the reaction time. This variation became smaller when higher concentration of $K_2CO_3$ was used. As FIG. 18 shows, in general the desired pH range for the epoxidation reaction is from pH about 10 to pH about 12.

Further studies showed that this epoxidation system could also be extended to other substrates, obtaining good yields and ee's in each case (See FIG. 25).

Representative Epoxidation Using Hydrogen Peroxide and a Nitrile Compound

This example illustrates a representative asymmetric epoxidation procedure (FIG. 25, entry 1) at 1.0 M $K_2CO_3$.

To a solution of trans-β-methylstyrene (0.118 g, 1 mmol) and ketone 1 (0.077 g, 0.3 mmol) in $CH_3CN$ (2 mL) was added a solution of 1.0 M $K_2CO_3$ in $4 \times 10^{-4}$ M of EDTA (1 mL) followed by $H_2O_2$ (30%, 0.3 mL, 3 mmol) at 0° C. Upon stirring at 0° C. for reaction mixture was quenched with hexane (5 mL), extracted with hexane, washed with saturated $Na_2S_2O_3$ and brine, dried ($Na_2SO_4$), filtered, concentrated, and purified by chromatography (silica gel was buffered with 1% $Et_3N$ in hexane, using hexane-ether as eluent) to afford the epoxide product as a colorless oil (0.113 g, 84% yield, 92% ee).

Effect of a Ketone on Epoxidation Using Hydrogen Peroxide and a Nitrile Compound This example illustrates effect of ketone on the epoxidation reaction.

Using the procedure described above for representative epoxidation using hydrogen peroxide and a nitrile compound, only 1% conversion of the olefin to the epoxide was obtained after 5 h at 0° C. in the absence of chiral ketone 1.

Effect of a Nitrile Compound on Epoxidation Using Hydrogen Peroxide

This example illustrates the effect of a nitrile compound on the epoxidation reaction.

acetonitrile, using other organic solvents, such as dimethylformamide (DMF), tetrahydrofuran (THF), methylene chloride, ethanol or dioxane, epoxidation of an olefin was carried out using the above described procedure for "Epoxidation Reaction using hydrogen peroxide and a nitrile compound." In all cases only a trace amount (<1%) of the epoxide was detected by gas chromatography.

Acid Catalyzed Rearrangment

In the following examples, enantiomerically enriched enol ester epoxides are prepared by the procedures disclosed above.

This example illustrates a representative procedure for acid-catalyzed rearrangement of enol ester epoxides.

p-TsOH as Catalyst

To a solution of (1R, 2R)-2-benzoyloxy-1,2-epoxycyclohexane (0.030 g, 0.137 mmol, 93% ee) in anhydrous nitromethane (0.4 mL) was added p-TsOH (0.0024 g, 0.0137 mmol). Upon stirring at room temperature for 10 min, the reaction mixture was quenched with saturated $NaHCO_3$ solution, extracted with ether, dried over anhydrous $Na_2SO_4$, filtered, concentrated, and purified on buffered silica gel (0.5–1% $Et_3N$) by flash column chromatography [EtOAc—$CH_2Cl_2$-hexane (3:7:40)] to afford (R)-2-benzoyloxy cyclohexanone (0.0267 g, 89% yield, 90% ee).

YbCl3 as Catalyst

To a solution of (1R,2R)-2-benzoyloxy-1,2-epoxycyclohexane (0.030 g, 0.137 mmol, 93% ee) in anhydrous $CH_2Cl_2$ (0.4 mL) was added $YbCl_3$ (0.0038 g, 0.0137 mmol). Upon stirring at room temperature for 30 min, the reaction mixture was quenched with saturated NaHCO₃ solution, extracted with ether, dried over anhydrous Na₂SO₄, filtered, concentrated, and purified on buffered silica gel (0.5–1% Et₃N) by flash column chromatography [EtOAc-CH₂Cl₂-hexane (3:7:40)] to afford (S)-2-benzoyloxy cyclohexanone (0.022 g, 73% yield, 88% ee).

Synthesis of α-Acyl Carbonyl Compound from an Enol Ester Epoxide

This example illustrates a representative procedure for producing an α-acyl carbonyl compound from an enol ester epoxide.

Preparation of Enantiomerically Enriched Enol Ester Epoxide

To a solution of (R)-(+)-binaphthol (7.9 mg, 0.0275 mmol) in CH₂Cl₂ (0.5 mL) was added a solution of Ti(O$^i$Pr)₄ (3.8 μL, 3.6 mg, 0.0125 mmol) in CH₂Cl₂ (0.5 mL). Upon stirring at room temperature for 5–10 h, the reaction mixture was concentrated and dried using a vacuum pump (ca. 0.5 h). The catalyst was then dissolved in Et₂O (1 mL) and cooled in an ice bath. To this solution was added a solution of racemic 1-benzoyloxy-1,2-epoxycyclohexane (0.109 g, 0.5 mmol) in Et₂O (1 mL). After stirring at 0° C. for 1 h, the reaction mixture was quenched with saturated NaHCO₃ solution (4 mL) and poured into a mixture of ether (20 mL) and saturated NaHCO₃ solution (10 mL). The organic layer was washed with water and brine, dried (Na₂SO₄) (ca. 10 min), and rapidly filtered through a plug of silica gel (ca. 10 g) (pre-treated with 5% Et₃N in hexane and washed thoroughly with hexane to remove Et₃N before use). The silica gel was further washed with Et₂O (10 mL). The combined ether solutions were concentrated to give a mixture of (R)-1-benzoyloxy-1,2-epoxycyclohexane and (R)-2-benzoyloxycyclohexanone. After a sample was taken for the determination of the conversion and ee's, the mixture was purified by flash chromatography (silica gel was pre-treated with 5% Et₃N) using hexane-CH₂Cl₂—EtOAc (84:10:6) as eluent to afford (R)-1-benzoyloxy-1,2-epoxycyclohexane as a colorless oil (0.0365 g, 34% yield, 98% ee).

Preparation of Enantiomerically Enriched α-Acyloxy Ketone

To a solution of (R)-(+)-binaphthol (7.9 mg, 0.0275 mmol) in CH₂Cl₂ (0.5 mL) was added a solution of Ti(O$^i$Pr)₄ (3.8 uL, 3.6 mg, 0.0125 mmol) in CH₂Cl₂ (0.5 mL). Upon stirring at room temperature for 5–10 h, the reaction mixture was concentrated and dried using a vacuum pump (ca. 0.5 h). The catalyst was then dissolved in Et₂O (1 mL) and cooled in an ice bath. To this solution was added a solution of racemic 1-benzoyloxy-1,2-epoxycyclohexane (0.109 g, 0.5 mmol) in Et₂O (1 mL). After stirring at 0° C. for 1 h, the reaction mixture was quenched with saturated NaHCO₃ solution (4 mL) and poured into a mixture of ether (20 mL) and saturated NaHCO₃ solution (10 mL). The organic layer was washed with water and brine, dried (Na₂SO₄), and rapidly filtered through a plug of silica gel (ca. 10 g) (pre-treated with 5% Et₃N in hexane and washed thoroughly with hexane to remove Et₃N before use). The silica gel was further washed with Et₂O (10 mL). The combined ether solutions were concentrated to give a residue. Upon drying under vacuum for 1 h, the mixture was dissolved in CH₂Cl₂ (4 mL) followed by addition of anhydrous p-TsOH (8.6 mg, 0.05 mmol). After stirring at room temperature for 20 min, the mixture was rapidly filtered through a plug of silica gel (ca. 10 g) (without Et₃N treatment) followed by washing with ether (2×10 mL). The combined solutions were concentrated to give (R)-2-benzoyloxycyclohexanone as a white solid (0.0845 g, 78% yield, 93% ee).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of producing an epoxide from an olefin comprising:

contacting an oxidizing agent with an olefin in the presence of a chiral ketone under conditions sufficient to produce an epoxide from the olefin, wherein the chiral ketone is selected from the group consisting of a compound of the formula:

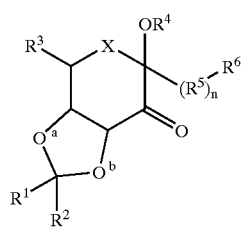

or a derivative thereof which is capable of converting to the chiral ketone of Formula I under the reaction conditions, wherein bonds a and b are of cis-configuration relative to each other;

n is 0 or 1;

X is selected from the group consisting of O and CR⁷R⁸, where R⁷ and R⁸ is independently selected from the group consisting of hydrogen, alkyl, haloalkyl and heteroalkyl, or R⁷ together with R⁴ together with the atoms to which they are attached to form an optionally substituted heterocyclyl;

each of R¹ and R² is independently selected from the group consisting of hydrogen or alkyl, or R¹ and R² together with atoms to which they are attached to form a cycloalkyl;

R³ is selected from the group consisting of hydrogen and OR⁹, where R⁹ is a hydroxyl protecting group or aryl group;

R⁵ is alkylene;

R⁴ is hydrogen or a hydroxy protecting group; and

R⁶ is hydrogen, alkyl, or —OR$^a$, where R$^a$ is hydrogen or a hydroxy protecting group; or R⁴ and R⁶ together with the atoms to which they are attached to form an optionally substituted heterocyclyl.

2. The method of claim 1, wherein R⁴ and R⁶ or R⁴ and R⁷ together with the atoms to which they are attached to form an optionally substituted heterocyclyl.

3. The method of claim 1, wherein R³ is hydrogen.

4. The method of claim 3, wherein X is O or CH₂.

5. The method of claim 1, wherein the chiral ketone is of the formula:

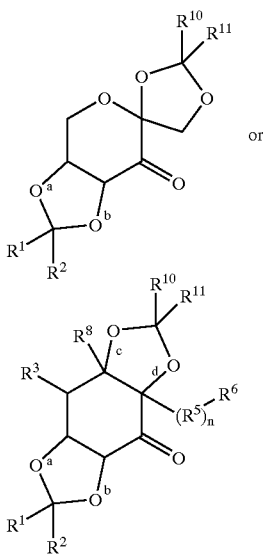

IIA or

IIB or a derivative thereof which is capable of converting to the chiral ketone of Formula I under the reaction conditions, wherein a, b, n, $R^1$, $R^2$, $R^3$, $R^5$, $R^6$ and $R^8$ are those defined in claim 1;

bonds c and d are cis-configuration relative to each other; and $R^{10}$ and $R^{11}$ are independently hydrogen or alkyl, or $R^{10}$ and $R^{11}$ together with atoms to which they are attached to form a cycloalkyl.

6. The method of claim 5, wherein the chiral ketone is of the formula:

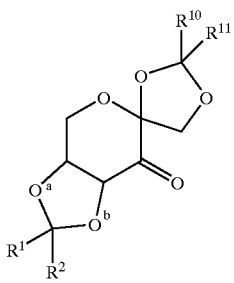

II or a derivative thereof which is capable of converting to the chiral ketone of Formula I under the reaction conditions, wherein a, b, $R^1$ and $R^2$ are those defined in claim 1; and $R^{10}$ and $R^{11}$ are those defined in claim 5.

7. The method of claim 6, wherein each of $R^1$ and $R^2$ is independently hydrogen or $C_1$–$C_4$ alkyl or $R^1$ and $R^2$ together with the atoms to which they are attached to form cyclopentyl, cyclohexyl or cycloheptyl.

8. The method of claim 7, wherein $R^{10}$ and $R^{11}$ are $C_1$–$C_4$ alkyl or $R^{10}$ and $R^{11}$ together with the atoms to which they are attached to form cyclopentyl, cyclohexyl or cycloheptyl.

9. The method of claim 8, wherein the chiral ketone is of the formula:

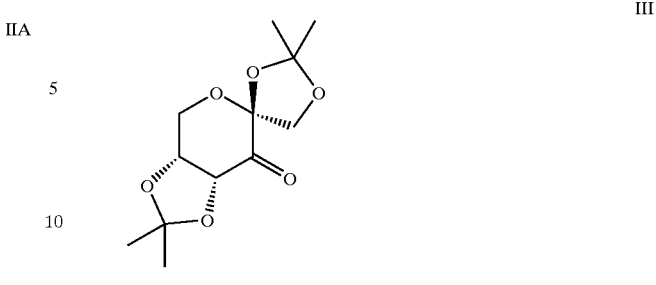

III an enantiomer thereof, or a derivative thereof which is capable of converting to the chiral ketone of Formula III or its enantiomer under the reaction conditions.

10. The method of claim 1, wherein the oxidizing agent comprises a peracid, an oxidizer derived from a mixture of hydrogen peroxide and a nitrile compound, potassium peroxomonosulfate, sodium perborate, or a mixture thereof.

11. The method of claim 1, wherein the oxidizing agent is potassium peroxomonosulfate or is derived from a mixture comprising a nitrile compound and hydrogen peroxide.

12. The method of claim 1 further comprising maintaining the pH of the reaction mixture at from about pH 10 to about pH 14.

13. The method of claim 1, wherein the epoxide is an enol ester epoxide and said method further comprises stereoselectively producing an α-acyloxy carbonyl compound from the enol ester epoxide, said α-acyloxy carbonyl producing step comprising:

contacting the enol ester epoxide with an acid catalyst under conditions sufficient to stereoselectively produce the α-acyloxy carbonyl compound.

14. The method of claim 13, wherein the α-acyloxy carbonyl is produced with inversion of stereochemistry.

15. The method of claim 13, wherein the α-acyloxy carbonyl is produced with retention of stereochemistry.

16. A method for stereoselectively producing an α-acyloxy carbonyl compound from an enol ester olefin comprising:

(a) contacting an oxidizing agent with the enol ester olefin in the presence of a chiral ketone under conditions sufficient to produce an enol ester epoxide from the enol ester olefin, wherein the chiral ketone is selected from the group consisting of a compound of the formula:

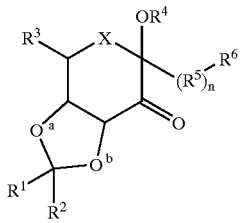

I or a derivative thereof which is capable of converting to the chiral ketone of Formula I under the reaction conditions, wherein bonds a and b are of cis-configuration relative to each other;

n is 0 or 1;

X is selected from the group consisting of O and $CR^7R^8$, where $R^7$ and $R^8$ is independently selected from the group consisting of hydrogen, alkyl, haloalkyl and heteroalkyl, or $R^7$ together with $R^4$ together with the atoms to which they are attached to form an optionally substituted heterocyclyl;

each of $R^1$ and $R^2$ is independently selected from the group consisting of hydrogen or alkyl, or $R^1$ and $R^2$ together with atoms to which they are attached to form a cycloalkyl;

R³ is selected from the group consisting of hydrogen and OR⁹, where R⁹ is a hydroxyl protecting group or aryl;

R⁵ is alkylene;

R⁴ is hydrogen or a hydroxy protecting group; and

R⁶ is hydrogen, alkyl, or —ORᵃ, where Rᵃ is hydrogen or a hydroxy protecting group; or R⁴ and R⁶ together with the atoms to which they are attached to form an optionally substituted heterocyclyl; and (b) contacting the enol ester epoxide with an acid catalyst under conditions sufficient to stereoselectively produce the α-acyloxy carbonyl compound.

17. The method of claim 16, wherein the α-acyloxy carbonyl is produced with inversion of stereochemistry.

18. The method of claim 16, wherein the α-acyloxy carbonyl is produced with retention of stereochemistry.

19. The method of claim 16, wherein the chiral ketone is of the formula:

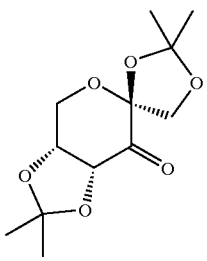

III an enantiomer thereof, or a derivative thereof which is capable of converting to the chiral ketone of Formula III or its enantiomer under the reaction conditions.

20. A method for increasing a relative concentration of at least one stereoisomer of a compound having at least one olefinic moiety, from a stereoisomer mixture of the compound, said method comprising:

contacting an oxidizing agent with the stereoisomer mixture of the compound in the presence of a chiral ketone to producing an epoxide of at least one stereoisomer of the compound at a relatively higher rate than an epoxide of another stereoisomer of the compound, wherein the chiral ketone is selected from the group consisting of a compound of the formula:

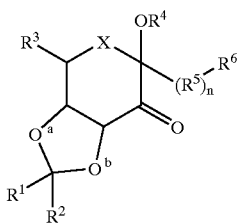

I or a derivative thereof which is capable of converting to the chiral ketone of Formula I under the reaction conditions, wherein bonds a and b are of cis-configuration relative to each other;

n is 0 or 1;

X is selected from the group consisting of O and CR⁷R⁸, where R⁷ and R⁸ is independently selected from the group consisting of hydrogen, alkyl, haloalkyl and heteroalkyl, or R⁷ together with R⁴ together with the atoms to which they are attached to form an optionally substituted heterocyclyl;

each of R¹ and R² is independently selected from the group consisting of hydrogen or alkyl, or R¹ and R² together with atoms to which they are attached to form a cycloalkyl;

R³ is selected from the group consisting of hydrogen and OR⁹, where R⁹ is a hydroxyl protecting group or aryl;

R⁵ is alkylene;

R⁴ is hydrogen or a hydroxy protecting group; and

R⁶ is hydrogen, alkyl, or —ORᵃ, where Rᵃ is hydrogen or a hydroxy protecting group; or R⁴ and R⁶ together with the atoms to which they are attached to form an optionally substituted heterocyclyl.

21. The method of claim 20, wherein the stereoisomer mixture comprises a geometrical isomer of the olefin moiety.

22. The method of claim 20, wherein the compound further comprises at least one chiral center.

23. The method of claim 22, wherein the stereoisomer mixture comprises a stereoisomer of the chiral center.

24. The method of claim 23, wherein said stereoisomer mixture is a racemic mixture.

25. The method of claim 20, wherein the chiral ketone is of the formula:

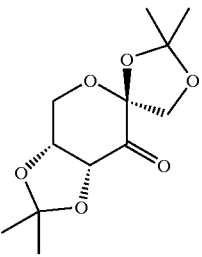

(III)

an enantiomer thereof, or a derivative thereof which is capable of converting to the chiral ketone of Formula III or its enantiomer under the reaction conditions.

* * * * *